United States Patent
Abdou

(10) Patent No.: US 10,857,003 B1
(45) Date of Patent: Dec. 8, 2020

(54) DEVICES AND METHODS FOR VERTEBRAL STABILIZATION

(71) Applicant: Samy Abdou, San Diego, CA (US)

(72) Inventor: Samy Abdou, San Diego, CA (US)

( * ) Notice: Subject to any disclaimer, the term of this patent is extended or adjusted under 35 U.S.C. 154(b) by 476 days.

(21) Appl. No.: 15/294,382

(22) Filed: Oct. 14, 2016

Related U.S. Application Data

(60) Provisional application No. 62/284,944, filed on Oct. 14, 2015.

(51) Int. Cl.
| | |
|---|---|
| *A61F 2/46* | (2006.01) |
| *A61F 2/44* | (2006.01) |
| *A61B 17/70* | (2006.01) |
| *A61B 17/16* | (2006.01) |
| *A61B 17/17* | (2006.01) |
| *A61B 17/56* | (2006.01) |

(52) U.S. Cl.
CPC ........ *A61F 2/4611* (2013.01); *A61B 17/1671* (2013.01); *A61B 17/1757* (2013.01); *A61F 2/442* (2013.01); *A61F 2/4601* (2013.01); *A61B 2017/564* (2013.01); *A61F 2002/4635* (2013.01)

(58) Field of Classification Search
CPC ................ A61F 2/44–447; A61B 17/70–7098
See application file for complete search history.

(56) References Cited

U.S. PATENT DOCUMENTS

| | | |
|---|---|---|
| 167,625 A | 9/1875 | Charles |
| 203,512 A | 5/1878 | Nicholas |

(Continued)

FOREIGN PATENT DOCUMENTS

| | | |
|---|---|---|
| DE | 3114872 A1 | 10/1982 |
| DE | 3741493 A1 | 6/1989 |

(Continued)

OTHER PUBLICATIONS

Bridwell K. H., et al., "Decision Making Regarding Smith-Petersen vs. Pedicle Subtraction Osteotomy vs. Vertebral Column Resection for Spinal Deformity," Spine, 2006, vol. 31(19S), pp. S171-S178.

(Continued)

*Primary Examiner* — Nicholas J Plionis
(74) *Attorney, Agent, or Firm* — Gazdzinski & Associates, PC

(57) ABSTRACT

Devices, systems and methods for the treatment of spinal instability and/or stenosis of the spinal canal and neural foramina. In one embodiment, a functional spinal unit (FSU) of a subject is approached through a lateral or antero-lateral corridor, and both an anterior and posterior column of the FSU are manipulated, implanted and/or otherwise surgically treated through the same intra-abdominal surgical corridor. A method is disclosed to reach the posterior aspect of the FSU, wherein the intra-abdominal surgical corridor is extended posterior to the psoas major muscle and through the thoraco-lumbar fascia in order to reach the transverse process and/or facet joint. Multiple trajectories for bone screw fixation of the vertebral bone are additionally disclosed. In another embodiment, the FSU is approached through the above corridor and a second posterior skin incision and corridor. The combination of the corridors provided circumferential access to the FSU.

30 Claims, 27 Drawing Sheets

(56) References Cited

U.S. PATENT DOCUMENTS

| | | |
|---|---|---|
| 203,624 A | 5/1878 | Josias |
| 229,347 A | 6/1880 | Shepherd |
| 267,269 A | 11/1882 | John |
| 824,983 A | 7/1906 | Charles |
| 944,725 A | 12/1909 | Walton |
| 1,015,890 A | 1/1912 | Alfred |
| 1,156,440 A | 10/1915 | John |
| 1,213,599 A | 1/1917 | Charles |
| 1,785,709 A | 12/1930 | Harry et al. |
| 2,248,054 A | 7/1941 | Becker |
| 2,329,398 A | 9/1943 | Duffy |
| 2,370,407 A | 2/1945 | McCartney |
| 2,574,352 A | 11/1951 | Senter |
| 2,677,369 A | 5/1954 | Knowles |
| 2,774,350 A | 12/1956 | Cleveland, Jr. |
| 3,025,853 A | 3/1962 | Mason |
| 3,037,596 A | 6/1962 | Fordyce |
| 3,072,423 A | 1/1963 | Charlton |
| 3,073,584 A | 1/1963 | Troeger |
| 3,090,386 A | 5/1963 | Babcock |
| 3,236,141 A | 2/1966 | Smith |
| 3,242,922 A | 3/1966 | Thomas |
| 3,260,412 A | 7/1966 | Larkin |
| 3,277,555 A | 10/1966 | Kutash |
| 3,374,786 A | 3/1968 | Callender, Jr. |
| 3,383,769 A | 5/1968 | Davis |
| 3,384,077 A | 5/1968 | Gauthier |
| 3,426,364 A | 2/1969 | Limb |
| 3,604,487 A | 9/1971 | Gilbert |
| 3,648,691 A | 3/1972 | Lumb et al. |
| 3,659,595 A | 5/1972 | Haboush |
| 3,695,259 A | 10/1972 | Yost |
| 3,708,883 A | 1/1973 | Flander |
| 3,741,205 A | 6/1973 | Markolf et al. |
| 3,749,088 A | 7/1973 | Kohlmann |
| 3,791,380 A | 2/1974 | Dawidowski |
| 3,795,981 A | 3/1974 | Franklin et al. |
| 3,805,219 A | 4/1974 | Bright |
| 3,825,992 A | 7/1974 | Troeger |
| 3,858,578 A | 1/1975 | Milo |
| 3,865,105 A | 2/1975 | Lode |
| 3,867,728 A | 2/1975 | Stubstad et al. |
| 3,892,232 A | 7/1975 | Neufeld |
| 3,965,890 A | 6/1976 | Gauthier |
| 4,009,712 A | 3/1977 | Burstein et al. |
| 4,037,592 A | 7/1977 | Kronner |
| 4,047,524 A | 9/1977 | Hall |
| 4,074,542 A | 2/1978 | Hankosky et al. |
| 4,135,506 A | 1/1979 | Ulrich |
| 4,143,883 A | 3/1979 | Paynter |
| 4,165,746 A | 8/1979 | Burgin |
| 4,175,555 A | 11/1979 | Herbert |
| 4,237,875 A | 12/1980 | Termanini |
| 4,254,763 A | 3/1981 | McCready et al. |
| 4,289,123 A | 9/1981 | Dunn |
| 4,309,777 A | 1/1982 | Patil |
| 4,349,921 A | 9/1982 | Kuntz |
| 4,399,813 A | 8/1983 | Barber |
| 4,409,974 A | 10/1983 | Freedland |
| 4,432,358 A | 2/1984 | Fixel |
| 4,448,181 A | 5/1984 | Ishikawa et al. |
| 4,448,191 A | 5/1984 | Rodnyansky et al. |
| 4,488,543 A | 12/1984 | Tornier |
| 4,493,317 A | 1/1985 | Klaue |
| 4,494,535 A | 1/1985 | Haig |
| 4,503,848 A | 3/1985 | Caspar et al. |
| 4,545,374 A | 10/1985 | Jacobson et al. |
| 4,554,914 A | 11/1985 | Kapp et al. |
| 4,561,432 A | 12/1985 | Mazor |
| 4,569,662 A | 2/1986 | Dragan |
| 4,570,618 A | 2/1986 | Wu |
| 4,580,563 A | 4/1986 | Gross |
| 4,604,995 A | 8/1986 | Stephens et al. |
| 4,611,581 A | 9/1986 | Steffee |
| 4,611,582 A | 9/1986 | Duff |
| 4,612,920 A | 9/1986 | Lower |
| 4,632,101 A | 12/1986 | Freedland |
| 4,636,217 A | 1/1987 | Ogilvie et al. |
| 4,653,481 A | 3/1987 | Howland et al. |
| 4,655,462 A | 4/1987 | Balsells |
| 4,655,629 A | 4/1987 | Flaherty |
| 4,655,778 A | 4/1987 | Koeneman |
| 4,664,305 A | 5/1987 | Blake, III et al. |
| 4,697,582 A | 10/1987 | William |
| 4,699,076 A | 10/1987 | Curtis et al. |
| 4,702,230 A | 10/1987 | Pelta |
| 4,711,232 A | 12/1987 | Fischer et al. |
| 4,714,469 A | 12/1987 | Kenna |
| 4,722,331 A | 2/1988 | Fox |
| 4,747,394 A | 5/1988 | Watanabe |
| 4,747,395 A | 5/1988 | Brief |
| 4,756,711 A | 7/1988 | Mai et al. |
| 4,759,766 A | 7/1988 | Buettner-Janz et al. |
| 4,759,769 A | 7/1988 | Hedman et al. |
| 4,773,402 A | 9/1988 | Asher et al. |
| 4,787,908 A | 11/1988 | Wyss et al. |
| 4,790,303 A | 12/1988 | Steffee |
| 4,791,918 A | 12/1988 | Von Hasselbach |
| 4,794,918 A | 1/1989 | Wolter |
| 4,820,305 A | 4/1989 | Harms et al. |
| 4,834,757 A | 5/1989 | Brantigan |
| 4,867,404 A | 9/1989 | Harrington et al. |
| 4,874,389 A | 10/1989 | Downey |
| 4,877,020 A | 10/1989 | Vich |
| 4,881,525 A | 11/1989 | Williams |
| 4,887,595 A | 12/1989 | Heinig et al. |
| 4,898,156 A | 2/1990 | Gatturna et al. |
| 4,899,761 A | 2/1990 | Brown et al. |
| 4,903,692 A | 2/1990 | Reese |
| 4,904,110 A | 2/1990 | Klein |
| 4,907,577 A | 3/1990 | Wu |
| 4,911,718 A | 3/1990 | Lee et al. |
| 4,913,134 A * | 4/1990 | Luque ............... A61B 17/7059 606/289 |
| 4,932,975 A | 6/1990 | Main et al. |
| 4,934,352 A | 6/1990 | Sullivan, Jr. |
| 4,938,769 A | 7/1990 | Shaw |
| 4,944,757 A | 7/1990 | Martinez et al. |
| 4,946,378 A | 8/1990 | Hirayama et al. |
| 4,946,468 A | 8/1990 | Li |
| 4,949,707 A | 8/1990 | LeVahn et al. |
| 4,955,908 A | 9/1990 | Frey et al. |
| 4,957,497 A | 9/1990 | Hoogland et al. |
| 4,961,740 A | 10/1990 | Ray et al. |
| 4,963,152 A | 10/1990 | Hofmann et al. |
| 4,964,403 A | 10/1990 | Karas et al. |
| 4,969,886 A | 11/1990 | Cziffer et al. |
| 4,969,887 A | 11/1990 | Sodhi |
| 4,973,332 A | 11/1990 | Kummer |
| 4,997,123 A | 3/1991 | Backus et al. |
| 4,997,432 A | 3/1991 | Keller |
| 5,002,550 A | 3/1991 | Li |
| 5,002,576 A | 3/1991 | Fuhrmann et al. |
| 5,007,880 A | 4/1991 | Walker |
| 5,007,910 A | 4/1991 | Anapliotis et al. |
| 5,011,484 A | 4/1991 | Breard |
| 5,015,247 A | 5/1991 | Michelson |
| 5,026,373 A | 6/1991 | Ray et al. |
| 5,052,711 A | 10/1991 | Pirkey et al. |
| 5,055,104 A | 10/1991 | Ray |
| 5,061,271 A | 10/1991 | Van Zile |
| 5,071,437 A | 12/1991 | Steffee |
| 5,084,049 A | 1/1992 | Asher et al. |
| 5,087,266 A | 2/1992 | Connell et al. |
| 5,092,866 A | 3/1992 | Breard et al. |
| 5,092,893 A | 3/1992 | Smith |
| 5,098,435 A | 3/1992 | Stednitz et al. |
| 5,116,336 A | 5/1992 | Frigg |
| 5,122,130 A | 6/1992 | Keller |
| 5,122,131 A | 6/1992 | Tsou |
| 5,127,914 A | 7/1992 | Calderale et al. |
| 5,129,899 A | 7/1992 | Small et al. |
| 5,131,904 A | 7/1992 | Markoll |
| 5,133,717 A | 7/1992 | Chopin |

(56) References Cited

U.S. PATENT DOCUMENTS

| | | |
|---|---|---|
| 5,147,360 A | 9/1992 | Dubousset |
| 5,147,361 A | 9/1992 | Ojima et al. |
| 5,152,303 A | 10/1992 | Allen |
| 5,167,662 A | 12/1992 | Hayes et al. |
| 5,176,680 A | 1/1993 | Vignaud et al. |
| 5,180,381 A | 1/1993 | Aust et al. |
| 5,180,393 A | 1/1993 | Commarmond |
| 5,192,327 A | 3/1993 | Brantigan |
| 5,207,679 A | 5/1993 | Li |
| 5,222,954 A | 6/1993 | Baker et al. |
| 5,226,766 A | 7/1993 | Lasner |
| 5,234,431 A | 8/1993 | Keller |
| 5,234,432 A | 8/1993 | Brown |
| 5,234,447 A | 8/1993 | Kaster et al. |
| 5,236,460 A | 8/1993 | Barber |
| 5,242,444 A | 9/1993 | MacMillan |
| 5,242,445 A | 9/1993 | Ashman |
| 5,246,442 A | 9/1993 | Ashman et al. |
| 5,246,458 A | 9/1993 | Graham |
| 5,250,055 A | 10/1993 | Moore et al. |
| 5,252,016 A | 10/1993 | Schmid et al. |
| 5,254,118 A | 10/1993 | Mirkovic |
| 5,258,031 A | 11/1993 | Salib et al. |
| 5,261,907 A | 11/1993 | Vignaud et al. |
| 5,261,909 A | 11/1993 | Sutterlin et al. |
| 5,261,910 A | 11/1993 | Warden et al. |
| 5,261,911 A | 11/1993 | Carl |
| 5,261,914 A | 11/1993 | Warren |
| 5,275,600 A | 1/1994 | Allard et al. |
| 5,275,601 A | 1/1994 | Gogolewski et al. |
| 5,281,222 A | 1/1994 | Allard et al. |
| 5,282,801 A | 2/1994 | Sherman |
| 5,282,862 A | 2/1994 | Baker et al. |
| 5,290,312 A | 3/1994 | Kojimoto et al. |
| 5,300,074 A | 4/1994 | Frigg |
| 5,304,178 A | 4/1994 | Stahurski |
| 5,306,307 A | 4/1994 | Senter et al. |
| 5,312,405 A | 5/1994 | Korotko et al. |
| 5,324,290 A | 6/1994 | Zdeblick et al. |
| 5,324,292 A | 6/1994 | Meyers |
| 5,330,468 A | 7/1994 | Burkhart |
| 5,330,473 A | 7/1994 | Howland |
| 5,334,205 A | 8/1994 | Cain |
| 5,335,418 A | 8/1994 | Krivec |
| 5,336,225 A | 8/1994 | Zang |
| 5,336,226 A | 8/1994 | McDaniel et al. |
| 5,342,394 A | 8/1994 | Matsuno et al. |
| 5,344,421 A | 9/1994 | Crook |
| 5,344,422 A | 9/1994 | Frigg |
| 5,346,493 A | 9/1994 | Stahurski et al. |
| 5,350,380 A | 9/1994 | Goble et al. |
| 5,352,226 A | 10/1994 | Lin |
| 5,352,231 A | 10/1994 | Brumfield et al. |
| 5,354,292 A | 10/1994 | Braeuer et al. |
| 5,356,410 A | 10/1994 | Pennig |
| 5,358,289 A | 10/1994 | Banker et al. |
| 5,360,429 A | 11/1994 | Jeanson et al. |
| 5,360,431 A | 11/1994 | Puno et al. |
| 5,361,766 A | 11/1994 | Nichols et al. |
| 5,364,399 A | 11/1994 | Lowery et al. |
| 5,366,455 A | 11/1994 | Dove et al. |
| 5,370,697 A | 12/1994 | Baumgartner |
| 5,372,599 A | 12/1994 | Martins |
| 5,374,267 A | 12/1994 | Siegal |
| 5,375,823 A | 12/1994 | Navas |
| 5,380,324 A | 1/1995 | Mueller et al. |
| 5,385,583 A | 1/1995 | Cotrel |
| 5,387,176 A | 2/1995 | Markoll |
| 5,387,213 A | 2/1995 | Breard et al. |
| 5,395,371 A | 3/1995 | Miller et al. |
| 5,397,363 A | 3/1995 | Gelbard |
| 5,397,364 A | 3/1995 | Kozak et al. |
| 5,403,316 A | 4/1995 | Ashman |
| 5,413,576 A | 5/1995 | Rivard |
| 5,415,661 A | 5/1995 | Holmes |
| 5,417,712 A | 5/1995 | Whittaker et al. |
| 5,423,816 A | 6/1995 | Lin |
| 5,423,818 A | 6/1995 | Van et al. |
| 5,423,819 A | 6/1995 | Small et al. |
| 5,423,826 A | 6/1995 | Coates et al. |
| 5,425,772 A | 6/1995 | Brantigan |
| 5,425,773 A | 6/1995 | Boyd et al. |
| 5,427,418 A | 6/1995 | Watts |
| 5,429,639 A | 7/1995 | Judet |
| 5,431,658 A | 7/1995 | Moskovich |
| 5,437,669 A | 8/1995 | Yuan et al. |
| 5,437,670 A | 8/1995 | Sherman et al. |
| 5,437,672 A | 8/1995 | Alleyne |
| 5,437,674 A | 8/1995 | Worcel et al. |
| 5,439,339 A | 8/1995 | Batchelor |
| 5,439,463 A | 8/1995 | Lin |
| 5,443,467 A | 8/1995 | Biedermann et al. |
| 5,443,514 A | 8/1995 | Steffee |
| 5,449,257 A | 9/1995 | Giannuzzi |
| 5,453,073 A | 9/1995 | Markoll |
| 5,456,714 A | 10/1995 | Owen |
| 5,458,638 A | 10/1995 | Kuslich et al. |
| 5,466,237 A | 11/1995 | Byrd, III et al. |
| 5,468,241 A | 11/1995 | Metz-Stavenhagen et al. |
| 5,472,452 A | 12/1995 | Trott |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,478,342 A | 12/1995 | Kohrs |
| 5,480,401 A | 1/1996 | Navas |
| 5,484,437 A | 1/1996 | Michelson |
| 5,484,440 A | 1/1996 | Allard |
| 5,486,174 A | 1/1996 | Fournet-Fayard et al. |
| 5,486,176 A | 1/1996 | Hildebrand et al. |
| 5,487,742 A | 1/1996 | Cotrel |
| 5,489,307 A | 2/1996 | Kuslich et al. |
| 5,489,308 A | 2/1996 | Kuslich et al. |
| 5,490,750 A | 2/1996 | Gundy |
| 5,496,318 A | 3/1996 | Howland et al. |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,507,754 A | 4/1996 | Green et al. |
| 5,507,816 A | 4/1996 | Bullivant |
| 5,512,038 A | 4/1996 | O'Neal et al. |
| 5,514,180 A | 5/1996 | Heggeness et al. |
| 5,520,690 A | 5/1996 | Errico et al. |
| 5,522,899 A | 6/1996 | Michelson |
| 5,527,314 A | 6/1996 | Brumfield et al. |
| 5,531,747 A | 7/1996 | Ray |
| 5,531,751 A | 7/1996 | Schultheiss et al. |
| 5,534,001 A | 7/1996 | Schlapfer et al. |
| 5,534,002 A | 7/1996 | Brumfield et al. |
| 5,534,027 A | 7/1996 | Hodorek |
| 5,540,688 A | 7/1996 | Navas |
| 5,545,163 A | 8/1996 | Miller et al. |
| 5,545,164 A | 8/1996 | Howland |
| 5,545,165 A | 8/1996 | Biedermann et al. |
| 5,545,179 A | 8/1996 | Williamson |
| 5,549,607 A | 8/1996 | Olson et al. |
| 5,549,612 A | 8/1996 | Yapp et al. |
| 5,554,157 A | 9/1996 | Errico et al. |
| 5,556,431 A | 9/1996 | Büttner-Janz |
| 5,558,674 A | 9/1996 | Heggeness et al. |
| 5,562,660 A | 10/1996 | Grob |
| 5,562,661 A | 10/1996 | Yoshimi et al. |
| 5,562,662 A | 10/1996 | Brumfield et al. |
| 5,562,663 A | 10/1996 | Wisnewski et al. |
| 5,562,737 A | 10/1996 | Graf |
| 5,562,738 A | 10/1996 | Boyd et al. |
| 5,569,247 A | 10/1996 | Morrison |
| 5,569,248 A | 10/1996 | Mathews |
| 5,569,250 A | 10/1996 | Sarver et al. |
| 5,569,251 A | 10/1996 | Baker et al. |
| 5,569,252 A | 10/1996 | Justin et al. |
| 5,575,792 A | 11/1996 | Errico et al. |
| 5,578,033 A | 11/1996 | Errico et al. |

(56) References Cited

U.S. PATENT DOCUMENTS

| | | |
|---|---|---|
| 5,578,034 A | 11/1996 | Estes |
| 5,582,612 A | 12/1996 | Lin |
| 5,584,833 A | 12/1996 | Fournet-Fayard et al. |
| 5,584,834 A | 12/1996 | Errico et al. |
| 5,586,984 A | 12/1996 | Errico et al. |
| 5,591,166 A | 1/1997 | Bernhardt et al. |
| 5,599,279 A | 2/1997 | Slotman et al. |
| 5,601,553 A | 2/1997 | Trebing et al. |
| 5,603,714 A | 2/1997 | Kaneda et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,609,634 A | 3/1997 | Voydeville |
| 5,609,635 A | 3/1997 | Michelson |
| 5,609,636 A | 3/1997 | Kohrs et al. |
| 5,609,637 A | 3/1997 | Biedermann et al. |
| 5,611,800 A | 3/1997 | Davis et al. |
| 5,616,142 A | 4/1997 | Yuan et al. |
| 5,620,169 A | 4/1997 | Payne |
| 5,620,443 A | 4/1997 | Gertzbein et al. |
| 5,628,740 A | 5/1997 | Mullane |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schaefer et al. |
| 5,643,262 A | 7/1997 | Metz-Stavenhagen et al. |
| 5,643,321 A | 7/1997 | McDevitt |
| 5,645,544 A | 7/1997 | Tai et al. |
| 5,645,599 A | 7/1997 | Samani |
| 5,647,873 A | 7/1997 | Errico et al. |
| 5,649,931 A | 7/1997 | Bryant et al. |
| 5,653,763 A | 8/1997 | Errico et al. |
| 5,662,652 A | 9/1997 | Schaefer et al. |
| 5,662,653 A | 9/1997 | Songer et al. |
| 5,665,049 A | 9/1997 | Markoll |
| 5,667,513 A | 9/1997 | Torrie et al. |
| 5,669,868 A | 9/1997 | Markoll |
| 5,669,909 A | 9/1997 | Zdeblick et al. |
| 5,669,911 A | 9/1997 | Errico et al. |
| 5,669,912 A | 9/1997 | Spetzler |
| 5,672,175 A | 9/1997 | Martin |
| 5,672,176 A | 9/1997 | Biedermann et al. |
| 5,674,294 A | 10/1997 | Bainville et al. |
| 5,674,296 A | 10/1997 | Bryan et al. |
| 5,676,666 A | 10/1997 | Oxland et al. |
| 5,676,697 A | 10/1997 | McDonald |
| 5,676,701 A | 10/1997 | Yuan et al. |
| 5,676,703 A | 10/1997 | Gelbard |
| 5,681,311 A | 10/1997 | Foley et al. |
| 5,681,312 A | 10/1997 | Yuan et al. |
| 5,681,313 A | 10/1997 | Diez |
| 5,681,319 A | 10/1997 | Biedermann et al. |
| 5,683,390 A | 11/1997 | Metz-Stavenhagen et al. |
| 5,683,391 A | 11/1997 | Boyd |
| 5,683,392 A | 11/1997 | Richelsoph et al. |
| 5,683,394 A | 11/1997 | Rinner |
| 5,683,464 A | 11/1997 | Wagner et al. |
| 5,688,275 A | 11/1997 | Koros et al. |
| 5,690,630 A | 11/1997 | Errico et al. |
| 5,697,929 A | 12/1997 | Mellinger |
| 5,702,451 A | 12/1997 | Biedermann et al. |
| 5,704,936 A | 1/1998 | Mazel |
| 5,707,372 A | 1/1998 | Errico et al. |
| 5,709,686 A | 1/1998 | Talos et al. |
| 5,711,709 A | 1/1998 | McCoy |
| 5,713,672 A | 2/1998 | Lu |
| 5,713,898 A | 2/1998 | Stuecker et al. |
| 5,713,899 A | 2/1998 | Marnay et al. |
| 5,713,900 A | 2/1998 | Benzel et al. |
| 5,713,904 A | 2/1998 | Errico et al. |
| 5,716,356 A | 2/1998 | Biedermann et al. |
| 5,716,357 A | 2/1998 | Rogozinski |
| 5,720,751 A | 2/1998 | Jackson |
| 5,722,976 A | 3/1998 | Brown |
| 5,722,977 A | 3/1998 | Wilhelmy |
| 5,723,013 A | 3/1998 | Jeanson et al. |
| 5,725,527 A | 3/1998 | Biedermann et al. |
| 5,725,528 A | 3/1998 | Errico et al. |
| 5,725,582 A | 3/1998 | Bevan et al. |
| 5,728,046 A | 3/1998 | Mayer et al. |
| 5,728,098 A | 3/1998 | Sherman et al. |
| 5,733,284 A | 3/1998 | Martin |
| 5,733,285 A | 3/1998 | Errico et al. |
| 5,733,286 A | 3/1998 | Errico et al. |
| 5,733,290 A | 3/1998 | McCue et al. |
| 5,735,853 A | 4/1998 | Olerud |
| 5,738,685 A | 4/1998 | Halm et al. |
| 5,741,254 A | 4/1998 | Henry et al. |
| 5,741,261 A | 4/1998 | Moskovitz et al. |
| 5,746,743 A | 5/1998 | Greenberg |
| 5,749,916 A | 5/1998 | Richelsoph |
| 5,749,968 A | 5/1998 | Melanson et al. |
| 5,752,957 A | 5/1998 | Ralph et al. |
| 5,755,660 A | 5/1998 | Tyagi |
| 5,755,732 A | 5/1998 | Green et al. |
| 5,766,252 A | 6/1998 | Henry et al. |
| 5,772,583 A | 6/1998 | Wright et al. |
| 5,776,135 A | 7/1998 | Errico et al. |
| 5,776,199 A | 7/1998 | Michelson |
| 5,782,830 A | 7/1998 | Farris |
| 5,782,832 A | 7/1998 | Larsen et al. |
| 5,782,833 A | 7/1998 | Haider |
| 5,782,919 A | 7/1998 | Zdeblick et al. |
| 5,792,044 A | 8/1998 | Foley et al. |
| 5,795,289 A | 8/1998 | Wyttenbach |
| 5,795,291 A | 8/1998 | Koros et al. |
| 5,795,584 A | 8/1998 | Totakura et al. |
| 5,797,911 A | 8/1998 | Sherman et al. |
| 5,800,433 A | 9/1998 | Benzel et al. |
| 5,800,435 A | 9/1998 | Errico et al. |
| 5,800,547 A | 9/1998 | Schaefer et al. |
| 5,807,403 A | 9/1998 | Beyar et al. |
| 5,810,818 A | 9/1998 | Errico et al. |
| 5,810,819 A | 9/1998 | Errico et al. |
| 5,817,094 A | 10/1998 | Errico et al. |
| 5,833,418 A | 11/1998 | Shoji |
| 5,836,948 A | 11/1998 | Zucherman et al. |
| 5,842,966 A | 12/1998 | Markoll |
| 5,846,192 A | 12/1998 | Teixido |
| 5,860,977 A | 1/1999 | Zucherman et al. |
| 5,863,293 A | 1/1999 | Richelsoph |
| 5,865,848 A | 2/1999 | Baker |
| 5,873,878 A | 2/1999 | Harms et al. |
| 5,876,402 A | 3/1999 | Errico et al. |
| 5,876,404 A | 3/1999 | Zucherman et al. |
| 5,879,350 A | 3/1999 | Sherman et al. |
| 5,879,351 A | 3/1999 | Viart |
| 5,882,298 A | 3/1999 | Sharratt |
| 5,882,350 A | 3/1999 | Ralph et al. |
| 5,882,351 A | 3/1999 | Fox |
| 5,884,702 A | 3/1999 | Yokley et al. |
| 5,885,286 A | 3/1999 | Sherman et al. |
| 5,888,197 A | 3/1999 | Mulac et al. |
| 5,888,222 A | 3/1999 | Coates et al. |
| 5,888,224 A | 3/1999 | Beckers et al. |
| 5,888,226 A | 3/1999 | Rogozinski |
| 5,890,271 A | 4/1999 | Bromley et al. |
| 5,891,145 A | 4/1999 | Morrison et al. |
| 5,893,831 A | 4/1999 | Koros et al. |
| 5,899,425 A | 5/1999 | Corey, Jr. et al. |
| 5,899,904 A | 5/1999 | Errico et al. |
| 5,899,905 A | 5/1999 | Errico et al. |
| 5,902,231 A | 5/1999 | Foley et al. |
| 5,902,233 A | 5/1999 | Farley et al. |
| 5,902,304 A | 5/1999 | Walker et al. |
| 5,904,683 A | 5/1999 | Pohndorf et al. |
| RE36,221 E | 6/1999 | Breard |
| 5,908,382 A | 6/1999 | Koros et al. |
| 5,910,141 A | 6/1999 | Morrison et al. |
| 5,928,139 A | 7/1999 | Koros et al. |
| 5,928,231 A | 7/1999 | Klein et al. |

(56) References Cited

U.S. PATENT DOCUMENTS

| | | |
|---|---|---|
| 5,928,233 A | 7/1999 | Apfelbaum et al. |
| 5,931,777 A | 8/1999 | Sava |
| 5,938,663 A | 8/1999 | Petreto |
| 5,941,885 A | 8/1999 | Jackson |
| 5,944,465 A | 8/1999 | Janitzki |
| 5,944,658 A | 8/1999 | Koros et al. |
| 5,947,967 A | 9/1999 | Barker |
| 5,947,970 A | 9/1999 | Schmelzeisen et al. |
| 5,951,553 A | 9/1999 | Betz et al. |
| 5,951,558 A | 9/1999 | Fiz |
| 5,954,722 A | 9/1999 | Bono |
| 5,954,725 A | 9/1999 | Sherman et al. |
| 5,961,516 A | 10/1999 | Graf |
| 5,961,517 A | 10/1999 | Biedermann et al. |
| 5,961,518 A | 10/1999 | Errico et al. |
| 5,964,760 A | 10/1999 | Richelsoph |
| 5,964,762 A | 10/1999 | Biedermann et al. |
| 5,964,763 A | 10/1999 | Incavo et al. |
| 5,967,970 A | 10/1999 | Cowan et al. |
| 5,967,972 A | 10/1999 | Santilli et al. |
| 5,971,987 A | 10/1999 | Huxel et al. |
| 5,976,135 A | 11/1999 | Sherman et al. |
| 5,976,140 A | 11/1999 | Haas |
| 5,976,146 A | 11/1999 | Ogawa et al. |
| 5,976,186 A | 11/1999 | Bao et al. |
| 5,980,522 A | 11/1999 | Koros et al. |
| 5,984,865 A | 11/1999 | Farley et al. |
| 5,984,923 A | 11/1999 | Breard |
| 5,984,967 A | 11/1999 | Zdeblick et al. |
| 5,993,385 A | 11/1999 | Johnston et al. |
| 5,993,449 A | 11/1999 | Schlaepfer et al. |
| 5,997,539 A | 12/1999 | Errico et al. |
| 6,001,098 A | 12/1999 | Metz-Stavenhagen et al. |
| 6,001,130 A | 12/1999 | Bryan et al. |
| 6,004,326 A | 12/1999 | Castro et al. |
| 6,004,349 A | 12/1999 | Jackson |
| 6,010,503 A | 1/2000 | Richelsoph et al. |
| 6,010,692 A | 1/2000 | Goldberg et al. |
| 6,016,727 A | 1/2000 | Morgan |
| 6,017,342 A | 1/2000 | Rinner |
| 6,017,344 A | 1/2000 | Errico et al. |
| 6,019,759 A | 2/2000 | Rogozinski |
| 6,019,792 A | 2/2000 | Cauthen |
| 6,022,350 A | 2/2000 | Ganem |
| 6,022,376 A | 2/2000 | Assell et al. |
| 6,030,388 A | 2/2000 | Yoshimi et al. |
| 6,033,170 A | 3/2000 | Gold |
| 6,033,406 A | 3/2000 | Mathews |
| 6,033,436 A | 3/2000 | Steinke et al. |
| 6,039,740 A | 3/2000 | Olerud |
| 6,039,761 A | 3/2000 | Li et al. |
| D422,705 S | 4/2000 | Koros et al. |
| 6,045,555 A | 4/2000 | Smith et al. |
| 6,045,579 A | 4/2000 | Hochshuler et al. |
| 6,048,302 A | 4/2000 | Markoll |
| 6,048,342 A | 4/2000 | Zucherman et al. |
| 6,048,343 A | 4/2000 | Mathis et al. |
| 6,050,997 A | 4/2000 | Mullane |
| 6,053,917 A | 4/2000 | Sherman et al. |
| 6,059,785 A | 5/2000 | Schavan et al. |
| 6,059,786 A | 5/2000 | Jackson |
| 6,063,089 A | 5/2000 | Errico et al. |
| 6,063,090 A | 5/2000 | Schlaepfer |
| 6,066,174 A | 5/2000 | Farris |
| 6,066,175 A | 5/2000 | Henderson et al. |
| 6,068,630 A | 5/2000 | Zucherman et al. |
| 6,071,310 A | 6/2000 | Picha et al. |
| 6,074,343 A | 6/2000 | Nathanson et al. |
| 6,074,390 A | 6/2000 | Zucherman et al. |
| 6,074,391 A | 6/2000 | Metz-Stavenhagen et al. |
| 6,077,262 A | 6/2000 | Schlaeper et al. |
| 6,080,193 A | 6/2000 | Hochshuler et al. |
| 6,083,224 A | 7/2000 | Gertzbein et al. |
| 6,083,225 A | 7/2000 | Winslow et al. |
| 6,083,624 A | 7/2000 | Hiura |
| 6,086,588 A | 7/2000 | Ameil et al. |
| 6,086,589 A | 7/2000 | Kuslich et al. |
| 6,086,613 A | 7/2000 | Camino et al. |
| 6,090,110 A | 7/2000 | Metz-Stavenhagen |
| 6,090,111 A | 7/2000 | Nichols |
| 6,090,113 A | 7/2000 | Le et al. |
| 6,093,205 A | 7/2000 | McLeod et al. |
| 6,096,060 A | 8/2000 | Fitts et al. |
| 6,099,528 A | 8/2000 | Saurat |
| 6,099,531 A | 8/2000 | Bonutti |
| 6,102,912 A | 8/2000 | Cazin et al. |
| 6,102,913 A | 8/2000 | Jackson |
| 6,110,172 A | 8/2000 | Jackson |
| 6,110,173 A | 8/2000 | Thomas, Jr. |
| 6,111,164 A | 8/2000 | Rainey et al. |
| 6,113,599 A | 9/2000 | Landsberger |
| 6,113,601 A | 9/2000 | Tatar |
| 6,113,638 A | 9/2000 | Williams et al. |
| 6,117,135 A | 9/2000 | Schlaepfer |
| 6,117,137 A | 9/2000 | Halm et al. |
| 6,119,631 A | 9/2000 | Markoll |
| 6,120,502 A * | 9/2000 | Michelson ......... A61B 17/1671 606/247 |
| 6,123,706 A | 9/2000 | Lange |
| 6,123,707 A | 9/2000 | Wagner |
| 6,126,689 A | 10/2000 | Brett |
| 6,132,370 A | 10/2000 | Furnish et al. |
| 6,132,430 A | 10/2000 | Wagner |
| 6,132,431 A | 10/2000 | Nilsson et al. |
| 6,132,432 A | 10/2000 | Richelsoph |
| 6,132,434 A | 10/2000 | Sherman et al. |
| 6,132,464 A | 10/2000 | Martin |
| 6,136,000 A | 10/2000 | Louis et al. |
| 6,136,002 A | 10/2000 | Shih et al. |
| 6,139,316 A | 10/2000 | Sachdeva et al. |
| 6,139,493 A | 10/2000 | Koros et al. |
| 6,139,549 A | 10/2000 | Keller |
| 6,143,032 A | 11/2000 | Schafer et al. |
| 6,146,044 A | 11/2000 | Calvet |
| 6,146,383 A | 11/2000 | Studer et al. |
| 6,146,422 A | 11/2000 | Lawson |
| 6,149,650 A | 11/2000 | Michelson |
| 6,152,927 A | 11/2000 | Farris et al. |
| 6,156,037 A | 12/2000 | LeHuec et al. |
| 6,159,210 A | 12/2000 | Voor |
| 6,159,211 A | 12/2000 | Boriani et al. |
| 6,159,215 A | 12/2000 | Urbahns et al. |
| 6,159,244 A | 12/2000 | Suddaby |
| 6,162,252 A | 12/2000 | Kuras et al. |
| 6,174,311 B1 | 1/2001 | Branch et al. |
| 6,176,882 B1 | 1/2001 | Biedermann et al. |
| 6,179,838 B1 | 1/2001 | Fiz |
| 6,179,873 B1 | 1/2001 | Zientek |
| 6,179,874 B1 | 1/2001 | Cauthen |
| 6,183,472 B1 | 2/2001 | Lutz |
| 6,183,473 B1 | 2/2001 | Ashman |
| 6,186,005 B1 | 2/2001 | Leidl |
| 6,186,718 B1 | 2/2001 | Fogard |
| 6,187,005 B1 | 2/2001 | Brace et al. |
| 6,193,720 B1 | 2/2001 | Yuan et al. |
| 6,193,721 B1 | 2/2001 | Michelson |
| 6,193,757 B1 | 2/2001 | Foley et al. |
| 6,197,033 B1 | 3/2001 | Haid, Jr. et al. |
| 6,200,322 B1 | 3/2001 | Branch et al. |
| 6,206,826 B1 | 3/2001 | Mathews et al. |
| 6,206,879 B1 | 3/2001 | Marnay et al. |
| 6,206,922 B1 | 3/2001 | Zdeblick et al. |
| 6,206,923 B1 | 3/2001 | Boyd et al. |
| D440,311 S | 4/2001 | Michelson |
| 6,210,376 B1 | 4/2001 | Grayson |
| 6,210,412 B1 | 4/2001 | Michelson |
| 6,210,413 B1 | 4/2001 | Justis et al. |
| 6,214,005 B1 | 4/2001 | Benzel et al. |
| 6,214,012 B1 | 4/2001 | Karpman et al. |
| 6,221,077 B1 | 4/2001 | Rinner et al. |
| RE37,161 E | 5/2001 | Michelson |
| 6,224,545 B1 | 5/2001 | Cocchia et al. |
| 6,224,595 B1 | 5/2001 | Michelson |
| 6,224,596 B1 | 5/2001 | Jackson |

(56) References Cited

U.S. PATENT DOCUMENTS

| | | |
|---|---|---|
| 6,224,598 B1 | 5/2001 | Jackson |
| 6,224,602 B1 | 5/2001 | Hayes |
| 6,224,607 B1 | 5/2001 | Michelson |
| 6,226,548 B1 | 5/2001 | Foley et al. |
| 6,228,022 B1 | 5/2001 | Friesem et al. |
| 6,228,085 B1 | 5/2001 | Theken et al. |
| 6,231,575 B1 | 5/2001 | Krag |
| 6,234,705 B1 | 5/2001 | Troxell |
| 6,235,028 B1 | 5/2001 | Brumfield et al. |
| 6,235,034 B1 | 5/2001 | Bray |
| 6,235,726 B1 | 5/2001 | Burns et al. |
| 6,238,396 B1 | 5/2001 | Lombardo |
| 6,241,729 B1 | 6/2001 | Estes et al. |
| 6,241,730 B1 | 6/2001 | Alby |
| 6,241,769 B1 | 6/2001 | Nicholson et al. |
| 6,241,770 B1 | 6/2001 | Michelson |
| 6,245,072 B1 | 6/2001 | Zdeblick et al. |
| 6,245,108 B1 | 6/2001 | Biscup |
| 6,248,104 B1 | 6/2001 | Chopin et al. |
| 6,248,105 B1 | 6/2001 | Schläpfer et al. |
| 6,248,106 B1 | 6/2001 | Ferree |
| 6,248,107 B1 | 6/2001 | Foley et al. |
| 6,248,110 B1 | 6/2001 | Reiley et al. |
| 6,250,984 B1 | 6/2001 | Jin et al. |
| 6,251,112 B1 | 6/2001 | Jackson |
| 6,251,140 B1 | 6/2001 | Marino et al. |
| 6,254,146 B1 | 7/2001 | Church |
| 6,254,602 B1 | 7/2001 | Justis |
| 6,254,603 B1 | 7/2001 | Gertzbein et al. |
| 6,258,089 B1 | 7/2001 | Campbell et al. |
| 6,258,125 B1 | 7/2001 | Paul et al. |
| 6,261,287 B1 | 7/2001 | Metz-Stavenhagen |
| 6,261,291 B1 | 7/2001 | Talaber et al. |
| 6,264,656 B1 | 7/2001 | Michelson |
| 6,267,764 B1 | 7/2001 | Elberg |
| 6,267,765 B1 | 7/2001 | Taylor et al. |
| 6,270,498 B1 | 8/2001 | Michelson |
| 6,273,888 B1 | 8/2001 | Justis |
| 6,273,889 B1 | 8/2001 | Richelsoph |
| 6,277,122 B1 | 8/2001 | McGahan et al. |
| 6,277,149 B1 | 8/2001 | Boyle et al. |
| 6,280,442 B1 | 8/2001 | Barker et al. |
| 6,280,445 B1 | 8/2001 | Morrison et al. |
| D448,081 S | 9/2001 | Koros et al. |
| 6,283,967 B1 | 9/2001 | Troxell et al. |
| 6,287,308 B1 | 9/2001 | Betz et al. |
| 6,287,309 B1 | 9/2001 | Baccelli et al. |
| 6,287,311 B1 | 9/2001 | Sherman et al. |
| 6,290,703 B1 | 9/2001 | Ganem |
| 6,293,949 B1 | 9/2001 | Justis et al. |
| 6,294,202 B1 | 9/2001 | Burns et al. |
| D449,692 S | 10/2001 | Michelson |
| 6,296,642 B1 | 10/2001 | Morrison et al. |
| 6,296,643 B1 | 10/2001 | Hopf et al. |
| 6,296,664 B1 | 10/2001 | Middleton |
| 6,299,613 B1 | 10/2001 | Ogilvie et al. |
| 6,302,843 B1 | 10/2001 | Lees et al. |
| 6,302,888 B1 | 10/2001 | Mellinger et al. |
| 6,302,914 B1 | 10/2001 | Michelson |
| 6,304,178 B1 | 10/2001 | Hayashida |
| 6,306,136 B1 | 10/2001 | Baccelli |
| 6,306,137 B2 | 10/2001 | Troxell |
| 6,306,170 B2 | 10/2001 | Ray |
| 6,309,391 B1 | 10/2001 | Crandall et al. |
| 6,312,431 B1 | 11/2001 | Asfora |
| 6,315,564 B1 | 11/2001 | Levisman |
| 6,315,779 B1 | 11/2001 | Morrison et al. |
| 6,317,957 B1 | 11/2001 | Gregor et al. |
| 6,319,002 B1 | 11/2001 | Pond |
| 6,319,257 B1 | 11/2001 | Carignan et al. |
| 6,322,500 B1 | 11/2001 | Sikora et al. |
| RE37,479 E | 12/2001 | Kuslich |
| 6,331,179 B1 | 12/2001 | Freid et al. |
| 6,332,882 B1 | 12/2001 | Zucherman et al. |
| 6,340,345 B1 | 1/2002 | Lees et al. |
| 6,342,074 B1 | 1/2002 | Simpson |
| 6,344,057 B1 | 2/2002 | Rabbe et al. |
| 6,348,058 B1 | 2/2002 | Melkent et al. |
| 6,348,071 B1 | 2/2002 | Steffee et al. |
| 6,350,283 B1 | 2/2002 | Michelson |
| 6,355,038 B1 | 3/2002 | Pisharodi |
| 6,355,039 B1 | 3/2002 | Troussel et al. |
| 6,355,040 B1 | 3/2002 | Richelsoph et al. |
| 6,360,750 B1 | 3/2002 | Gerber et al. |
| 6,361,258 B1 | 3/2002 | Heesch |
| RE37,665 E | 4/2002 | Ralph |
| 6,364,880 B1 | 4/2002 | Michelson |
| 6,364,881 B1 | 4/2002 | Apgar et al. |
| 6,364,883 B1 | 4/2002 | Santilli |
| 6,368,320 B1 | 4/2002 | Le et al. |
| 6,368,321 B1 | 4/2002 | Jackson |
| 6,368,350 B1 | 4/2002 | Erickson et al. |
| 6,371,957 B1 | 4/2002 | Amrein et al. |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,375,681 B1 | 4/2002 | Truscott |
| 6,379,355 B1 | 4/2002 | Zucherman et al. |
| 6,379,357 B1 | 4/2002 | Bernstein et al. |
| 6,387,130 B1 | 5/2002 | Stone et al. |
| 6,389,391 B1 | 5/2002 | Terauchi |
| 6,395,031 B1 | 5/2002 | Foley et al. |
| 6,395,035 B2 | 5/2002 | Bresina et al. |
| 6,398,783 B1 | 6/2002 | Michelson |
| 6,402,749 B1 | 6/2002 | Ashman |
| 6,402,750 B1 | 6/2002 | Atkinson et al. |
| 6,402,751 B1 | 6/2002 | Hoeck et al. |
| 6,402,752 B2 | 6/2002 | Schaffler-Wachter et al. |
| 6,402,756 B1 | 6/2002 | Ralph et al. |
| 6,402,757 B1 | 6/2002 | Moore, III et al. |
| 6,402,785 B1 | 6/2002 | Zdeblick et al. |
| 6,406,478 B1 | 6/2002 | Kuo |
| 6,409,765 B1 | 6/2002 | Bianchi et al. |
| 6,412,999 B1 | 7/2002 | Pierpont |
| 6,413,258 B1 | 7/2002 | Bernhardt, Jr. |
| 6,413,259 B1 | 7/2002 | Lyons et al. |
| 6,413,278 B1 | 7/2002 | Marchosky |
| 6,416,465 B2 | 7/2002 | Brau |
| 6,416,515 B1 | 7/2002 | Wagner |
| 6,419,676 B1 | 7/2002 | Zucherman et al. |
| 6,419,677 B2 | 7/2002 | Zucherman et al. |
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van et al. |
| 6,428,542 B1 | 8/2002 | Michelson |
| 6,428,576 B1 | 8/2002 | Haldimann |
| 6,432,108 B1 | 8/2002 | Burgess et al. |
| 6,432,140 B1 | 8/2002 | Lin |
| 6,440,133 B1 | 8/2002 | Beale et al. |
| 6,440,137 B1 | 8/2002 | Horvath et al. |
| 6,440,139 B2 | 8/2002 | Michelson |
| 6,440,168 B1 | 8/2002 | Cauthen |
| 6,440,169 B1 | 8/2002 | Elberg et al. |
| 6,440,170 B1 | 8/2002 | Jackson |
| 6,443,956 B1 | 9/2002 | Ray |
| 6,447,440 B1 | 9/2002 | Markoll |
| 6,447,443 B1 | 9/2002 | Keogh et al. |
| 6,447,547 B1 | 9/2002 | Michelson |
| 6,447,548 B1 | 9/2002 | Ralph et al. |
| 6,451,019 B1 | 9/2002 | Zucherman et al. |
| 6,451,020 B1 | 9/2002 | Zucherman et al. |
| 6,451,021 B1 | 9/2002 | Ralph et al. |
| 6,454,769 B2 | 9/2002 | Wagner et al. |
| 6,454,771 B1 | 9/2002 | Michelson |
| 6,454,773 B1 | 9/2002 | Sherman et al. |
| 6,458,159 B1 | 10/2002 | Thalgott |
| 6,461,358 B1 | 10/2002 | Faccioli et al. |
| 6,461,359 B1 | 10/2002 | Tribus et al. |
| 6,468,310 B1 | 10/2002 | Ralph et al. |
| 6,471,703 B1 | 10/2002 | Ashman |
| 6,471,704 B2 | 10/2002 | Gertzbein et al. |
| 6,471,705 B1 | 10/2002 | Biedermann et al. |

(56) References Cited

U.S. PATENT DOCUMENTS

| | | |
|---|---|---|
| 6,471,724 B2 | 10/2002 | Zdeblick et al. |
| 6,475,218 B2 | 11/2002 | Gournay et al. |
| 6,478,796 B2 | 11/2002 | Zucherman et al. |
| 6,478,798 B1 | 11/2002 | Howland |
| 6,478,800 B1 | 11/2002 | Fraser et al. |
| 6,478,801 B1 | 11/2002 | Ralph et al. |
| 6,482,234 B1 | 11/2002 | Weber et al. |
| 6,485,491 B1 | 11/2002 | Farris et al. |
| 6,485,492 B1 | 11/2002 | Halm et al. |
| 6,485,494 B1 | 11/2002 | Haider |
| 6,485,517 B1 | 11/2002 | Michelson |
| 6,485,518 B1 | 11/2002 | Cornwall et al. |
| 6,488,681 B2 | 12/2002 | Martin et al. |
| 6,497,726 B1 | 12/2002 | Carter et al. |
| 6,500,205 B1 | 12/2002 | Michelson |
| 6,503,250 B2 | 1/2003 | Paul |
| 6,508,818 B2 | 1/2003 | Steiner et al. |
| 6,508,839 B1 | 1/2003 | Lambrecht et al. |
| 6,511,484 B2 | 1/2003 | Torode et al. |
| 6,514,256 B2 | 2/2003 | Zucherman et al. |
| 6,514,260 B1 | 2/2003 | Zdeblick et al. |
| 6,517,580 B1 | 2/2003 | Ramadan et al. |
| 6,520,962 B1 | 2/2003 | Taylor et al. |
| 6,520,967 B1 | 2/2003 | Cauthen |
| 6,520,996 B1 | 2/2003 | Manasas et al. |
| 6,521,223 B1 | 2/2003 | Calias et al. |
| 6,524,233 B2 | 2/2003 | Markoll |
| 6,524,238 B2 | 2/2003 | Velikaris et al. |
| 6,524,312 B2 | 2/2003 | Landry et al. |
| 6,524,315 B1 | 2/2003 | Selvitelli et al. |
| 6,527,773 B1 | 3/2003 | Lin et al. |
| 6,527,803 B1 | 3/2003 | Crozet et al. |
| 6,527,804 B1 | 3/2003 | Gauchet et al. |
| 6,527,806 B2 | 3/2003 | Ralph et al. |
| 6,530,929 B1 | 3/2003 | Justis et al. |
| 6,531,146 B2 | 3/2003 | Calhoun et al. |
| 6,533,786 B1 | 3/2003 | Needham et al. |
| 6,537,276 B2 | 3/2003 | Metz-Stavenhagen |
| 6,537,279 B1 | 3/2003 | Michelson |
| 6,538,262 B1 | 3/2003 | Crespi et al. |
| 6,539,826 B2 | 4/2003 | Oesterle et al. |
| 6,540,749 B2 | 4/2003 | Schafer et al. |
| 6,540,785 B1 | 4/2003 | Gill et al. |
| 6,547,790 B2 | 4/2003 | Harkey et al. |
| 6,547,795 B2 | 4/2003 | Schneiderman |
| 6,551,242 B1 | 4/2003 | Furnish et al. |
| 6,551,320 B2 | 4/2003 | Lieberman |
| 6,551,322 B1 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,554,863 B2 | 4/2003 | Paul et al. |
| 6,558,386 B1 | 5/2003 | Cragg |
| 6,558,387 B2 | 5/2003 | Errico et al. |
| 6,558,390 B2 | 5/2003 | Cragg |
| 6,558,423 B1 | 5/2003 | Michelson |
| 6,558,424 B2 | 5/2003 | Thalgott |
| 6,562,038 B1 | 5/2003 | Morrison |
| 6,562,040 B1 | 5/2003 | Wagner |
| 6,562,046 B2 | 5/2003 | Sasso |
| 6,562,074 B2 | 5/2003 | Gerbec et al. |
| 6,565,565 B1 | 5/2003 | Yuan et al. |
| 6,565,567 B1 | 5/2003 | Haider |
| 6,565,571 B1 | 5/2003 | Jackowski et al. |
| 6,565,605 B2 | 5/2003 | Goble et al. |
| 6,569,168 B2 | 5/2003 | Lin |
| 6,572,618 B1 | 6/2003 | Morrison |
| 6,575,899 B1 | 6/2003 | Foley et al. |
| 6,575,981 B1 | 6/2003 | Boyd et al. |
| 6,576,016 B1 | 6/2003 | Hochshuler et al. |
| 6,579,291 B1 | 6/2003 | Keith et al. |
| 6,579,319 B2 | 6/2003 | Goble et al. |
| 6,582,431 B1 | 6/2003 | Ray |
| 6,582,433 B2 | 6/2003 | Yun |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,589,243 B1 | 7/2003 | Viart et al. |
| 6,592,585 B2 | 7/2003 | Lee et al. |
| 6,592,624 B1 | 7/2003 | Fraser et al. |
| 6,595,992 B1 | 7/2003 | Wagner et al. |
| 6,595,993 B2 | 7/2003 | Donno et al. |
| 6,595,995 B2 | 7/2003 | Zdeblick et al. |
| 6,599,240 B2 | 7/2003 | Puchovsky et al. |
| 6,599,290 B2 | 7/2003 | Bailey et al. |
| 6,599,292 B1 | 7/2003 | Ray |
| 6,599,294 B2 | 7/2003 | Fuss et al. |
| 6,599,295 B1 | 7/2003 | Tornier et al. |
| 6,599,320 B1 | 7/2003 | Kuslich et al. |
| 6,599,321 B2 | 7/2003 | Hyde et al. |
| 6,602,254 B2 | 8/2003 | Gertzbein et al. |
| 6,602,255 B1 | 8/2003 | Campbell et al. |
| 6,602,256 B1 | 8/2003 | Hayes |
| 6,602,257 B1 | 8/2003 | Thramann |
| 6,605,089 B1 | 8/2003 | Michelson |
| 6,607,530 B1 | 8/2003 | Carl et al. |
| 6,607,558 B2 | 8/2003 | Kuras |
| 6,610,063 B2 | 8/2003 | Kumar et al. |
| 6,610,089 B1 | 8/2003 | Liu et al. |
| 6,610,093 B1 | 8/2003 | Pisharodi |
| 6,613,050 B1 | 9/2003 | Wagner et al. |
| 6,613,089 B1 | 9/2003 | Estes et al. |
| 6,613,091 B1 | 9/2003 | Zdeblick et al. |
| 6,613,278 B1 | 9/2003 | Mills et al. |
| 6,616,664 B2 | 9/2003 | Walulik et al. |
| 6,616,665 B2 | 9/2003 | Grafton et al. |
| 6,616,667 B1 | 9/2003 | Steiger et al. |
| 6,616,669 B2 | 9/2003 | Ogilvie et al. |
| 6,616,695 B1 | 9/2003 | Crozet et al. |
| 6,620,163 B1 | 9/2003 | Michelson |
| 6,622,344 B1 | 9/2003 | Lu |
| 6,623,485 B2 | 9/2003 | Doubler et al. |
| 6,626,347 B2 | 9/2003 | Ng |
| 6,626,904 B1 | 9/2003 | Jammet et al. |
| 6,626,906 B1 | 9/2003 | Young |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |
| 6,635,086 B2 | 10/2003 | Lin |
| 6,635,087 B2 | 10/2003 | Angelucci et al. |
| 6,638,276 B2 | 10/2003 | Sharkey et al. |
| 6,638,310 B2 | 10/2003 | Lin et al. |
| 6,641,583 B2 | 11/2003 | Shluzas et al. |
| 6,641,585 B2 | 11/2003 | Sato et al. |
| 6,641,586 B2 | 11/2003 | Varieur |
| 6,641,614 B1 | 11/2003 | Wagner et al. |
| 6,645,206 B1 | 11/2003 | Zdeblick et al. |
| 6,645,207 B2 | 11/2003 | Dixon et al. |
| 6,645,208 B2 | 11/2003 | Apfelbaum et al. |
| 6,645,249 B2 | 11/2003 | Ralph et al. |
| 6,648,885 B1 | 11/2003 | Friesem |
| 6,648,887 B2 | 11/2003 | Ashman |
| 6,648,888 B1 | 11/2003 | Shluzas |
| 6,648,891 B2 | 11/2003 | Kim |
| 6,648,894 B2 | 11/2003 | Abdelgany et al. |
| 6,648,895 B2 | 11/2003 | Burkus et al. |
| 6,648,917 B2 | 11/2003 | Gerbec et al. |
| 6,652,525 B1 | 11/2003 | Assaker et al. |
| 6,652,526 B1 | 11/2003 | Arafiles |
| 6,652,533 B2 | 11/2003 | O'Neil |
| 6,652,584 B2 | 11/2003 | Michelson |
| 6,652,586 B2 | 11/2003 | Hunter et al. |
| 6,652,765 B1 | 11/2003 | Beaty |
| 6,652,818 B1 | 11/2003 | Mills et al. |
| 6,656,179 B1 | 12/2003 | Schaefer et al. |
| 6,656,181 B2 | 12/2003 | Dixon et al. |
| 6,656,224 B2 | 12/2003 | Middleton |
| 6,660,004 B2 | 12/2003 | Barker et al. |
| 6,660,006 B2 | 12/2003 | Markworth et al. |
| 6,663,631 B2 | 12/2003 | Kuntz |
| 6,663,632 B1 | 12/2003 | Frigg |
| 6,663,635 B2 | 12/2003 | Frigg et al. |

(56) References Cited

U.S. PATENT DOCUMENTS

| | | |
|---|---|---|
| 6,663,642 B2 | 12/2003 | Beyar et al. |
| 6,665,555 B2 | 12/2003 | Henderson et al. |
| 6,666,612 B2 | 12/2003 | Lorigny et al. |
| 6,666,866 B2 | 12/2003 | Martz et al. |
| 6,666,867 B2 | 12/2003 | Ralph et al. |
| 6,666,890 B2 | 12/2003 | Michelson |
| 6,666,891 B2 | 12/2003 | Boehm et al. |
| 6,668,688 B2 | 12/2003 | Zhao et al. |
| 6,669,700 B1 | 12/2003 | Farris et al. |
| 6,669,730 B2 | 12/2003 | Ralph et al. |
| 6,673,073 B1 | 1/2004 | Schaefer |
| 6,673,113 B2 | 1/2004 | Ralph et al. |
| 6,673,362 B2 | 1/2004 | Calhoun et al. |
| 6,675,805 B1 | 1/2004 | Graether |
| 6,676,661 B1 | 1/2004 | Martin et al. |
| 6,676,703 B2 | 1/2004 | Biscup |
| 6,679,833 B2 | 1/2004 | Smith et al. |
| 6,679,883 B2 | 1/2004 | Hawkes et al. |
| 6,679,887 B2 | 1/2004 | Nicholson et al. |
| 6,679,915 B1 | 1/2004 | Cauthen |
| 6,682,529 B2 | 1/2004 | Stahurski |
| 6,682,530 B2 | 1/2004 | Dixon et al. |
| 6,682,533 B1 | 1/2004 | Dinsdale et al. |
| 6,682,562 B2 | 1/2004 | Viart et al. |
| 6,683,690 B1 | 1/2004 | Tobias |
| 6,685,705 B1 | 2/2004 | Taylor |
| 6,689,133 B2 | 2/2004 | Morrison et al. |
| 6,689,134 B2 | 2/2004 | Ralph et al. |
| 6,692,495 B1 | 2/2004 | Zacouto |
| 6,695,842 B2 | 2/2004 | Zucherman et al. |
| 6,695,843 B2 | 2/2004 | Biedermann et al. |
| 6,695,846 B2 | 2/2004 | Richelsoph et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,699,249 B2 | 3/2004 | Schlapfer et al. |
| 6,702,814 B2 | 3/2004 | Walulik et al. |
| 6,706,045 B2 | 3/2004 | Lin et al. |
| 6,706,067 B2 | 3/2004 | Shimp et al. |
| 6,706,068 B2 | 3/2004 | Ferree |
| 6,706,070 B1 | 3/2004 | Wagner et al. |
| 6,706,922 B2 | 3/2004 | Wolff et al. |
| 6,709,389 B2 | 3/2004 | Farascioni |
| 6,709,458 B2 | 3/2004 | Michelson |
| 6,709,461 B2 | 3/2004 | O'Neil et al. |
| 6,712,795 B1 | 3/2004 | Cohen |
| 6,712,818 B1 | 3/2004 | Michelson |
| 6,712,819 B2 | 3/2004 | Zucherman et al. |
| 6,712,852 B1 | 3/2004 | Chung et al. |
| 6,716,212 B1 | 4/2004 | Pickens |
| 6,716,213 B2 | 4/2004 | Shitoto |
| 6,716,214 B1 | 4/2004 | Jackson |
| 6,716,247 B2 | 4/2004 | Michelson |
| 6,719,794 B2 | 4/2004 | Gerber et al. |
| 6,719,795 B1 | 4/2004 | Cornwall et al. |
| 6,723,043 B2 | 4/2004 | Kleeman et al. |
| 6,723,096 B1 | 4/2004 | Dorchak et al. |
| 6,723,100 B2 | 4/2004 | Biedermann et al. |
| 6,723,126 B1 | 4/2004 | Berry |
| 6,723,127 B2 | 4/2004 | Ralph et al. |
| 6,723,128 B2 | 4/2004 | Uk |
| 6,726,685 B2 | 4/2004 | To et al. |
| 6,726,687 B2 | 4/2004 | Jackson |
| 6,726,720 B2 | 4/2004 | Ross et al. |
| 6,730,093 B2 | 5/2004 | Saint |
| 6,730,126 B2 | 5/2004 | Boehm et al. |
| 6,730,127 B2 | 5/2004 | Michelson |
| 6,733,444 B2 | 5/2004 | Phillips |
| 6,733,496 B2 | 5/2004 | Sharkey et al. |
| 6,733,502 B2 | 5/2004 | Altarac et al. |
| 6,733,531 B1 | 5/2004 | Trieu |
| 6,733,534 B2 | 5/2004 | Sherman |
| 6,733,535 B2 | 5/2004 | Michelson |
| 6,736,816 B2 | 5/2004 | Ritland |
| 6,736,817 B2 | 5/2004 | Troxell et al. |
| 6,736,820 B2 | 5/2004 | Biedermann et al. |
| 6,739,068 B1 | 5/2004 | Rinner |
| 6,740,086 B2 | 5/2004 | Richelsoph |
| 6,740,087 B2 | 5/2004 | Knox |
| 6,740,090 B1 | 5/2004 | Cragg et al. |
| 6,740,118 B2 | 5/2004 | Eisermann et al. |
| 6,743,231 B1 | 6/2004 | Gray et al. |
| 6,743,255 B2 | 6/2004 | Ferree |
| 6,743,256 B2 | 6/2004 | Mason |
| 6,743,257 B2 | 6/2004 | Castro |
| 6,746,449 B2 | 6/2004 | Jones et al. |
| 6,746,454 B2 | 6/2004 | Winterbottom et al. |
| 6,749,613 B1 | 6/2004 | Conchy et al. |
| 6,749,614 B2 | 6/2004 | Teitelbaum et al. |
| 6,749,635 B1 | 6/2004 | Bryan |
| 6,749,636 B2 | 6/2004 | Michelson |
| 6,752,832 B2 | 6/2004 | Neumann |
| 6,755,829 B1 | 6/2004 | Bono et al. |
| 6,755,830 B2 | 6/2004 | Minfelde et al. |
| 6,755,833 B1 | 6/2004 | Paul et al. |
| 6,755,835 B2 | 6/2004 | Schultheiss et al. |
| 6,755,836 B1 | 6/2004 | Lewis |
| 6,755,841 B2 | 6/2004 | Fraser et al. |
| 6,758,861 B2 | 7/2004 | Ralph et al. |
| 6,761,719 B2 | 7/2004 | Justis et al. |
| 6,761,720 B1 | 7/2004 | Senegas |
| 6,761,721 B2 | 7/2004 | Burgess et al. |
| 6,761,723 B2 | 7/2004 | Buttermann et al. |
| 6,761,738 B1 | 7/2004 | Boyd |
| 6,764,515 B2 | 7/2004 | Ralph et al. |
| 6,767,351 B2 | 7/2004 | Orbay et al. |
| 6,767,367 B1 | 7/2004 | Michelson |
| 6,770,074 B2 | 8/2004 | Michelson |
| 6,770,075 B2 | 8/2004 | Howland |
| 6,770,096 B2 | 8/2004 | Bolger et al. |
| 6,778,861 B1 | 8/2004 | Liebrecht et al. |
| 6,780,186 B2 | 8/2004 | Errico et al. |
| 6,780,192 B2 | 8/2004 | McKay et al. |
| 6,783,527 B2 | 8/2004 | Drewry et al. |
| 6,783,547 B2 | 8/2004 | Castro |
| 6,790,209 B2 | 9/2004 | Beale et al. |
| 6,790,210 B1 | 9/2004 | Cragg et al. |
| 6,793,658 B2 | 9/2004 | LeHuec et al. |
| 6,802,844 B2 | 10/2004 | Ferree |
| 6,805,697 B1 | 10/2004 | Helm et al. |
| 6,805,713 B1 | 10/2004 | Carter et al. |
| 6,805,714 B2 | 10/2004 | Sutcliffe |
| 6,808,493 B1 | 10/2004 | Bookwalter et al. |
| 6,808,537 B2 | 10/2004 | Michelson |
| 6,811,567 B2 | 11/2004 | Reiley |
| 6,814,737 B2 | 11/2004 | Cauthen |
| 6,821,277 B2 | 11/2004 | Teitelbaum |
| 6,824,565 B2 | 11/2004 | Muhanna et al. |
| 6,827,719 B2 | 12/2004 | Ralph et al. |
| 6,827,722 B1 | 12/2004 | Schoenefeld |
| 6,830,570 B1 | 12/2004 | Frey et al. |
| 6,830,571 B2 | 12/2004 | Lenke et al. |
| 6,830,589 B2 | 12/2004 | Erickson |
| 6,832,997 B2 | 12/2004 | Uchida et al. |
| 6,832,999 B2 | 12/2004 | Ueyama et al. |
| 6,835,196 B2 | 12/2004 | Biedermann et al. |
| 6,835,206 B2 | 12/2004 | Jackson |
| 6,837,884 B2 | 1/2005 | Woloszko |
| 6,837,889 B2 | 1/2005 | Shluzas |
| 6,840,940 B2 | 1/2005 | Ralph et al. |
| 6,843,791 B2 | 1/2005 | Serhan |
| 6,849,076 B2 | 2/2005 | Blunn et al. |
| 6,849,093 B2 | 2/2005 | Michelson |
| 6,852,127 B2 | 2/2005 | Varga et al. |
| 6,852,128 B2 | 2/2005 | Lange |
| 6,852,129 B2 | 2/2005 | Gerbec et al. |
| 6,855,147 B2 | 2/2005 | Harrington et al. |
| 6,857,343 B1 | 2/2005 | Easterbrooks et al. |
| 6,858,030 B2 | 2/2005 | Martin et al. |
| 6,858,031 B2 | 2/2005 | Morrison et al. |
| 6,860,850 B2 | 3/2005 | Phillips et al. |
| 6,863,673 B2 | 3/2005 | Gerbec et al. |
| 6,869,398 B2 | 3/2005 | Obenchain et al. |
| 6,869,432 B2 | 3/2005 | Schlapfer et al. |

(56) References Cited

U.S. PATENT DOCUMENTS

| | | |
|---|---|---|
| 6,869,433 B2 | 3/2005 | Glascott |
| 6,872,208 B1 | 3/2005 | McBride et al. |
| 6,875,211 B2 | 4/2005 | Nichols et al. |
| 6,881,228 B2 | 4/2005 | Zdeblick et al. |
| 6,884,241 B2 | 4/2005 | Bertranou et al. |
| 6,884,242 B2 | 4/2005 | LeHuec et al. |
| 6,884,243 B2 | 4/2005 | Sellers |
| 6,885,243 B2 | 4/2005 | Burstein et al. |
| D505,205 S | 5/2005 | Freid |
| 6,887,242 B2 | 5/2005 | Doubler et al. |
| 6,890,355 B2 | 5/2005 | Michelson |
| 6,893,444 B2 | 5/2005 | Orbay |
| 6,896,675 B2 | 5/2005 | Leung et al. |
| 6,896,676 B2 | 5/2005 | Zubok et al. |
| 6,896,677 B1 | 5/2005 | Lin |
| 6,896,680 B2 | 5/2005 | Michelson |
| 6,899,714 B2 | 5/2005 | Vaughan |
| 6,899,716 B2 | 5/2005 | Cragg |
| 6,902,566 B2 | 6/2005 | Zucherman et al. |
| 6,902,580 B2 | 6/2005 | Fallin et al. |
| 6,911,045 B2 | 6/2005 | Shimp |
| 6,916,320 B2 | 7/2005 | Michelson |
| 6,916,340 B2 | 7/2005 | Metzger et al. |
| 6,918,910 B2 | 7/2005 | Smith et al. |
| 6,918,911 B2 | 7/2005 | Biedermann et al. |
| 6,921,403 B2 | 7/2005 | Cragg et al. |
| 6,923,811 B1 | 8/2005 | Carl et al. |
| 6,923,830 B2 | 8/2005 | Michelson |
| 6,926,658 B2 | 8/2005 | Farnan |
| 6,926,737 B2 | 8/2005 | Jackson |
| 6,929,606 B2 | 8/2005 | Ritland |
| 6,929,640 B1 | 8/2005 | Underwood et al. |
| 6,932,817 B2 | 8/2005 | Baynham et al. |
| 6,932,820 B2 | 8/2005 | Osman |
| 6,936,071 B1 | 8/2005 | Marnay et al. |
| 6,945,933 B2 | 9/2005 | Branch et al. |
| 6,945,972 B2 | 9/2005 | Frigg et al. |
| 6,945,973 B2 | 9/2005 | Bray |
| 6,945,975 B2 | 9/2005 | Dalton |
| 6,947,967 B2 | 9/2005 | Ferris et al. |
| 6,949,100 B1 | 9/2005 | Venturini |
| 6,949,105 B2 | 9/2005 | Bryan et al. |
| 6,951,538 B2 | 10/2005 | Ritland |
| 6,951,561 B2 | 10/2005 | Warren et al. |
| 6,953,462 B2 | 10/2005 | Lieberman |
| 6,953,477 B2 | 10/2005 | Berry |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,666 B2 | 11/2005 | Jackson |
| 6,964,667 B2 | 11/2005 | Shaolian et al. |
| 6,964,687 B1 | 11/2005 | Bernard et al. |
| 6,966,910 B2 | 11/2005 | Ritland |
| 6,966,929 B2 | 11/2005 | Mitchell |
| 6,972,019 B2 | 12/2005 | Michelson |
| 6,972,035 B2 | 12/2005 | Michelson |
| 6,974,460 B2 | 12/2005 | Carbone et al. |
| 6,979,334 B2 | 12/2005 | Dalton |
| 6,980,862 B2 | 12/2005 | Fredricks et al. |
| 6,981,973 B2 | 1/2006 | McKinley |
| 6,981,975 B2 | 1/2006 | Michelson |
| 6,984,234 B2 | 1/2006 | Bray |
| 6,984,245 B2 | 1/2006 | McGahan et al. |
| 6,986,771 B2 | 1/2006 | Paul et al. |
| 6,986,772 B2 | 1/2006 | Michelson |
| 6,989,011 B2 | 1/2006 | Paul et al. |
| 6,989,044 B2 | 1/2006 | Zhang et al. |
| 6,991,632 B2 | 1/2006 | Ritland |
| 6,991,654 B2 | 1/2006 | Foley |
| 6,994,688 B2 | 2/2006 | Brauckman et al. |
| 6,997,941 B2 | 2/2006 | Sharkey et al. |
| 7,001,385 B2 | 2/2006 | Bonutti |
| 7,001,432 B2 | 2/2006 | Keller et al. |
| 7,004,947 B2 | 2/2006 | Shluzas et al. |
| RE39,035 E | 3/2006 | Finn |
| 7,008,422 B2 | 3/2006 | Foley et al. |
| 7,008,424 B2 | 3/2006 | Teitelbaum |
| 7,008,426 B2 | 3/2006 | Paul |
| 7,008,453 B1 | 3/2006 | Michelson |
| 7,011,619 B1 | 3/2006 | Lewis et al. |
| 7,011,658 B2 | 3/2006 | Young |
| 7,011,660 B2 | 3/2006 | Sherman et al. |
| 7,014,608 B2 | 3/2006 | Larson et al. |
| 7,014,633 B2 | 3/2006 | Cragg |
| 7,018,378 B2 | 3/2006 | Biedermann et al. |
| 7,018,379 B2 | 3/2006 | Drewry et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,022,122 B2 | 4/2006 | Amrein et al. |
| 7,025,716 B1 | 4/2006 | Meloul et al. |
| 7,025,787 B2 | 4/2006 | Bryan et al. |
| 7,029,472 B1 | 4/2006 | Fortin |
| 7,029,475 B2 | 4/2006 | Panjabi |
| 7,033,362 B2 | 4/2006 | McGahan et al. |
| RE39,089 E | 5/2006 | Ralph |
| 7,037,339 B2 | 5/2006 | Houfburg |
| 7,041,135 B2 | 5/2006 | Michelson |
| 7,041,136 B2 | 5/2006 | Goble et al. |
| 7,044,971 B2 | 5/2006 | Suddaby |
| 7,048,736 B2 | 5/2006 | Robinson et al. |
| 7,052,497 B2 | 5/2006 | Sherman et al. |
| 7,056,321 B2 | 6/2006 | Pagliuca et al. |
| 7,056,344 B2 | 6/2006 | Huppert et al. |
| 7,060,066 B2 | 6/2006 | Zhao et al. |
| 7,060,097 B2 | 6/2006 | Fraser et al. |
| 7,063,702 B2 | 6/2006 | Michelson |
| 7,066,062 B2 | 6/2006 | Flesher |
| 7,066,937 B2 | 6/2006 | Shluzas |
| 7,066,961 B2 | 6/2006 | Michelson |
| 7,070,598 B2 | 7/2006 | Lim et al. |
| 7,074,237 B2 | 7/2006 | Goble et al. |
| 7,081,116 B1 | 7/2006 | Carly |
| 7,083,621 B2 | 8/2006 | Shaolian et al. |
| 7,083,622 B2 | 8/2006 | Simonson |
| 7,083,625 B2 | 8/2006 | Berry |
| 7,083,649 B2 | 8/2006 | Zucherman et al. |
| 7,087,057 B2 | 8/2006 | Konieczynski et al. |
| 7,087,058 B2 | 8/2006 | Cragg |
| 7,087,083 B2 | 8/2006 | Pasquet et al. |
| 7,090,674 B2 | 8/2006 | Doubler et al. |
| 7,090,679 B2 | 8/2006 | Saint et al. |
| 7,090,680 B2 | 8/2006 | Bonati et al. |
| 7,094,242 B2 | 8/2006 | Ralph et al. |
| 7,094,258 B2 | 8/2006 | Lambrecht et al. |
| 7,097,648 B1 | 8/2006 | Globerman et al. |
| 7,101,375 B2 | 9/2006 | Zucherman et al. |
| 7,101,399 B2 | 9/2006 | Errico et al. |
| 7,105,024 B2 | 9/2006 | Richelsoph |
| 7,108,698 B2 | 9/2006 | Robbins et al. |
| 7,112,206 B2 | 9/2006 | Michelson |
| 7,118,576 B2 | 10/2006 | Gitis et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,121,755 B2 | 10/2006 | Schlapfer et al. |
| 7,122,629 B2 | 10/2006 | Bejanin et al. |
| 7,125,410 B2 | 10/2006 | Freudiger |
| 7,125,425 B2 | 10/2006 | Simonton et al. |
| 7,125,426 B2 | 10/2006 | Moumene et al. |
| 7,128,743 B2 | 10/2006 | Metz-Stavenhagen |
| 7,128,760 B2 | 10/2006 | Michelson |
| 7,128,761 B2 | 10/2006 | Kuras et al. |
| 7,137,985 B2 | 11/2006 | Jahng |
| 7,137,986 B2 | 11/2006 | Troxell et al. |
| 7,141,051 B2 | 11/2006 | Janowski et al. |
| 7,144,396 B2 | 12/2006 | Shluzas |
| 7,144,397 B2 | 12/2006 | Lambrecht et al. |
| 7,147,599 B2 | 12/2006 | Phillips et al. |
| 7,150,714 B2 | 12/2006 | Myles |
| 7,153,281 B2 | 12/2006 | Holmes |
| 7,153,325 B2 | 12/2006 | Kim et al. |
| 7,156,806 B2 | 1/2007 | Dobrovolny |

(56) References Cited

U.S. PATENT DOCUMENTS

| | | |
|---|---|---|
| 7,160,300 B2 | 1/2007 | Jackson |
| 7,163,538 B2 | 1/2007 | Altarac et al. |
| 7,163,539 B2 | 1/2007 | Abdelgany et al. |
| 7,163,558 B2 | 1/2007 | Senegas et al. |
| 7,163,561 B2 | 1/2007 | Michelson |
| 7,166,073 B2 | 1/2007 | Ritland |
| 7,166,107 B2 | 1/2007 | Anderson |
| 7,166,108 B2 | 1/2007 | Mazda et al. |
| 7,166,121 B2 | 1/2007 | Reiley et al. |
| 7,169,183 B2 | 1/2007 | Liu et al. |
| 7,179,261 B2 | 2/2007 | Sicvol et al. |
| 7,182,729 B2 | 2/2007 | Abdelgany et al. |
| 7,186,255 B2 | 3/2007 | Baynham et al. |
| 7,188,626 B2 | 3/2007 | Foley et al. |
| 7,198,644 B2 | 4/2007 | Schultz et al. |
| 7,201,751 B2 | 4/2007 | Zucherman et al. |
| 7,204,851 B2 | 4/2007 | Trieu et al. |
| 7,204,852 B2 | 4/2007 | Marnay et al. |
| 7,204,853 B2 | 4/2007 | Gordon et al. |
| 7,207,949 B2 | 4/2007 | Miles et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,211,112 B2 | 5/2007 | Baynham et al. |
| 7,214,186 B2 | 5/2007 | Ritland |
| 7,214,227 B2 | 5/2007 | Colleran et al. |
| 7,217,291 B2 | 5/2007 | Zucherman et al. |
| 7,223,268 B2 | 5/2007 | Biedermann |
| 7,223,289 B2 | 5/2007 | Trieu et al. |
| 7,227,477 B2 | 6/2007 | Ye |
| 7,229,441 B2 | 6/2007 | Trieu et al. |
| 7,232,441 B2 | 6/2007 | Altarac et al. |
| 7,232,463 B2 | 6/2007 | Falahee |
| 7,232,464 B2 | 6/2007 | Mathieu et al. |
| 7,235,048 B2 | 6/2007 | Rein et al. |
| 7,235,105 B2 | 6/2007 | Jackson |
| 7,241,297 B2 | 7/2007 | Shaolian et al. |
| 7,250,052 B2 | 7/2007 | Landry et al. |
| 7,252,673 B2 | 8/2007 | Lim |
| 7,264,621 B2 | 9/2007 | Coates et al. |
| 7,270,665 B2 | 9/2007 | Morrison et al. |
| 7,273,496 B2 | 9/2007 | Mitchell |
| 7,276,081 B1 | 10/2007 | Coates et al. |
| 7,276,082 B2 | 10/2007 | Zdeblick et al. |
| 7,282,063 B2 | 10/2007 | Cohen et al. |
| 7,282,064 B2 | 10/2007 | Chin |
| 7,282,065 B2 | 10/2007 | Kirschman et al. |
| 7,285,121 B2 | 10/2007 | Braun et al. |
| 7,291,149 B1 | 11/2007 | Michelson |
| 7,291,151 B2 | 11/2007 | Alvarez et al. |
| 7,291,152 B2 | 11/2007 | Abdou |
| 7,291,153 B2 | 11/2007 | Glascott |
| 7,294,128 B2 | 11/2007 | Alleyne et al. |
| 7,294,129 B2 | 11/2007 | Hawkins et al. |
| 7,300,441 B2 | 11/2007 | Haid et al. |
| 7,303,563 B2 | 12/2007 | Poyner et al. |
| 7,306,603 B2 | 12/2007 | Boehm et al. |
| 7,306,604 B2 | 12/2007 | Carli |
| 7,306,606 B2 | 12/2007 | Sasing |
| 7,306,628 B2 | 12/2007 | Zucherman et al. |
| 7,309,338 B2 | 12/2007 | Cragg |
| 7,311,734 B2 | 12/2007 | Hoeck et al. |
| 7,314,467 B2 | 1/2008 | Howland |
| 7,316,684 B1 | 1/2008 | Baccelli et al. |
| 7,316,714 B2 | 1/2008 | Gordon et al. |
| 7,318,817 B2 | 1/2008 | Hamada |
| 7,318,840 B2 | 1/2008 | McKay |
| 7,322,979 B2 | 1/2008 | Crandall et al. |
| 7,326,216 B2 | 2/2008 | Bertagnoli et al. |
| 7,329,258 B2 | 2/2008 | Studer |
| 7,331,961 B2 | 2/2008 | Abdou |
| 7,331,995 B2 | 2/2008 | Eisermann et al. |
| 7,335,201 B2 | 2/2008 | Doubler et al. |
| 7,335,202 B2 | 2/2008 | Matthis et al. |
| 7,335,203 B2 | 2/2008 | Winslow et al. |
| 7,338,490 B2 | 3/2008 | Ogilvie et al. |
| 7,338,491 B2 | 3/2008 | Baker et al. |
| 7,338,527 B2 | 3/2008 | Blatt et al. |
| 7,341,587 B2 | 3/2008 | Molz et al. |
| 7,347,874 B2 | 3/2008 | Disilvestro |
| 7,361,179 B2 | 4/2008 | Rousseau et al. |
| 7,361,196 B2 | 4/2008 | Fallin et al. |
| 7,374,534 B2 | 5/2008 | Dalton |
| 7,377,921 B2 | 5/2008 | Studer et al. |
| 7,377,942 B2 | 5/2008 | Berry |
| 7,396,328 B2 | 7/2008 | Penenberg |
| 7,396,360 B2 | 7/2008 | Lieberman |
| 7,410,501 B2 | 8/2008 | Michelson |
| 7,419,505 B2 | 9/2008 | Fleischmann et al. |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,637 B2 | 11/2008 | Taylor |
| 7,455,639 B2 | 11/2008 | Ritland |
| 7,455,685 B2 | 11/2008 | Justis |
| 7,465,306 B2 | 12/2008 | Pond, Jr. et al. |
| 7,473,223 B2 | 1/2009 | Fetzer et al. |
| 7,473,276 B2 | 1/2009 | Aebi et al. |
| 7,476,228 B2 | 1/2009 | Abdou |
| 7,476,238 B2 | 1/2009 | Panjabi |
| 7,479,160 B2 | 1/2009 | Branch et al. |
| 7,485,132 B1 | 2/2009 | McBride et al. |
| 7,491,205 B1 | 2/2009 | Michelson |
| 7,491,208 B2 | 2/2009 | Pond et al. |
| 7,494,508 B2 | 2/2009 | Zeegers et al. |
| 7,497,859 B2 | 3/2009 | Zucherman et al. |
| 7,503,918 B2 | 3/2009 | Baccelli et al. |
| 7,503,933 B2 | 3/2009 | Michelson |
| 7,520,888 B2 | 4/2009 | Trieu |
| 7,527,640 B2 | 5/2009 | Ziolo et al. |
| 7,534,265 B1 | 5/2009 | Boyd et al. |
| 7,537,565 B2 | 5/2009 | Bass |
| 7,537,616 B1 | 5/2009 | Branch et al. |
| 7,540,882 B2 | 6/2009 | Michelson |
| 7,547,308 B2 | 6/2009 | Bertagnoli et al. |
| 7,547,325 B2 | 6/2009 | Biedermann et al. |
| 7,556,639 B2 | 7/2009 | Rothman et al. |
| 7,559,930 B2 | 7/2009 | Allard et al. |
| 7,559,942 B2 | 7/2009 | Paul et al. |
| 7,563,274 B2 | 7/2009 | Justis et al. |
| 7,563,283 B2 | 7/2009 | Kwak et al. |
| 7,566,345 B1 | 7/2009 | Fallin et al. |
| 7,569,014 B2 | 8/2009 | Bass et al. |
| 7,572,276 B2 | 8/2009 | Lim et al. |
| 7,575,580 B2 | 8/2009 | Lim et al. |
| 7,575,587 B2 | 8/2009 | Rezach et al. |
| 7,578,820 B2 | 8/2009 | Moore et al. |
| 7,578,849 B2 | 8/2009 | Trieu |
| 7,582,058 B1 | 9/2009 | Miles et al. |
| 7,582,107 B2 | 9/2009 | Trail et al. |
| 7,585,316 B2 | 9/2009 | Trieu |
| 7,588,537 B2 | 9/2009 | Bass |
| 7,588,579 B2 | 9/2009 | Mommaerts et al. |
| 7,588,589 B2 | 9/2009 | Falahee |
| 7,588,593 B2 | 9/2009 | Aferzon |
| 7,591,839 B2 | 9/2009 | Biedermann et al. |
| 7,591,851 B2 | 9/2009 | Winslow et al. |
| 7,594,919 B2 | 9/2009 | Peterman |
| 7,594,931 B2 | 9/2009 | Louis et al. |
| 7,594,932 B2 | 9/2009 | Aferzon et al. |
| 7,597,694 B2 | 10/2009 | Lim et al. |
| 7,601,166 B2 | 10/2009 | Biedermann et al. |
| 7,601,170 B2 | 10/2009 | Winslow et al. |
| 7,604,643 B2 | 10/2009 | Ciccone et al. |
| 7,604,654 B2 | 10/2009 | Fallin et al. |
| 7,611,518 B2 | 11/2009 | Walder et al. |
| 7,618,423 B1 | 11/2009 | Valentine et al. |
| 7,618,443 B2 | 11/2009 | Abdou et al. |
| 7,618,455 B2 | 11/2009 | Goble et al. |
| 7,618,456 B2 | 11/2009 | Mathieu et al. |
| 7,621,912 B2 | 11/2009 | Harms et al. |

(56) References Cited

U.S. PATENT DOCUMENTS

| | | |
|---|---|---|
| 7,621,939 B2 | 11/2009 | Zucherman et al. |
| 7,621,940 B2 | 11/2009 | Harms et al. |
| 7,621,942 B2 | 11/2009 | Piehl |
| 7,621,953 B2 | 11/2009 | Braddock, Jr. et al. |
| 7,621,955 B2 | 11/2009 | Goble et al. |
| 7,621,957 B2 | 11/2009 | Errico et al. |
| 7,625,379 B2 | 12/2009 | Puno et al. |
| 7,625,380 B2 | 12/2009 | Drewry et al. |
| 7,625,393 B2 | 12/2009 | Fallin et al. |
| 7,625,396 B2 | 12/2009 | Jackson |
| 7,628,799 B2 | 12/2009 | Richelsoph et al. |
| 7,632,292 B2 | 12/2009 | Sengupta et al. |
| 7,635,366 B2 | 12/2009 | Abdou et al. |
| 7,635,371 B2 | 12/2009 | McGahan et al. |
| 7,641,673 B2 | 1/2010 | Le et al. |
| 7,641,690 B2 | 1/2010 | Abdou et al. |
| 7,641,693 B2 | 1/2010 | Gutlin et al. |
| 7,645,281 B2 | 1/2010 | Marik |
| 7,651,515 B2 | 1/2010 | Mack et al. |
| 7,654,954 B1 | 2/2010 | Phillips et al. |
| 7,655,026 B2 | 2/2010 | Justis et al. |
| 7,655,027 B2 | 2/2010 | Michelson |
| 7,655,028 B2 | 2/2010 | Kirschman et al. |
| 7,655,042 B2 | 2/2010 | Foley et al. |
| 7,658,739 B2 | 2/2010 | Shluzas |
| 7,658,752 B2 | 2/2010 | Labrom et al. |
| 7,658,766 B2 | 2/2010 | Melkent et al. |
| 7,682,375 B2 | 3/2010 | Ritland |
| 7,682,396 B2 | 3/2010 | Beaurain et al. |
| 7,686,809 B2 | 3/2010 | Triplett et al. |
| 7,691,057 B2 | 4/2010 | Miles et al. |
| 7,691,129 B2 | 4/2010 | Felix |
| 7,695,496 B2 | 4/2010 | Labrom et al. |
| 7,695,498 B2 | 4/2010 | Ritland |
| 7,695,514 B2 | 4/2010 | Kwak et al. |
| 7,695,516 B2 | 4/2010 | Zeegers |
| 7,695,517 B2 | 4/2010 | Benzel et al. |
| 7,704,271 B2 | 4/2010 | Abdou et al. |
| 7,708,743 B2 | 5/2010 | Anderson et al. |
| 7,708,765 B2 | 5/2010 | Carl et al. |
| 7,722,618 B2 | 5/2010 | Estes et al. |
| 7,727,233 B2 | 6/2010 | Blackwell et al. |
| 7,727,280 B2 | 6/2010 | McLuen |
| 7,738,968 B2 | 6/2010 | Bleich |
| 7,744,635 B2 | 6/2010 | Sweeney et al. |
| 7,749,231 B2 | 7/2010 | Bonvallet et al. |
| 7,749,252 B2 | 7/2010 | Zucherman et al. |
| 7,749,269 B2 | 7/2010 | Peterman et al. |
| 7,749,270 B2 | 7/2010 | Peterman |
| 7,749,274 B2 | 7/2010 | Razian |
| 7,753,844 B2 | 7/2010 | Sharratt et al. |
| 7,753,937 B2 | 7/2010 | Chervitz et al. |
| 7,753,938 B2 | 7/2010 | Aschmann et al. |
| 7,753,958 B2 | 7/2010 | Gordon et al. |
| 7,758,274 B2 | 7/2010 | Paul |
| 7,758,501 B2 | 7/2010 | Frasier et al. |
| 7,758,644 B2 | 7/2010 | Trieu et al. |
| 7,758,645 B2 | 7/2010 | Studer et al. |
| 7,758,648 B2 | 7/2010 | Castleman et al. |
| 7,763,074 B2 | 7/2010 | Altarac et al. |
| 7,763,078 B2 | 7/2010 | Peterman et al. |
| 7,766,918 B2 | 8/2010 | Allard et al. |
| 7,771,432 B2 | 8/2010 | Schwab et al. |
| 7,771,473 B2 | 8/2010 | Thramann |
| 7,771,475 B2 | 8/2010 | Michelson |
| 7,776,049 B1 | 8/2010 | Curran et al. |
| 7,776,067 B2 | 8/2010 | Jackson |
| 7,776,090 B2 | 8/2010 | Winslow et al. |
| 7,780,670 B2 | 8/2010 | Bonutti |
| 7,780,732 B2 | 8/2010 | Abernathie et al. |
| 7,789,914 B2 | 9/2010 | Michelson |
| 7,794,501 B2 | 9/2010 | Edie et al. |
| 7,799,053 B2 | 9/2010 | Haid et al. |
| 7,799,081 B2 | 9/2010 | McKinley |
| 7,806,911 B2 | 10/2010 | Peckham |
| 7,806,913 B2 | 10/2010 | Fanger et al. |
| 7,811,326 B2 | 10/2010 | Braddock, Jr. et al. |
| 7,815,683 B2 | 10/2010 | Melkent et al. |
| 7,819,801 B2 | 10/2010 | Miles et al. |
| 7,819,903 B2 | 10/2010 | Fraser et al. |
| 7,824,445 B2 | 11/2010 | Biro et al. |
| 7,828,807 B2 | 11/2010 | LeHuec et al. |
| 7,828,847 B2 | 11/2010 | Abdou et al. |
| 7,837,688 B2 | 11/2010 | Boyer et al. |
| 7,837,714 B2 | 11/2010 | Drewry et al. |
| 7,837,732 B2 | 11/2010 | Zucherman et al. |
| 7,837,734 B2 | 11/2010 | Zucherman et al. |
| 7,842,074 B2 | 11/2010 | Abdou |
| 7,846,186 B2 | 12/2010 | Taylor |
| 7,846,207 B2 | 12/2010 | Lechmann et al. |
| 7,850,608 B2 | 12/2010 | Hamada |
| 7,850,731 B2 | 12/2010 | Brittan et al. |
| 7,850,732 B2 | 12/2010 | Heinz |
| 7,850,733 B2 | 12/2010 | Baynham et al. |
| 7,854,752 B2 | 12/2010 | Colleran et al. |
| 7,857,818 B2 | 12/2010 | Trieu et al. |
| 7,857,833 B2 | 12/2010 | Abdou et al. |
| 7,871,426 B2 | 1/2011 | Chin et al. |
| 7,875,034 B2 | 1/2011 | Josse et al. |
| 7,875,076 B2 | 1/2011 | Mathieu et al. |
| 7,875,078 B2 | 1/2011 | Wysocki et al. |
| 7,879,074 B2 | 2/2011 | Kwak et al. |
| 7,883,532 B2 | 2/2011 | Biscup et al. |
| 7,883,542 B2 | 2/2011 | Zipnick et al. |
| 7,887,591 B2 | 2/2011 | Aebi et al. |
| 7,892,173 B2 | 2/2011 | Miles et al. |
| 7,892,261 B2 | 2/2011 | Bonutti |
| 7,892,286 B2 | 2/2011 | Michelson et al. |
| 7,901,409 B2 | 3/2011 | Canaveral et al. |
| 7,901,458 B2 | 3/2011 | DeRidder et al. |
| 7,905,840 B2 | 3/2011 | Pimenta et al. |
| 7,905,886 B1 | 3/2011 | Curran et al. |
| 7,909,829 B2 | 3/2011 | Patel et al. |
| 7,909,848 B2 | 3/2011 | Patel et al. |
| 7,909,870 B2 | 3/2011 | Kraus |
| 7,909,871 B2 | 3/2011 | Abdou et al. |
| 7,914,558 B2 | 3/2011 | Landry et al. |
| 7,918,792 B2 | 4/2011 | Drzyzga et al. |
| 7,922,658 B2 | 4/2011 | Cohen et al. |
| 7,922,745 B2 | 4/2011 | Hestad et al. |
| 7,922,750 B2 | 4/2011 | Trautwein et al. |
| 7,927,337 B2 | 4/2011 | Keller |
| 7,931,589 B2 | 4/2011 | Cohen et al. |
| 7,931,674 B2 | 4/2011 | Zucherman et al. |
| 7,935,134 B2 | 5/2011 | Reglos et al. |
| 7,935,147 B2 | 5/2011 | Wales |
| 7,935,149 B2 | 5/2011 | Michelson |
| 7,938,848 B2 | 5/2011 | Sweeney |
| 7,946,982 B2 | 5/2011 | Hamada |
| 7,951,198 B2 | 5/2011 | Sucec et al. |
| 7,955,390 B2 | 6/2011 | Fallin et al. |
| 7,955,392 B2 | 6/2011 | Dewey et al. |
| 7,959,564 B2 | 6/2011 | Ritland |
| 7,959,677 B2 | 6/2011 | Landry et al. |
| 7,972,363 B2 | 7/2011 | Moskowitz et al. |
| 7,976,566 B2 | 7/2011 | Michelson |
| 7,981,031 B2 | 7/2011 | Frasier et al. |
| 7,985,258 B2 | 7/2011 | Zdeblick et al. |
| 7,988,699 B2 | 8/2011 | Martz et al. |
| 8,002,802 B2 | 8/2011 | Abdou et al. |
| 8,002,833 B2 | 8/2011 | Fabris et al. |
| 8,002,842 B2 | 8/2011 | Ronk |
| 8,012,207 B2 | 9/2011 | Kim |
| 8,021,393 B2 | 9/2011 | Seifert et al. |
| 8,021,401 B2 | 9/2011 | Carl et al. |
| 8,021,429 B2 | 9/2011 | Viker |
| 8,025,680 B2 | 9/2011 | Hayes et al. |
| 8,025,697 B2 | 9/2011 | Abdelgany et al. |
| 8,034,109 B2 | 10/2011 | Zwirkoski |
| 8,038,716 B2 | 10/2011 | Duggal et al. |
| 8,043,334 B2 | 10/2011 | Fisher et al. |
| 8,043,343 B2 | 10/2011 | Miller et al. |
| 8,043,376 B2 | 10/2011 | Falahee |
| 8,043,380 B1 | 10/2011 | Park et al. |

(56) References Cited

U.S. PATENT DOCUMENTS

| | | |
|---|---|---|
| 8,048,120 B1 | 11/2011 | Fallin et al. |
| 8,062,299 B2 | 11/2011 | McGahan et al. |
| 8,062,336 B2 | 11/2011 | Triplett et al. |
| 8,062,337 B2 | 11/2011 | Bruneau et al. |
| 8,066,710 B2 | 11/2011 | Estes et al. |
| 8,066,714 B2 | 11/2011 | Shipp et al. |
| 8,066,741 B2 | 11/2011 | Fallin et al. |
| 8,066,742 B2 | 11/2011 | Anderson et al. |
| 8,066,749 B2 | 11/2011 | Winslow et al. |
| 8,070,749 B2 | 12/2011 | Stern |
| 8,070,816 B2 | 12/2011 | Taylor et al. |
| 8,075,593 B2 | 12/2011 | Hess |
| 8,075,618 B2 | 12/2011 | Trieu et al. |
| 8,075,621 B2 | 12/2011 | Michelson |
| 8,080,046 B2 | 12/2011 | Suddaby |
| 8,083,798 B2 | 12/2011 | Allard et al. |
| 8,097,018 B2 | 1/2012 | Malandain et al. |
| 8,100,828 B2 | 1/2012 | Frey et al. |
| 8,105,358 B2 | 1/2012 | Phan |
| 8,114,131 B2 | 2/2012 | Kohm et al. |
| 8,123,807 B2 | 2/2012 | Kim |
| 8,128,659 B2 | 3/2012 | Ginsberg et al. |
| 8,128,664 B2 | 3/2012 | Pasquet |
| 8,137,284 B2 | 3/2012 | Miles et al. |
| 8,142,479 B2 | 3/2012 | Hess |
| 8,157,840 B2 | 4/2012 | Zucherman et al. |
| 8,163,026 B2 | 4/2012 | Gray |
| 8,167,887 B2 | 5/2012 | McLean |
| 8,167,908 B2 | 5/2012 | Ely et al. |
| 8,167,915 B2 | 5/2012 | Ferree et al. |
| 8,167,946 B2 | 5/2012 | Michelson |
| 8,167,949 B2 | 5/2012 | Tyber et al. |
| 8,172,855 B2 | 5/2012 | Abdou |
| 8,182,423 B2 | 5/2012 | Miles et al. |
| 8,192,358 B2 | 6/2012 | Leahy |
| 8,197,514 B2 | 6/2012 | Maas et al. |
| 8,197,522 B2 | 6/2012 | Park et al. |
| 8,206,420 B2 | 6/2012 | Patel et al. |
| 8,216,312 B2 | 7/2012 | Gray |
| 8,226,690 B2 | 7/2012 | Altarac et al. |
| 8,231,623 B1 | 7/2012 | Jordan |
| 8,241,330 B2 | 8/2012 | Lamborne et al. |
| 8,241,359 B2 | 8/2012 | Davis et al. |
| 8,241,362 B2 | 8/2012 | Voorhies |
| 8,251,997 B2 | 8/2012 | Michelson |
| 8,268,004 B2 | 9/2012 | Castleman et al. |
| 8,277,489 B2 | 10/2012 | Saidha et al. |
| 8,287,569 B1 | 10/2012 | Powell |
| 8,303,629 B1 | 11/2012 | Abdou |
| 8,303,660 B1 | 11/2012 | Abdou |
| 8,308,804 B2 | 11/2012 | Krueger |
| 8,343,046 B2 | 1/2013 | Miles et al. |
| 8,343,190 B1 | 1/2013 | Mueller et al. |
| 8,349,012 B2 | 1/2013 | McKay |
| 8,353,826 B2 | 1/2013 | Weiman et al. |
| 8,361,108 B2 | 1/2013 | Gold et al. |
| 8,382,801 B2 | 2/2013 | Lamborne et al. |
| 8,388,660 B1 | 3/2013 | Abdou |
| 8,388,687 B2 | 3/2013 | Gimbel et al. |
| 8,397,522 B2 | 3/2013 | Springer et al. |
| 8,403,959 B2 | 3/2013 | Doellinger |
| 8,419,738 B2 | 4/2013 | Smisson, III et al. |
| 8,419,772 B2 | 4/2013 | Thompson et al. |
| 8,425,602 B2 | 4/2013 | Guyer et al. |
| 8,435,268 B2 | 5/2013 | Thompson et al. |
| 8,435,269 B2 | 5/2013 | Woolley et al. |
| 8,439,953 B2 | 5/2013 | Mitchell et al. |
| 8,454,621 B2 | 6/2013 | Deridder et al. |
| 8,454,661 B2 | 6/2013 | Rathbun et al. |
| 8,454,694 B2 | 6/2013 | Armstrong et al. |
| 8,465,547 B2 | 6/2013 | Melkent et al. |
| RE44,380 E | 7/2013 | De et al. |
| 8,475,497 B2 | 7/2013 | Grizzard |
| 8,480,712 B1 | 7/2013 | Samuel et al. |
| 8,480,747 B2 | 7/2013 | Melkent et al. |
| 8,486,147 B2 | 7/2013 | De et al. |
| 8,491,471 B2 | 7/2013 | Deshmukh et al. |
| 8,506,629 B2 | 8/2013 | Weiland |
| 8,512,343 B2 | 8/2013 | Dziedzic et al. |
| 8,529,611 B2 | 9/2013 | Champagne et al. |
| 8,562,650 B2 | 10/2013 | Dace |
| 8,574,267 B2 | 11/2013 | Linares |
| 8,603,143 B2 | 12/2013 | Robinson |
| 8,623,088 B1 | 1/2014 | Tohmeh et al. |
| 8,636,655 B1 | 1/2014 | Childs |
| 8,636,772 B2 | 1/2014 | Schmierer et al. |
| 8,657,855 B2 | 2/2014 | Zhang |
| 8,663,331 B2 | 3/2014 | McClellan, III et al. |
| 8,685,065 B1 | 4/2014 | Taber et al. |
| 8,685,093 B2 | 4/2014 | Anderson |
| 8,690,917 B2 | 4/2014 | Suh et al. |
| 8,690,950 B2 | 4/2014 | Refai et al. |
| 8,696,709 B2 | 4/2014 | Dinville et al. |
| 8,702,756 B2 | 4/2014 | Reimels |
| 8,721,686 B2 | 5/2014 | Gordon et al. |
| 8,721,689 B2 | 5/2014 | Butler et al. |
| 8,771,318 B2 | 7/2014 | Triplett et al. |
| 8,771,360 B2 | 7/2014 | Jimenez et al. |
| 8,795,335 B1 | 8/2014 | Abdou et al. |
| 8,795,375 B2 | 8/2014 | Malberg |
| 8,827,900 B1 | 9/2014 | Pimenta |
| 8,828,055 B2 | 9/2014 | Blain et al. |
| 8,828,056 B2 | 9/2014 | Buss et al. |
| 8,828,061 B2 | 9/2014 | Scrantz et al. |
| 8,845,728 B1 | 9/2014 | Abdou |
| 8,876,904 B2 | 11/2014 | Pimenta et al. |
| 8,900,137 B1 | 12/2014 | Lovell et al. |
| 8,906,092 B2 | 12/2014 | Abdou |
| 8,911,441 B2 | 12/2014 | Dace et al. |
| 8,940,019 B2 | 1/2015 | Gordon et al. |
| 8,940,051 B2 | 1/2015 | Gimbel et al. |
| 8,940,052 B2 | 1/2015 | Lechmann et al. |
| 8,956,415 B2 | 2/2015 | Cowan |
| 8,974,381 B1 | 3/2015 | Lovell et al. |
| 8,998,905 B2 | 4/2015 | Marik et al. |
| 9,005,248 B2 | 4/2015 | Taber et al. |
| 9,011,538 B2 | 4/2015 | Allard et al. |
| 9,044,280 B1 | 6/2015 | Arambula et al. |
| 9,113,853 B1 | 8/2015 | Casey et al. |
| 9,179,903 B2 | 11/2015 | Cianfrani et al. |
| 9,198,767 B2 | 12/2015 | Abdou |
| 9,211,147 B2 | 12/2015 | Gordon et al. |
| 9,247,968 B2 | 2/2016 | Taber et al. |
| 9,265,526 B1 | 2/2016 | Abdou |
| 9,308,099 B2 | 4/2016 | Triplett et al. |
| 9,320,506 B2 | 4/2016 | Bertagnoli et al. |
| 9,345,464 B2 | 5/2016 | Abdou et al. |
| 9,364,338 B2 | 6/2016 | Malberg |
| 9,408,596 B2 | 8/2016 | Blain |
| 9,408,717 B2 | 8/2016 | Perrow et al. |
| 9,445,918 B1 | 9/2016 | Lin et al. |
| 9,451,940 B2 | 9/2016 | Spann |
| 9,486,328 B2 | 11/2016 | Jimenez et al. |
| 9,622,795 B2 | 4/2017 | Reitblat et al. |
| 9,655,505 B1 | 5/2017 | Gharib et al. |
| 9,687,356 B1 | 6/2017 | Spangler et al. |
| 9,687,357 B2 | 6/2017 | Bannigan et al. |
| 9,730,737 B2 | 8/2017 | Baynham et al. |
| 9,730,802 B1 | 8/2017 | Harvey |
| 9,795,367 B1 | 10/2017 | Lee et al. |
| 9,795,370 B2 | 10/2017 | O'Connell et al. |
| RE46,647 E | 12/2017 | Messerli et al. |
| 10,166,018 B2 | 1/2019 | Hunt et al. |
| 10,426,450 B2 | 10/2019 | Vogel et al. |
| 2001/0001129 A1 | 5/2001 | McKay et al. |
| 2001/0012938 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2001/0047172 A1 | 11/2001 | Foley et al. |
| 2001/0053914 A1 | 12/2001 | Landry et al. |
| 2001/0056219 A1 | 12/2001 | Brauckman et al. |
| 2002/0016595 A1 | 2/2002 | Michelson |
| 2002/0019626 A1 | 2/2002 | Sharkey et al. |

(56) References Cited

U.S. PATENT DOCUMENTS

| | | |
|---|---|---|
| 2002/0019637 A1 | 2/2002 | Frey et al. |
| 2002/0026101 A1 | 2/2002 | Bookwalter et al. |
| 2002/0032484 A1 | 3/2002 | Hyde et al. |
| 2002/0045899 A1 | 4/2002 | Errico et al. |
| 2002/0045904 A1 | 4/2002 | Fuss et al. |
| 2002/0045945 A1 | 4/2002 | Liu et al. |
| 2002/0049394 A1 | 4/2002 | Roy et al. |
| 2002/0049444 A1 | 4/2002 | Knox |
| 2002/0049446 A1 | 4/2002 | Harkey et al. |
| 2002/0055738 A1 | 5/2002 | Lieberman |
| 2002/0055741 A1 | 5/2002 | Schlapfer et al. |
| 2002/0058944 A1 | 5/2002 | Michelson |
| 2002/0065558 A1 | 5/2002 | Varga et al. |
| 2002/0077530 A1 | 6/2002 | Velikaris et al. |
| 2002/0082602 A1 | 6/2002 | Biedermann et al. |
| 2002/0082700 A1 | 6/2002 | Bianchi et al. |
| 2002/0099386 A1 | 7/2002 | Beger et al. |
| 2002/0111628 A1 | 8/2002 | Ralph et al. |
| 2002/0120268 A1 | 8/2002 | Berger et al. |
| 2002/0128713 A1 | 9/2002 | Ferree |
| 2002/0138146 A1 | 9/2002 | Jackson |
| 2002/0143328 A1 | 10/2002 | Shluzas et al. |
| 2002/0143332 A1 | 10/2002 | Lin et al. |
| 2002/0143341 A1 | 10/2002 | Biedermann et al. |
| 2002/0147449 A1 | 10/2002 | Yun |
| 2002/0161368 A1 | 10/2002 | Foley et al. |
| 2002/0165550 A1 | 11/2002 | Frey et al. |
| 2002/0165612 A1 | 11/2002 | Gerber et al. |
| 2002/0169450 A1 | 11/2002 | Lange |
| 2002/0169453 A1 | 11/2002 | Berger |
| 2002/0183748 A1 | 12/2002 | Martin et al. |
| 2002/0183755 A1 | 12/2002 | Michelson |
| 2002/0183761 A1 | 12/2002 | Johnson et al. |
| 2002/0183848 A1 | 12/2002 | Ray et al. |
| 2002/0188296 A1 | 12/2002 | Michelson |
| 2003/0000350 A1 | 1/2003 | Zhao et al. |
| 2003/0004572 A1 | 1/2003 | Goble et al. |
| 2003/0014068 A1 | 1/2003 | Bonutti et al. |
| 2003/0014123 A1 | 1/2003 | Copf et al. |
| 2003/0018389 A1 | 1/2003 | Castro et al. |
| 2003/0023240 A1 | 1/2003 | Amrein et al. |
| 2003/0023243 A1 | 1/2003 | Biedermann et al. |
| 2003/0023305 A1 | 1/2003 | McKay |
| 2003/0023306 A1 | 1/2003 | Liu et al. |
| 2003/0023308 A1 | 1/2003 | Leroux et al. |
| 2003/0028251 A1* | 2/2003 | Mathews ............ A61B 17/025 623/17.16 |
| 2003/0040746 A1 | 2/2003 | Mitchell et al. |
| 2003/0040798 A1 | 2/2003 | Michelson |
| 2003/0045878 A1 | 3/2003 | Petit et al. |
| 2003/0045935 A1 | 3/2003 | Angelucci et al. |
| 2003/0055430 A1 | 3/2003 | Kim |
| 2003/0060826 A1 | 3/2003 | Foley et al. |
| 2003/0065330 A1 | 4/2003 | Zucherman et al. |
| 2003/0065395 A1 | 4/2003 | Ralph et al. |
| 2003/0065396 A1 | 4/2003 | Michelson |
| 2003/0073997 A1 | 4/2003 | Doubler et al. |
| 2003/0074001 A1 | 4/2003 | Apfelbaum et al. |
| 2003/0074005 A1 | 4/2003 | Roth et al. |
| 2003/0078583 A1 | 4/2003 | Biedermann et al. |
| 2003/0078662 A1 | 4/2003 | Ralph et al. |
| 2003/0078664 A1 | 4/2003 | Ralph et al. |
| 2003/0083747 A1 | 5/2003 | Winterbottom et al. |
| 2003/0088251 A1 | 5/2003 | Braun et al. |
| 2003/0093153 A1 | 5/2003 | Banick et al. |
| 2003/0094812 A1 | 5/2003 | Balsells |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0125742 A1 | 7/2003 | Yuan et al. |
| 2003/0139813 A1 | 7/2003 | Messerli et al. |
| 2003/0149341 A1 | 8/2003 | Clifton |
| 2003/0149431 A1 | 8/2003 | Varieur |
| 2003/0149432 A1 | 8/2003 | Frigg et al. |
| 2003/0149484 A1 | 8/2003 | Michelson |
| 2003/0153911 A1 | 8/2003 | Shluzas |
| 2003/0153913 A1 | 8/2003 | Altarac et al. |
| 2003/0163133 A1 | 8/2003 | Altarac et al. |
| 2003/0163199 A1 | 8/2003 | Boehm et al. |
| 2003/0167058 A1 | 9/2003 | Shluzas |
| 2003/0171749 A1 | 9/2003 | Le et al. |
| 2003/0171751 A1 | 9/2003 | Ritland |
| 2003/0176862 A1 | 9/2003 | Taylor et al. |
| 2003/0176864 A1 | 9/2003 | Ueyama et al. |
| 2003/0176923 A1 | 9/2003 | Keller et al. |
| 2003/0181975 A1 | 9/2003 | Ishii et al. |
| 2003/0187436 A1 | 10/2003 | Bolger et al. |
| 2003/0187510 A1 | 10/2003 | Hyde |
| 2003/0191470 A1 | 10/2003 | Ritland |
| 2003/0195518 A1 | 10/2003 | Cragg |
| 2003/0195633 A1 | 10/2003 | Hyde |
| 2003/0199873 A1 | 10/2003 | Richelsoph |
| 2003/0199981 A1 | 10/2003 | Ferree |
| 2003/0208202 A1 | 11/2003 | Falahee |
| 2003/0208203 A1 | 11/2003 | Lim et al. |
| 2003/0208204 A1 | 11/2003 | Bailey et al. |
| 2003/0208273 A1 | 11/2003 | Eisermann et al. |
| 2003/0212398 A1 | 11/2003 | Jackson |
| 2003/0216735 A1 | 11/2003 | Altarac et al. |
| 2003/0216736 A1 | 11/2003 | Robinson et al. |
| 2003/0217809 A1 | 11/2003 | Morishige |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229347 A1 | 12/2003 | Sherman et al. |
| 2003/0233136 A1 | 12/2003 | Williams et al. |
| 2003/0236472 A1 | 12/2003 | Van et al. |
| 2003/0236572 A1 | 12/2003 | Bertram |
| 2004/0002708 A1 | 1/2004 | Ritland |
| 2004/0006342 A1 | 1/2004 | Altarac et al. |
| 2004/0006391 A1 | 1/2004 | Reiley |
| 2004/0010253 A1 | 1/2004 | Morrison |
| 2004/0012938 A1 | 1/2004 | Sylvester et al. |
| 2004/0018228 A1 | 1/2004 | Fischell et al. |
| 2004/0019263 A1 | 1/2004 | Jutras et al. |
| 2004/0030338 A1 | 2/2004 | Paul |
| 2004/0030346 A1 | 2/2004 | Frey et al. |
| 2004/0039387 A1 | 2/2004 | Gause et al. |
| 2004/0044412 A1 | 3/2004 | Lambrecht et al. |
| 2004/0049189 A1 | 3/2004 | Le et al. |
| 2004/0049190 A1 | 3/2004 | Biedermann et al. |
| 2004/0049271 A1 | 3/2004 | Biedermann et al. |
| 2004/0049280 A1 | 3/2004 | Cauthen |
| 2004/0054412 A1 | 3/2004 | Gerbec et al. |
| 2004/0059318 A1 | 3/2004 | Zhang et al. |
| 2004/0068261 A1 | 4/2004 | Fourcault et al. |
| 2004/0068318 A1 | 4/2004 | Coates et al. |
| 2004/0073215 A1 | 4/2004 | Carli |
| 2004/0073216 A1 | 4/2004 | Lieberman |
| 2004/0078079 A1* | 4/2004 | Foley .................. A61B 17/025 623/17.11 |
| 2004/0078082 A1 | 4/2004 | Lange |
| 2004/0087947 A1 | 5/2004 | Lim et al. |
| 2004/0087948 A1 | 5/2004 | Suddaby |
| 2004/0087949 A1 | 5/2004 | Bono et al. |
| 2004/0087952 A1 | 5/2004 | Borgstrom et al. |
| 2004/0092930 A1 | 5/2004 | Petit et al. |
| 2004/0092933 A1 | 5/2004 | Shaolian et al. |
| 2004/0092934 A1 | 5/2004 | Howland |
| 2004/0093083 A1 | 5/2004 | Branch et al. |
| 2004/0097933 A1 | 5/2004 | Lourdel et al. |
| 2004/0097935 A1 | 5/2004 | Richelsoph et al. |
| 2004/0097940 A1 | 5/2004 | Paul |
| 2004/0098129 A1 | 5/2004 | Lin |
| 2004/0102780 A1 | 5/2004 | West et al. |
| 2004/0106927 A1 | 6/2004 | Ruffner et al. |
| 2004/0106995 A1 | 6/2004 | Le et al. |
| 2004/0106996 A1 | 6/2004 | Liu et al. |
| 2004/0111136 A1 | 6/2004 | Sharkey et al. |
| 2004/0111141 A1 | 6/2004 | Brabec et al. |
| 2004/0116929 A1 | 6/2004 | Barker et al. |
| 2004/0122518 A1 | 6/2004 | Rhoda |

(56) References Cited

U.S. PATENT DOCUMENTS

| | | |
|---|---|---|
| 2004/0127963 A1 | 7/2004 | Uchida et al. |
| 2004/0127990 A1 | 7/2004 | Bartish et al. |
| 2004/0127994 A1 | 7/2004 | Kast et al. |
| 2004/0133207 A1 | 7/2004 | Abdou |
| 2004/0138662 A1 | 7/2004 | Landry et al. |
| 2004/0138671 A1 | 7/2004 | Zander et al. |
| 2004/0143264 A1 | 7/2004 | McAfee |
| 2004/0143265 A1 | 7/2004 | Landry et al. |
| 2004/0143270 A1 | 7/2004 | Zucherman et al. |
| 2004/0143332 A1 | 7/2004 | Krueger et al. |
| 2004/0147928 A1 | 7/2004 | Landry et al. |
| 2004/0147929 A1 | 7/2004 | Biedermann et al. |
| 2004/0153065 A1 | 8/2004 | Lim |
| 2004/0153070 A1 | 8/2004 | Barker et al. |
| 2004/0158247 A1 | 8/2004 | Sitiso et al. |
| 2004/0158254 A1 | 8/2004 | Eisermann |
| 2004/0162558 A1 | 8/2004 | Hegde et al. |
| 2004/0162560 A1 | 8/2004 | Raynor et al. |
| 2004/0167520 A1 | 8/2004 | Zucherman et al. |
| 2004/0167625 A1 | 8/2004 | Beyar et al. |
| 2004/0167626 A1 | 8/2004 | Geremakis et al. |
| 2004/0172022 A1 | 9/2004 | Landry et al. |
| 2004/0172025 A1 | 9/2004 | Drewry et al. |
| 2004/0172134 A1 | 9/2004 | Berry |
| 2004/0176766 A1 | 9/2004 | Shluzas |
| 2004/0181226 A1 | 9/2004 | Michelson |
| 2004/0181285 A1 | 9/2004 | Simonson |
| 2004/0186473 A1 | 9/2004 | Cournoyer et al. |
| 2004/0186572 A1 | 9/2004 | Lange et al. |
| 2004/0193151 A1 | 9/2004 | To et al. |
| 2004/0195089 A1 | 10/2004 | O'Brien |
| 2004/0204712 A1 | 10/2004 | Kolb et al. |
| 2004/0204713 A1 | 10/2004 | Abdou |
| 2004/0210216 A1 | 10/2004 | Farris |
| 2004/0215190 A1 | 10/2004 | Nguyen et al. |
| 2004/0220567 A1 | 11/2004 | Eisermann et al. |
| 2004/0220670 A1 | 11/2004 | Eisermann et al. |
| 2004/0220671 A1 | 11/2004 | Ralph et al. |
| 2004/0225289 A1 | 11/2004 | Biedermann et al. |
| 2004/0225291 A1 | 11/2004 | Schwammberger et al. |
| 2004/0225364 A1 | 11/2004 | Richelsoph et al. |
| 2004/0225365 A1 | 11/2004 | Eisermann et al. |
| 2004/0225366 A1 | 11/2004 | Eisermann et al. |
| 2004/0230309 A1 | 11/2004 | DiMauro et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0236333 A1 | 11/2004 | Lin |
| 2004/0236425 A1 | 11/2004 | Huang |
| 2004/0243240 A1 | 12/2004 | Beaurain et al. |
| 2004/0249377 A1 | 12/2004 | Kaes et al. |
| 2004/0249379 A1 | 12/2004 | Winslow et al. |
| 2004/0249380 A1 | 12/2004 | Glascott |
| 2004/0249461 A1 | 12/2004 | Ferree |
| 2004/0254574 A1 | 12/2004 | Morrison et al. |
| 2004/0254575 A1 | 12/2004 | Obenchain et al. |
| 2004/0260283 A1 | 12/2004 | Wu et al. |
| 2004/0260291 A1 | 12/2004 | Jensen |
| 2004/0267264 A1 | 12/2004 | Konieczynski et al. |
| 2004/0267369 A1 | 12/2004 | Lyons et al. |
| 2005/0004573 A1 | 1/2005 | Abdou |
| 2005/0010227 A1 | 1/2005 | Paul |
| 2005/0010291 A1 | 1/2005 | Stinson et al. |
| 2005/0010301 A1 | 1/2005 | Disilvestro et al. |
| 2005/0012506 A1 | 1/2005 | Yudahira |
| 2005/0021029 A1 | 1/2005 | Trieu et al. |
| 2005/0021031 A1 | 1/2005 | Foley et al. |
| 2005/0021040 A1 | 1/2005 | Bertagnoli |
| 2005/0021041 A1 | 1/2005 | Michelson |
| 2005/0027296 A1 | 2/2005 | Thramann et al. |
| 2005/0027360 A1 | 2/2005 | Webb et al. |
| 2005/0033296 A1 | 2/2005 | Bono et al. |
| 2005/0033298 A1 | 2/2005 | Hawkes et al. |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0038432 A1 | 2/2005 | Shaolian et al. |
| 2005/0038511 A1 | 2/2005 | Martz et al. |
| 2005/0043800 A1 | 2/2005 | Paul et al. |
| 2005/0043802 A1 | 2/2005 | Eisermann et al. |
| 2005/0049705 A1 | 3/2005 | Hale et al. |
| 2005/0049708 A1 | 3/2005 | Atkinson et al. |
| 2005/0055026 A1 | 3/2005 | Biedermann et al. |
| 2005/0055031 A1 | 3/2005 | Lim |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin et al. |
| 2005/0069701 A1 | 3/2005 | Watanabe et al. |
| 2005/0070899 A1 | 3/2005 | Doubler et al. |
| 2005/0070901 A1 | 3/2005 | David |
| 2005/0071007 A1 | 3/2005 | Malek |
| 2005/0075636 A1 | 4/2005 | Gotzen |
| 2005/0080320 A1 | 4/2005 | Lee et al. |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0085909 A1 | 4/2005 | Eisermann |
| 2005/0096652 A1 | 5/2005 | Burton |
| 2005/0096653 A1 | 5/2005 | Doubler et al. |
| 2005/0096654 A1 | 5/2005 | Lin |
| 2005/0096745 A1 | 5/2005 | Andre et al. |
| 2005/0107788 A1 | 5/2005 | Beaurain et al. |
| 2005/0113830 A1 | 5/2005 | Rezach et al. |
| 2005/0113833 A1 | 5/2005 | Davison |
| 2005/0113927 A1 | 5/2005 | Malek |
| 2005/0113928 A1 | 5/2005 | Cragg et al. |
| 2005/0119663 A1 | 6/2005 | Keyer et al. |
| 2005/0119747 A1 | 6/2005 | Fabris et al. |
| 2005/0119748 A1 | 6/2005 | Reiley et al. |
| 2005/0124991 A1 | 6/2005 | Jahng |
| 2005/0125061 A1 | 6/2005 | Zucherman et al. |
| 2005/0125066 A1 | 6/2005 | McAfee |
| 2005/0126576 A1 | 6/2005 | Ferree |
| 2005/0131404 A1 | 6/2005 | Mazda et al. |
| 2005/0131406 A1 | 6/2005 | Reiley et al. |
| 2005/0131407 A1 | 6/2005 | Sicvol et al. |
| 2005/0131409 A1 | 6/2005 | Chervitz et al. |
| 2005/0131413 A1 | 6/2005 | O'Driscoll et al. |
| 2005/0131420 A1 | 6/2005 | Techiera et al. |
| 2005/0131421 A1 | 6/2005 | Anderson et al. |
| 2005/0137597 A1 | 6/2005 | Butler et al. |
| 2005/0137604 A1 | 6/2005 | Assell et al. |
| 2005/0143737 A1 | 6/2005 | Pafford et al. |
| 2005/0143822 A1 | 6/2005 | Paul |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149188 A1 | 7/2005 | Cook et al. |
| 2005/0149196 A1 | 7/2005 | Zucherman et al. |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0154461 A1 | 7/2005 | Humphreys et al. |
| 2005/0159750 A1 | 7/2005 | Doherty |
| 2005/0159756 A1 | 7/2005 | Ray |
| 2005/0159813 A1 | 7/2005 | Molz et al. |
| 2005/0159815 A1 | 7/2005 | Kamimura et al. |
| 2005/0165396 A1 | 7/2005 | Fortin et al. |
| 2005/0165398 A1 | 7/2005 | Reiley |
| 2005/0165400 A1 | 7/2005 | Fernandez et al. |
| 2005/0165487 A1 | 7/2005 | Muhanna et al. |
| 2005/0171540 A1 | 8/2005 | Lim et al. |
| 2005/0171541 A1 | 8/2005 | Boehm et al. |
| 2005/0171543 A1 | 8/2005 | Timm et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177163 A1 | 8/2005 | Abdou et al. |

(56) References Cited

U.S. PATENT DOCUMENTS

| | | |
|---|---|---|
| 2005/0177164 A1 | 8/2005 | Walters et al. |
| 2005/0177166 A1 | 8/2005 | Timm et al. |
| 2005/0177167 A1 | 8/2005 | Muckter et al. |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0177240 A1 | 8/2005 | Blain |
| 2005/0182401 A1 | 8/2005 | Timm et al. |
| 2005/0182404 A1 | 8/2005 | Lauryssen et al. |
| 2005/0187548 A1 | 8/2005 | Butler et al. |
| 2005/0187555 A1 | 8/2005 | Biedermann et al. |
| 2005/0187628 A1 | 8/2005 | Michelson |
| 2005/0192571 A1 | 9/2005 | Abdelgany |
| 2005/0192577 A1 | 9/2005 | Mosca et al. |
| 2005/0192580 A1 | 9/2005 | Dalton |
| 2005/0192589 A1 | 9/2005 | Raymond et al. |
| 2005/0192671 A1 | 9/2005 | Bao et al. |
| 2005/0197660 A1 | 9/2005 | Haid et al. |
| 2005/0197702 A1 | 9/2005 | Coppes et al. |
| 2005/0203511 A1 | 9/2005 | Wilson-MacDonald et al. |
| 2005/0203512 A1 | 9/2005 | Hawkins et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0203533 A1 | 9/2005 | Ferguson et al. |
| 2005/0203604 A1 | 9/2005 | Brabec et al. |
| 2005/0203624 A1 | 9/2005 | Serhan et al. |
| 2005/0209694 A1 | 9/2005 | Loeb |
| 2005/0215999 A1 | 9/2005 | Birkmeyer et al. |
| 2005/0216001 A1 | 9/2005 | David |
| 2005/0216003 A1 | 9/2005 | Biedermann et al. |
| 2005/0216083 A1 | 9/2005 | Michelson |
| 2005/0222682 A1 | 10/2005 | Link et al. |
| 2005/0222683 A1 | 10/2005 | Berry |
| 2005/0228376 A1 | 10/2005 | Boomer et al. |
| 2005/0228377 A1 | 10/2005 | Chao et al. |
| 2005/0228395 A1 | 10/2005 | Auxepaules et al. |
| 2005/0228400 A1 | 10/2005 | Chao et al. |
| 2005/0228501 A1 | 10/2005 | Miller et al. |
| 2005/0234449 A1 | 10/2005 | Aferzon |
| 2005/0234450 A1 | 10/2005 | Barker et al. |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234555 A1 | 10/2005 | Sutton et al. |
| 2005/0240181 A1 | 10/2005 | Boomer et al. |
| 2005/0240183 A1 | 10/2005 | Vaughan |
| 2005/0240265 A1 | 10/2005 | Kuiper et al. |
| 2005/0240273 A1 | 10/2005 | Khandkar et al. |
| 2005/0245928 A1 | 11/2005 | Colleran et al. |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0251258 A1 | 11/2005 | Jackson |
| 2005/0256576 A1 | 11/2005 | Moskowitz et al. |
| 2005/0256578 A1 | 11/2005 | Blatt et al. |
| 2005/0260058 A1 | 11/2005 | Cassagne, III |
| 2005/0261685 A1 | 11/2005 | Fortin et al. |
| 2005/0261687 A1 | 11/2005 | Garamszegi et al. |
| 2005/0261768 A1 | 11/2005 | Trieu |
| 2005/0267470 A1 | 12/2005 | McBride |
| 2005/0267471 A1 | 12/2005 | Biedermann et al. |
| 2005/0267474 A1 | 12/2005 | Dalton |
| 2005/0267477 A1 | 12/2005 | Jackson |
| 2005/0267579 A1 | 12/2005 | Reiley et al. |
| 2005/0267580 A1 | 12/2005 | Suddaby |
| 2005/0273099 A1 | 12/2005 | Baccelli et al. |
| 2005/0273101 A1 | 12/2005 | Schumacher |
| 2005/0273120 A1 | 12/2005 | Abdou et al. |
| 2005/0273171 A1 | 12/2005 | Gordon et al. |
| 2005/0277919 A1 | 12/2005 | Slivka et al. |
| 2005/0277921 A1 | 12/2005 | Eisermann et al. |
| 2005/0277922 A1 | 12/2005 | Trieu et al. |
| 2005/0277923 A1 | 12/2005 | Sweeney |
| 2005/0277924 A1 | 12/2005 | Roychowdhury |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278026 A1 | 12/2005 | Gordon et al. |
| 2005/0283152 A1 | 12/2005 | Lindemann et al. |
| 2005/0283153 A1 | 12/2005 | Poyner et al. |
| 2005/0283157 A1 | 12/2005 | Coates et al. |
| 2005/0283236 A1 | 12/2005 | Razian |
| 2005/0283238 A1 | 12/2005 | Reiley |
| 2005/0283241 A1 | 12/2005 | Keller et al. |
| 2005/0283244 A1 | 12/2005 | Gordon et al. |
| 2005/0283245 A1 | 12/2005 | Gordon et al. |
| 2005/0288669 A1 | 12/2005 | Abdou et al. |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0004367 A1* | 1/2006 | Alamin .............. A61B 17/7064 606/74 |
| 2006/0004453 A1 | 1/2006 | Bartish et al. |
| 2006/0009767 A1 | 1/2006 | Kiester et al. |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0015181 A1 | 1/2006 | Elberg |
| 2006/0015183 A1 | 1/2006 | Gilbert et al. |
| 2006/0020342 A1 | 1/2006 | Ferree et al. |
| 2006/0024614 A1 | 2/2006 | Williamson et al. |
| 2006/0025767 A1 | 2/2006 | Khalili et al. |
| 2006/0025768 A1 | 2/2006 | Iott et al. |
| 2006/0025770 A1 | 2/2006 | Schlapfer et al. |
| 2006/0030839 A1 | 2/2006 | Park et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036250 A1* | 2/2006 | Lange ................ A61B 17/7044 606/71 |
| 2006/0036252 A1 | 2/2006 | Baynham et al. |
| 2006/0036254 A1 | 2/2006 | Lim |
| 2006/0036255 A1 | 2/2006 | Pond, Jr. et al. |
| 2006/0036256 A1 | 2/2006 | Carl et al. |
| 2006/0036258 A1 | 2/2006 | Zucherman et al. |
| 2006/0036259 A1 | 2/2006 | Carl et al. |
| 2006/0036260 A1 | 2/2006 | Runco et al. |
| 2006/0036323 A1* | 2/2006 | Carl .................... A61B 17/7064 623/17.11 |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0052870 A1 | 3/2006 | Ferree |
| 2006/0052872 A1 | 3/2006 | Studer et al. |
| 2006/0058788 A1 | 3/2006 | Hammer et al. |
| 2006/0058790 A1 | 3/2006 | Carl et al. |
| 2006/0058791 A1 | 3/2006 | Broman et al. |
| 2006/0058800 A1 | 3/2006 | Ainsworth et al. |
| 2006/0058878 A1 | 3/2006 | Michelson |

(56) References Cited

U.S. PATENT DOCUMENTS

| | | |
|---|---|---|
| 2006/0064090 A1 | 3/2006 | Park |
| 2006/0064091 A1 | 3/2006 | Ludwig et al. |
| 2006/0064092 A1 | 3/2006 | Howland |
| 2006/0064095 A1 | 3/2006 | Senn et al. |
| 2006/0069390 A1 | 3/2006 | Frigg et al. |
| 2006/0069436 A1 | 3/2006 | Sutton et al. |
| 2006/0069438 A1 | 3/2006 | Zucherman et al. |
| 2006/0074419 A1 | 4/2006 | Taylor et al. |
| 2006/0074445 A1 | 4/2006 | Gerber et al. |
| 2006/0074488 A1 | 4/2006 | Abdou et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth et al. |
| 2006/0079899 A1 | 4/2006 | Ritland |
| 2006/0079903 A1 | 4/2006 | Wong |
| 2006/0079905 A1 | 4/2006 | Beyar et al. |
| 2006/0084844 A1 | 4/2006 | Nehls |
| 2006/0084976 A1 | 4/2006 | Borgstrom et al. |
| 2006/0084977 A1 | 4/2006 | Lieberman |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084986 A1 | 4/2006 | Grinberg et al. |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom et al. |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085076 A1 | 4/2006 | Krishna et al. |
| 2006/0088398 A1 | 4/2006 | Lund |
| 2006/0089643 A1 | 4/2006 | Mujwid |
| 2006/0089644 A1 | 4/2006 | Felix |
| 2006/0089646 A1 | 4/2006 | Bonutti |
| 2006/0089647 A1 | 4/2006 | Culbert et al. |
| 2006/0089656 A1 | 4/2006 | Allard et al. |
| 2006/0089718 A1 | 4/2006 | Zucherman et al. |
| 2006/0095037 A1 | 5/2006 | Jones et al. |
| 2006/0106380 A1 | 5/2006 | Colleran et al. |
| 2006/0106381 A1 | 5/2006 | Ferree et al. |
| 2006/0106383 A1 | 5/2006 | Biedermann et al. |
| 2006/0106387 A1 | 5/2006 | Fanger et al. |
| 2006/0106395 A1 | 5/2006 | Link et al. |
| 2006/0106397 A1 | 5/2006 | Lins et al. |
| 2006/0111714 A1 | 5/2006 | Foley |
| 2006/0111715 A1 | 5/2006 | Jackson |
| 2006/0111728 A1 | 5/2006 | Abdou et al. |
| 2006/0116677 A1 | 6/2006 | Burd et al. |
| 2006/0116768 A1 | 6/2006 | Krueger et al. |
| 2006/0122597 A1 | 6/2006 | Jones et al. |
| 2006/0122599 A1 | 6/2006 | Drewry et al. |
| 2006/0122604 A1 | 6/2006 | Gorhan et al. |
| 2006/0122607 A1 | 6/2006 | Kolb et al. |
| 2006/0122625 A1 | 6/2006 | Truckai et al. |
| 2006/0122701 A1 | 6/2006 | Kiester |
| 2006/0129147 A1 | 6/2006 | Biedermann et al. |
| 2006/0129149 A1 | 6/2006 | Iott et al. |
| 2006/0129239 A1 | 6/2006 | Kwak et al. |
| 2006/0129244 A1 | 6/2006 | Ensign |
| 2006/0136060 A1 | 6/2006 | Taylor |
| 2006/0136062 A1 | 6/2006 | Dinello et al. |
| 2006/0142758 A1 | 6/2006 | Petit |
| 2006/0142760 A1 | 6/2006 | McDonnell |
| 2006/0142761 A1 | 6/2006 | Landry et al. |
| 2006/0142858 A1 | 6/2006 | Colleran et al. |
| 2006/0149228 A1 | 7/2006 | Schlapfer et al. |
| 2006/0149229 A1 | 7/2006 | Kwak et al. |
| 2006/0149232 A1 | 7/2006 | Sasing |
| 2006/0149234 A1 | 7/2006 | De |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149244 A1 | 7/2006 | Amrein et al. |
| 2006/0149245 A1 | 7/2006 | Sweeney |
| 2006/0149278 A1 | 7/2006 | Abdou |
| 2006/0149284 A1 | 7/2006 | McCormack et al. |
| 2006/0149385 A1 | 7/2006 | McKay |
| 2006/0155277 A1 | 7/2006 | Metz-Stavenhagen |
| 2006/0155278 A1 | 7/2006 | Warnick |
| 2006/0155284 A1 | 7/2006 | Doherty et al. |
| 2006/0161152 A1 | 7/2006 | Ensign et al. |
| 2006/0161154 A1 | 7/2006 | McAfee |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0178746 A1 | 8/2006 | Bartish et al. |
| 2006/0184112 A1 | 8/2006 | Horn et al. |
| 2006/0184171 A1 | 8/2006 | Biedermann et al. |
| 2006/0184180 A1 | 8/2006 | Augostino et al. |
| 2006/0184247 A1 | 8/2006 | Edidin et al. |
| 2006/0187562 A1 | 8/2006 | Mounnarat et al. |
| 2006/0189983 A1 | 8/2006 | Fallin et al. |
| 2006/0189984 A1 | 8/2006 | Fallin et al. |
| 2006/0189985 A1 | 8/2006 | Lewis |
| 2006/0190082 A1 | 8/2006 | Keller et al. |
| 2006/0195089 A1 | 8/2006 | LeHuec et al. |
| 2006/0195090 A1 | 8/2006 | Suddaby |
| 2006/0195093 A1 | 8/2006 | Jahng |
| 2006/0195096 A1 | 8/2006 | Lee et al. |
| 2006/0195098 A1 | 8/2006 | Schumacher |
| 2006/0195102 A1 | 8/2006 | Malandain |
| 2006/0195192 A1 | 8/2006 | Gordon et al. |
| 2006/0200121 A1 | 9/2006 | Mowery |
| 2006/0200128 A1 | 9/2006 | Mueller |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson et al. |
| 2006/0200139 A1 | 9/2006 | Michelson et al. |
| 2006/0200149 A1 | 9/2006 | Hoy et al. |
| 2006/0210494 A1 | 9/2006 | Rabiei et al. |
| 2006/0212033 A1 | 9/2006 | Rothman et al. |
| 2006/0212034 A1 | 9/2006 | Triplett et al. |
| 2006/0217710 A1 | 9/2006 | Abdou |
| 2006/0217712 A1 | 9/2006 | Mueller et al. |
| 2006/0217713 A1 | 9/2006 | Serhan et al. |
| 2006/0217714 A1 | 9/2006 | Serhan et al. |
| 2006/0217716 A1 | 9/2006 | Baker et al. |
| 2006/0217719 A1 | 9/2006 | Albert et al. |
| 2006/0217731 A1 | 9/2006 | Gil et al. |
| 2006/0217809 A1 | 9/2006 | Albert et al. |
| 2006/0224159 A1 | 10/2006 | Anderson et al. |
| 2006/0229608 A1 | 10/2006 | Foster et al. |
| 2006/0229609 A1 | 10/2006 | Wang |
| 2006/0229610 A1 | 10/2006 | Piehl |
| 2006/0229612 A1 | 10/2006 | Rothman et al. |
| 2006/0229613 A1 | 10/2006 | Timm et al. |
| 2006/0229614 A1 | 10/2006 | Foley et al. |
| 2006/0229615 A1 | 10/2006 | Abdou et al. |
| 2006/0229627 A1 | 10/2006 | Hunt et al. |
| 2006/0229715 A1 | 10/2006 | Istephanous et al. |
| 2006/0229729 A1 | 10/2006 | Gordon et al. |
| 2006/0235387 A1 | 10/2006 | Peterman |
| 2006/0235389 A1 | 10/2006 | Albert et al. |
| 2006/0235391 A1 | 10/2006 | Sutterlin, III et al. |
| 2006/0235392 A1 | 10/2006 | Hammer et al. |
| 2006/0235393 A1 | 10/2006 | Bono et al. |
| 2006/0235403 A1 | 10/2006 | Blain |
| 2006/0235411 A1 | 10/2006 | Blain et al. |
| 2006/0235414 A1 | 10/2006 | Lim et al. |
| 2006/0235532 A1 | 10/2006 | Meunier et al. |
| 2006/0241593 A1 | 10/2006 | Sherman et al. |
| 2006/0241595 A1 | 10/2006 | Molz et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241610 A1 | 10/2006 | Lim et al. |
| 2006/0241614 A1 | 10/2006 | Bruneau et al. |

(56) References Cited

U.S. PATENT DOCUMENTS

| | | |
|---|---|---|
| 2006/0241615 A1 | 10/2006 | Melkent |
| 2006/0241641 A1 | 10/2006 | Albans et al. |
| 2006/0241761 A1 | 10/2006 | Gately |
| 2006/0241769 A1 | 10/2006 | Gordon et al. |
| 2006/0241771 A1 | 10/2006 | Gordon et al. |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247634 A1 | 11/2006 | Warner et al. |
| 2006/0247635 A1 | 11/2006 | Gordon et al. |
| 2006/0247636 A1 | 11/2006 | Yuan et al. |
| 2006/0247637 A1 | 11/2006 | Colleran et al. |
| 2006/0247640 A1 | 11/2006 | Blackwell et al. |
| 2006/0247655 A1 | 11/2006 | Francis et al. |
| 2006/0247679 A1 | 11/2006 | Peterman |
| 2006/0247772 A1 | 11/2006 | McKay |
| 2006/0247778 A1 | 11/2006 | Ferree et al. |
| 2006/0247779 A1 | 11/2006 | Gordon et al. |
| 2006/0247782 A1 | 11/2006 | Molz et al. |
| 2006/0253198 A1* | 11/2006 | Myint .................... A61F 2/441 623/17.12 |
| 2006/0253201 A1 | 11/2006 | McLuen |
| 2006/0264933 A1 | 11/2006 | Baker et al. |
| 2006/0264934 A1 | 11/2006 | Fallin et al. |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmann |
| 2006/0264942 A1 | 11/2006 | Lim et al. |
| 2006/0264962 A1 | 11/2006 | Chin et al. |
| 2006/0265077 A1 | 11/2006 | Zwirkoski |
| 2006/0269940 A1 | 11/2006 | Li et al. |
| 2006/0271046 A1 | 11/2006 | Kwak et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0276793 A1 | 12/2006 | Berry |
| 2006/0276803 A1 | 12/2006 | Salerni |
| 2006/0276900 A1 | 12/2006 | Carpenter |
| 2006/0282074 A1 | 12/2006 | Renaud et al. |
| 2006/0282075 A1 | 12/2006 | Labrom et al. |
| 2006/0282076 A1 | 12/2006 | Labrom et al. |
| 2006/0282078 A1 | 12/2006 | Labrom et al. |
| 2006/0282079 A1 | 12/2006 | Labrom et al. |
| 2006/0287583 A1 | 12/2006 | Mangiardi |
| 2006/0293662 A1 | 12/2006 | Boyer et al. |
| 2007/0016218 A1 | 1/2007 | Winslow et al. |
| 2007/0016298 A1* | 1/2007 | Recoules-Arche ... A61F 2/4455 623/17.11 |
| 2007/0021836 A1 | 1/2007 | Doty |
| 2007/0027542 A1 | 2/2007 | Xu |
| 2007/0032790 A1 | 2/2007 | Aschmann et al. |
| 2007/0039837 A1 | 2/2007 | Hanina et al. |
| 2007/0043356 A1 | 2/2007 | Timm et al. |
| 2007/0043442 A1 | 2/2007 | Abernathie et al. |
| 2007/0049935 A1 | 3/2007 | Edidin et al. |
| 2007/0050030 A1 | 3/2007 | Kim |
| 2007/0050032 A1 | 3/2007 | Gittings et al. |
| 2007/0055236 A1 | 3/2007 | Hudgins et al. |
| 2007/0055377 A1 | 3/2007 | Hanson et al. |
| 2007/0067035 A1 | 3/2007 | Falahee |
| 2007/0083266 A1 | 4/2007 | Lang |
| 2007/0090238 A1 | 4/2007 | Justis |
| 2007/0093817 A1 | 4/2007 | Barrus et al. |
| 2007/0093823 A1 | 4/2007 | Booth et al. |
| 2007/0093825 A1 | 4/2007 | Ferree et al. |
| 2007/0093828 A1 | 4/2007 | Abdou et al. |
| 2007/0093829 A1 | 4/2007 | Abdou et al. |
| 2007/0093901 A1 | 4/2007 | Grotz et al. |
| 2007/0100212 A1 | 5/2007 | Pimenta |
| 2007/0100340 A1 | 5/2007 | Lange et al. |
| 2007/0100341 A1 | 5/2007 | Reglos et al. |
| 2007/0106298 A1 | 5/2007 | Carli et al. |
| 2007/0106383 A1 | 5/2007 | Abdou et al. |
| 2007/0108383 A1 | 5/2007 | Combes et al. |
| 2007/0118121 A1 | 5/2007 | Purcell et al. |
| 2007/0118122 A1 | 5/2007 | Butler et al. |
| 2007/0118123 A1 | 5/2007 | Strausbaugh et al. |
| 2007/0118132 A1 | 5/2007 | Culbert et al. |
| 2007/0123867 A1 | 5/2007 | Kirschman |
| 2007/0123869 A1 | 5/2007 | Chin et al. |
| 2007/0123884 A1 | 5/2007 | Abdou |
| 2007/0129804 A1 | 6/2007 | Bentley et al. |
| 2007/0142916 A1 | 6/2007 | Olson, Jr. et al. |
| 2007/0149978 A1 | 6/2007 | Shezifi et al. |
| 2007/0151116 A1 | 7/2007 | Malandain |
| 2007/0161962 A1 | 7/2007 | Edie et al. |
| 2007/0161992 A1 | 7/2007 | Kwak et al. |
| 2007/0162000 A1 | 7/2007 | Perkins |
| 2007/0162001 A1 | 7/2007 | Chin et al. |
| 2007/0162005 A1 | 7/2007 | Peterson et al. |
| 2007/0162127 A1 | 7/2007 | Peterman et al. |
| 2007/0162133 A1 | 7/2007 | Doubler et al. |
| 2007/0162138 A1 | 7/2007 | Heinz |
| 2007/0167948 A1 | 7/2007 | Abdou et al. |
| 2007/0168036 A1 | 7/2007 | Ainsworth et al. |
| 2007/0173831 A1 | 7/2007 | Abdou |
| 2007/0173842 A1 | 7/2007 | Abdou |
| 2007/0179493 A1 | 8/2007 | Kim |
| 2007/0179500 A1 | 8/2007 | Chin et al. |
| 2007/0179614 A1 | 8/2007 | Heinz et al. |
| 2007/0185367 A1 | 8/2007 | Abdou et al. |
| 2007/0185376 A1 | 8/2007 | Wilson et al. |
| 2007/0185489 A1 | 8/2007 | Abdou |
| 2007/0191834 A1 | 8/2007 | Bruneau et al. |
| 2007/0191861 A1 | 8/2007 | Allard et al. |
| 2007/0191946 A1 | 8/2007 | Heinz et al. |
| 2007/0191951 A1 | 8/2007 | Branch et al. |
| 2007/0191958 A1 | 8/2007 | Abdou et al. |
| 2007/0198090 A1 | 8/2007 | Abdou |
| 2007/0208227 A1 | 9/2007 | Smith et al. |
| 2007/0213597 A1 | 9/2007 | Wooster |
| 2007/0213732 A1 | 9/2007 | Khanna et al. |
| 2007/0225724 A1 | 9/2007 | Edmond et al. |
| 2007/0225726 A1 | 9/2007 | Dye et al. |
| 2007/0225807 A1 | 9/2007 | Phan et al. |
| 2007/0225808 A1 | 9/2007 | Warnick |
| 2007/0225812 A1 | 9/2007 | Gill |
| 2007/0233074 A1 | 10/2007 | Anderson et al. |
| 2007/0233077 A1 | 10/2007 | Khalili |
| 2007/0233082 A1 | 10/2007 | Chin et al. |
| 2007/0233083 A1 | 10/2007 | Abdou et al. |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233118 A1 | 10/2007 | McLain |
| 2007/0233129 A1 | 10/2007 | Bertagnoli et al. |
| 2007/0233247 A1 | 10/2007 | Schwab |
| 2007/0233251 A1 | 10/2007 | Abdou |
| 2007/0255389 A1 | 11/2007 | Oberti et al. |
| 2007/0255415 A1 | 11/2007 | Edie et al. |
| 2007/0270812 A1 | 11/2007 | Peckham |
| 2007/0270813 A1 | 11/2007 | Garamszegi |
| 2007/0270824 A1 | 11/2007 | Lim et al. |
| 2007/0270827 A1 | 11/2007 | Lim et al. |
| 2007/0270838 A1 | 11/2007 | Bruneau et al. |
| 2007/0270840 A1 | 11/2007 | Chin et al. |
| 2007/0270874 A1 | 11/2007 | Anderson |
| 2007/0270963 A1 | 11/2007 | Melkent et al. |
| 2007/0270968 A1 | 11/2007 | Baynham et al. |
| 2007/0274772 A1 | 11/2007 | Tiberghien et al. |
| 2007/0276370 A1 | 11/2007 | Altarac et al. |
| 2007/0282448 A1 | 12/2007 | Abdou |
| 2007/0293949 A1 | 12/2007 | Salerni et al. |
| 2007/0299445 A1 | 12/2007 | Shadduck et al. |
| 2007/0299521 A1 | 12/2007 | Glenn et al. |
| 2008/0009880 A1 | 1/2008 | Warnick et al. |
| 2008/0015580 A1 | 1/2008 | Chao |
| 2008/0015597 A1 | 1/2008 | Whipple |
| 2008/0015698 A1 | 1/2008 | Marino et al. |
| 2008/0021466 A1 | 1/2008 | Shadduck et al. |

(56) References Cited

U.S. PATENT DOCUMENTS

| | | |
|---|---|---|
| 2008/0021559 A1 | 1/2008 | Thramann |
| 2008/0027432 A1 | 1/2008 | Strauss et al. |
| 2008/0027438 A1 | 1/2008 | Abdou et al. |
| 2008/0027458 A1 | 1/2008 | Aikins et al. |
| 2008/0027544 A1 | 1/2008 | Melkent |
| 2008/0027545 A1 | 1/2008 | Zucherman et al. |
| 2008/0027550 A1 | 1/2008 | Link et al. |
| 2008/0039837 A1 | 2/2008 | Gambale |
| 2008/0039843 A1 | 2/2008 | Abdou |
| 2008/0045963 A1 | 2/2008 | Abdou et al. |
| 2008/0045968 A1 | 2/2008 | Yu et al. |
| 2008/0045983 A1 | 2/2008 | To et al. |
| 2008/0051783 A1 | 2/2008 | Null et al. |
| 2008/0051896 A1 | 2/2008 | Suddaby |
| 2008/0058810 A1 | 3/2008 | Abdou |
| 2008/0065219 A1 | 3/2008 | Dye |
| 2008/0065222 A1 | 3/2008 | Hamada |
| 2008/0081951 A1 | 4/2008 | Frasier et al. |
| 2008/0086080 A1 | 4/2008 | Mastri et al. |
| 2008/0091211 A1 | 4/2008 | Gately |
| 2008/0108993 A1 | 5/2008 | Bennett et al. |
| 2008/0114401 A1 | 5/2008 | Liu et al. |
| 2008/0114455 A1 | 5/2008 | Lange et al. |
| 2008/0119853 A1 | 5/2008 | Felt et al. |
| 2008/0119935 A1 | 5/2008 | Alvarez |
| 2008/0125813 A1 | 5/2008 | Erickson et al. |
| 2008/0125865 A1 | 5/2008 | Abdelgany et al. |
| 2008/0126813 A1 | 5/2008 | Kawakami |
| 2008/0132951 A1 | 6/2008 | Reiley et al. |
| 2008/0133012 A1 | 6/2008 | McGuckin et al. |
| 2008/0133014 A1 | 6/2008 | Gately et al. |
| 2008/0133016 A1 | 6/2008 | Heinz |
| 2008/0133017 A1 | 6/2008 | Beyar et al. |
| 2008/0139879 A1 | 6/2008 | Olson et al. |
| 2008/0140085 A1 | 6/2008 | Gately et al. |
| 2008/0140125 A1 | 6/2008 | Mitchell et al. |
| 2008/0140204 A1 | 6/2008 | Heinz |
| 2008/0140207 A1 | 6/2008 | Olmos et al. |
| 2008/0147123 A1 | 6/2008 | Schermerhorn |
| 2008/0147190 A1 | 6/2008 | Dewey et al. |
| 2008/0154308 A1 | 6/2008 | Sherman et al. |
| 2008/0154374 A1 | 6/2008 | Labrom |
| 2008/0161818 A1 | 7/2008 | Kloss et al. |
| 2008/0161821 A1 | 7/2008 | Heinz |
| 2008/0161853 A1 | 7/2008 | Arnold et al. |
| 2008/0161856 A1 | 7/2008 | Liu et al. |
| 2008/0167655 A1 | 7/2008 | Wang et al. |
| 2008/0167657 A1 | 7/2008 | Greenhalgh |
| 2008/0177271 A1 | 7/2008 | Yeh |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0177326 A1 | 7/2008 | Thompson |
| 2008/0177391 A1 | 7/2008 | Mitchell et al. |
| 2008/0183204 A1 | 7/2008 | Greenhalgh et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0188898 A1 | 8/2008 | Jackson |
| 2008/0188941 A1 | 8/2008 | Grotz |
| 2008/0195152 A1 | 8/2008 | Altarac et al. |
| 2008/0234735 A1 | 9/2008 | Joshi |
| 2008/0243185 A1 | 10/2008 | Felix et al. |
| 2008/0243186 A1 | 10/2008 | Abdou |
| 2008/0243188 A1 | 10/2008 | Walder et al. |
| 2008/0243189 A1 | 10/2008 | Purcell et al. |
| 2008/0249628 A1 | 10/2008 | Altarac et al. |
| 2008/0262318 A1 | 10/2008 | Gorek et al. |
| 2008/0262554 A1 | 10/2008 | Hayes et al. |
| 2008/0269904 A1 | 10/2008 | Voorhies |
| 2008/0281346 A1 | 11/2008 | Greenhalgh et al. |
| 2008/0281358 A1 | 11/2008 | Abdou et al. |
| 2008/0281359 A1 | 11/2008 | Abdou et al. |
| 2008/0288073 A1 | 11/2008 | Renganath et al. |
| 2008/0294199 A1 | 11/2008 | Kohm et al. |
| 2008/0294200 A1 | 11/2008 | Kohm et al. |
| 2008/0300598 A1 | 12/2008 | Barreiro et al. |
| 2008/0300685 A1 | 12/2008 | Carls et al. |
| 2008/0300686 A1 | 12/2008 | Khoo |
| 2008/0306601 A1 | 12/2008 | Dreyfuss |
| 2008/0312655 A1 | 12/2008 | Kirschman et al. |
| 2008/0312692 A1 | 12/2008 | Brennan et al. |
| 2008/0312741 A1 | 12/2008 | Lee et al. |
| 2008/0312743 A1 | 12/2008 | Vila et al. |
| 2008/0319487 A1 | 12/2008 | Fielding et al. |
| 2008/0319549 A1 | 12/2008 | Greenhalgh et al. |
| 2009/0012566 A1 | 1/2009 | Fauth |
| 2009/0012623 A1 | 1/2009 | Sack et al. |
| 2009/0024166 A1 | 1/2009 | Carl et al. |
| 2009/0024217 A1 | 1/2009 | Levy et al. |
| 2009/0030423 A1 | 1/2009 | Puno |
| 2009/0030457 A1 | 1/2009 | Janowski et al. |
| 2009/0030465 A1 | 1/2009 | Altarac et al. |
| 2009/0030519 A1 | 1/2009 | Falahee |
| 2009/0030520 A1 | 1/2009 | Biedermann et al. |
| 2009/0036746 A1 | 2/2009 | Blackwell et al. |
| 2009/0036927 A1 | 2/2009 | Vestgaarden |
| 2009/0036929 A1 | 2/2009 | Reglos et al. |
| 2009/0036988 A1* | 2/2009 | Peckham ............... A61B 17/56 623/17.16 |
| 2009/0048668 A1 | 2/2009 | Wilson et al. |
| 2009/0054931 A1 | 2/2009 | Metz-Stavenhagen |
| 2009/0062869 A1 | 3/2009 | Claverie et al. |
| 2009/0062915 A1 | 3/2009 | Kohm et al. |
| 2009/0062918 A1 | 3/2009 | Wang et al. |
| 2009/0062920 A1 | 3/2009 | Tauber |
| 2009/0076333 A1 | 3/2009 | Bjork |
| 2009/0076516 A1 | 3/2009 | Lowry et al. |
| 2009/0076615 A1 | 3/2009 | Duggal et al. |
| 2009/0082808 A1 | 3/2009 | Butler et al. |
| 2009/0082813 A1 | 3/2009 | Long et al. |
| 2009/0093884 A1 | 4/2009 | Bass |
| 2009/0099601 A1 | 4/2009 | Aferzon et al. |
| 2009/0105547 A1 | 4/2009 | Vayser et al. |
| 2009/0105761 A1 | 4/2009 | Robie |
| 2009/0105768 A1 | 4/2009 | Cragg et al. |
| 2009/0105773 A1 | 4/2009 | Lange et al. |
| 2009/0105830 A1 | 4/2009 | Jones et al. |
| 2009/0105831 A1 | 4/2009 | Jones et al. |
| 2009/0118766 A1 | 5/2009 | Park et al. |
| 2009/0118771 A1 | 5/2009 | Gonzalez-Hernandez |
| 2009/0124861 A1 | 5/2009 | Fetzer |
| 2009/0125062 A1 | 5/2009 | Arnin |
| 2009/0125071 A1 | 5/2009 | Skinlo et al. |
| 2009/0132054 A1 | 5/2009 | Zeegers |
| 2009/0143859 A1 | 6/2009 | McClellan, III et al. |
| 2009/0149956 A1 | 6/2009 | Greenhalgh et al. |
| 2009/0149959 A1 | 6/2009 | Conner et al. |
| 2009/0157186 A1 | 6/2009 | Magerl |
| 2009/0157188 A1 | 6/2009 | Zeegers |
| 2009/0163920 A1 | 6/2009 | Hochschuler et al. |
| 2009/0163957 A1 | 6/2009 | St. Clair et al. |
| 2009/0163961 A1 | 6/2009 | Kirschman |
| 2009/0164020 A1 | 6/2009 | Janowski et al. |
| 2009/0171394 A1 | 7/2009 | Abdou |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0187249 A1 | 7/2009 | Osman |
| 2009/0192613 A1 | 7/2009 | Wing et al. |
| 2009/0192615 A1 | 7/2009 | Tyber et al. |
| 2009/0198211 A1 | 8/2009 | Thorne, Jr. et al. |
| 2009/0198277 A1 | 8/2009 | Gordon et al. |
| 2009/0204151 A1 | 8/2009 | Bracken |
| 2009/0204154 A1 | 8/2009 | Kiester |
| 2009/0204218 A1 | 8/2009 | Richelsoph |
| 2009/0204219 A1 | 8/2009 | Beaurain et al. |
| 2009/0210007 A1 | 8/2009 | Levy et al. |
| 2009/0210015 A1 | 8/2009 | Cermak et al. |
| 2009/0210062 A1 | 8/2009 | Thalgott et al. |
| 2009/0216234 A1* | 8/2009 | Farr ............... A61B 17/025 606/79 |
| 2009/0216241 A1 | 8/2009 | Dinville |
| 2009/0222046 A1 | 9/2009 | Gorek |

(56) References Cited

U.S. PATENT DOCUMENTS

| | | |
|---|---|---|
| 2009/0222092 A1 | 9/2009 | Davis et al. |
| 2009/0222100 A1 | 9/2009 | Cipoletti et al. |
| 2009/0227845 A1 | 9/2009 | Lo et al. |
| 2009/0228045 A1 | 9/2009 | Hayes et al. |
| 2009/0228108 A1 | 9/2009 | Keller |
| 2009/0228110 A1 | 9/2009 | McClintock |
| 2009/0234364 A1 | 9/2009 | Crook |
| 2009/0234455 A1 | 9/2009 | Moskowitz et al. |
| 2009/0240334 A1 | 9/2009 | Richelsoph |
| 2009/0240335 A1 | 9/2009 | Arcenio et al. |
| 2009/0247819 A1 | 10/2009 | Wilson et al. |
| 2009/0248078 A1 | 10/2009 | Dant |
| 2009/0248089 A1 | 10/2009 | Jacofsky et al. |
| 2009/0254125 A1 | 10/2009 | Predick |
| 2009/0259257 A1 | 10/2009 | Prevost |
| 2009/0265007 A1 | 10/2009 | Colleran |
| 2009/0270918 A1 | 10/2009 | Attia et al. |
| 2009/0270989 A1 | 10/2009 | Conner et al. |
| 2009/0270990 A1 | 10/2009 | Louis et al. |
| 2009/0281628 A1 | 11/2009 | Oglaza et al. |
| 2009/0290316 A1 | 11/2009 | Kariya |
| 2009/0292361 A1 | 11/2009 | Lopez |
| 2009/0299478 A1 | 12/2009 | Carls et al. |
| 2009/0326538 A1 | 12/2009 | Sennett et al. |
| 2009/0326581 A1 | 12/2009 | Galley et al. |
| 2009/0326584 A1 | 12/2009 | Slivka et al. |
| 2010/0004664 A1 | 1/2010 | Boyajian et al. |
| 2010/0009929 A1 | 1/2010 | Cheng et al. |
| 2010/0016897 A1 | 1/2010 | Le et al. |
| 2010/0016906 A1 | 1/2010 | Abdou |
| 2010/0023061 A1 | 1/2010 | Randol et al. |
| 2010/0023064 A1 | 1/2010 | Brunger et al. |
| 2010/0036423 A1 | 2/2010 | Hayes et al. |
| 2010/0036495 A1 | 2/2010 | Daum et al. |
| 2010/0042149 A1 | 2/2010 | Chao et al. |
| 2010/0049324 A1 | 2/2010 | Valdevit et al. |
| 2010/0069929 A1 | 3/2010 | Abdou |
| 2010/0069962 A1 | 3/2010 | Harms et al. |
| 2010/0069965 A1 | 3/2010 | Abdou |
| 2010/0070041 A1 | 3/2010 | Peterman et al. |
| 2010/0076448 A1 | 3/2010 | Abdou |
| 2010/0082109 A1 | 4/2010 | Greenhalgh et al. |
| 2010/0087858 A1 | 4/2010 | Abdou |
| 2010/0087869 A1 | 4/2010 | Abdou |
| 2010/0087878 A1 | 4/2010 | Abdou |
| 2010/0087923 A1 | 4/2010 | Abdou |
| 2010/0094422 A1 | 4/2010 | Hansell et al. |
| 2010/0100137 A1 | 4/2010 | Justis et al. |
| 2010/0106250 A1 | 4/2010 | Abdou |
| 2010/0121384 A1 | 5/2010 | Abdou |
| 2010/0130827 A1 | 5/2010 | Pimenta et al. |
| 2010/0152778 A1 | 6/2010 | Saint et al. |
| 2010/0174315 A1 | 7/2010 | Scodary et al. |
| 2010/0179657 A1 | 7/2010 | Greenhalgh et al. |
| 2010/0185291 A1 | 7/2010 | Jimenez et al. |
| 2010/0191336 A1 | 7/2010 | Greenhalgh |
| 2010/0191337 A1 | 7/2010 | Zamani et al. |
| 2010/0204795 A1 | 8/2010 | Greenhalgh |
| 2010/0211101 A1 | 8/2010 | Blackwell et al. |
| 2010/0211176 A1 | 8/2010 | Greenhalgh |
| 2010/0211177 A1 | 8/2010 | Abdou |
| 2010/0217382 A1 | 8/2010 | Chau et al. |
| 2010/0222644 A1 | 9/2010 | Sebastian et al. |
| 2010/0222816 A1 | 9/2010 | Gabelberger et al. |
| 2010/0222884 A1 | 9/2010 | Greenhalgh et al. |
| 2010/0234889 A1 | 9/2010 | Hess |
| 2010/0234952 A1 | 9/2010 | Peterman |
| 2010/0241168 A1 | 9/2010 | Franck et al. |
| 2010/0249933 A1 | 9/2010 | Trieu |
| 2010/0256759 A1 | 10/2010 | Hansell et al. |
| 2010/0256760 A1 | 10/2010 | Hansell |
| 2010/0262245 A1 | 10/2010 | Alfaro et al. |
| 2010/0262248 A1 | 10/2010 | Sournac et al. |
| 2010/0268281 A1 | 10/2010 | Abdou |
| 2010/0280622 A1 | 11/2010 | McKinley |
| 2010/0286483 A1 | 11/2010 | Bettuchi et al. |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0305705 A1 | 12/2010 | Butler et al. |
| 2010/0312282 A1 | 12/2010 | Abdou |
| 2010/0312347 A1 | 12/2010 | Arramon et al. |
| 2010/0318128 A1 | 12/2010 | Abdou |
| 2010/0331883 A1* | 12/2010 | Schmitz ............ A61B 10/0275 606/249 |
| 2010/0331887 A1 | 12/2010 | Jackson et al. |
| 2010/0331889 A1 | 12/2010 | Abdou |
| 2010/0331981 A1 | 12/2010 | Mohammed |
| 2010/0331985 A1 | 12/2010 | Gordon et al. |
| 2011/0004248 A1 | 1/2011 | Abdou |
| 2011/0009969 A1 | 1/2011 | Puno |
| 2011/0009970 A1 | 1/2011 | Puno |
| 2011/0022090 A1 | 1/2011 | Gordon et al. |
| 2011/0029083 A1 | 2/2011 | Hynes et al. |
| 2011/0029085 A1 | 2/2011 | Hynes et al. |
| 2011/0035011 A1 | 2/2011 | Cain |
| 2011/0046679 A1 | 2/2011 | Chow et al. |
| 2011/0046740 A1 | 2/2011 | Chen et al. |
| 2011/0054531 A1 | 3/2011 | Lamborne et al. |
| 2011/0060366 A1 | 3/2011 | Heim et al. |
| 2011/0066186 A1 | 3/2011 | Boyer, II et al. |
| 2011/0082551 A1 | 4/2011 | Kraus |
| 2011/0082553 A1 | 4/2011 | Abdou |
| 2011/0093074 A1 | 4/2011 | Glerum et al. |
| 2011/0098749 A1 | 4/2011 | Boomer et al. |
| 2011/0106163 A1 | 5/2011 | Hochschuler et al. |
| 2011/0106259 A1 | 5/2011 | Lindenmann et al. |
| 2011/0118552 A1 | 5/2011 | Fischvogt |
| 2011/0125266 A1 | 5/2011 | Rodgers et al. |
| 2011/0130793 A1 | 6/2011 | Woolley et al. |
| 2011/0137353 A1 | 6/2011 | Buttermann |
| 2011/0144692 A1 | 6/2011 | Saladin et al. |
| 2011/0166600 A1 | 7/2011 | Lamborne et al. |
| 2011/0172720 A1 | 7/2011 | Metcalf, Jr. et al. |
| 2011/0172772 A1 | 7/2011 | Abdou |
| 2011/0184471 A1* | 7/2011 | Foley ................ A61B 17/7032 606/286 |
| 2011/0190825 A1 | 8/2011 | Thalgott et al. |
| 2011/0196492 A1 | 8/2011 | Lambrecht et al. |
| 2011/0213465 A1 | 9/2011 | Landry et al. |
| 2011/0224497 A1 | 9/2011 | Weiman et al. |
| 2011/0238181 A1 | 9/2011 | Trieu |
| 2011/0251693 A1 | 10/2011 | Barreiro et al. |
| 2011/0264218 A1 | 10/2011 | Asaad |
| 2011/0264228 A1 | 10/2011 | Johnson et al. |
| 2011/0276099 A1 | 11/2011 | Champagne et al. |
| 2011/0276142 A1 | 11/2011 | Niemiec et al. |
| 2011/0282459 A1 | 11/2011 | McClellan, III et al. |
| 2011/0288588 A1 | 11/2011 | Chin et al. |
| 2011/0288594 A1 | 11/2011 | Woolley et al. |
| 2011/0288644 A1 | 11/2011 | Gray et al. |
| 2011/0288645 A1 | 11/2011 | Braddock, Jr. et al. |
| 2011/0301710 A1 | 12/2011 | Mather et al. |
| 2011/0301712 A1 | 12/2011 | Palmatier et al. |
| 2011/0307011 A1 | 12/2011 | Moskowitz et al. |
| 2011/0307012 A1 | 12/2011 | Mir et al. |
| 2011/0319995 A1 | 12/2011 | Voellmicke et al. |
| 2012/0010472 A1 | 1/2012 | Spann |
| 2012/0010658 A1 | 1/2012 | Kirschman |
| 2012/0016481 A1 | 1/2012 | Zwirkoski |
| 2012/0029565 A1 | 2/2012 | Seifert et al. |
| 2012/0029639 A1 | 2/2012 | Blackwell et al. |
| 2012/0035424 A1 | 2/2012 | Schulte |
| 2012/0041272 A1 | 2/2012 | Dietze, Jr. et al. |
| 2012/0071980 A1 | 3/2012 | Purcell et al. |
| 2012/0078301 A1 | 3/2012 | Hess |
| 2012/0089184 A1 | 4/2012 | Yeh |
| 2012/0095512 A1 | 4/2012 | Nihalani |
| 2012/0101528 A1 | 4/2012 | Souza et al. |
| 2012/0136442 A1 | 5/2012 | Kleiner |
| 2012/0150229 A1 | 6/2012 | Hess |
| 2012/0150302 A1 | 6/2012 | Gray |
| 2012/0158060 A1* | 6/2012 | Abrahams .......... A61B 17/7052 606/248 |

(56) References Cited

U.S. PATENT DOCUMENTS

| | | |
|---|---|---|
| 2012/0158140 A1 | 6/2012 | Miller et al. |
| 2012/0158150 A1 | 6/2012 | Siegal |
| 2012/0179260 A1 | 7/2012 | Nottingham |
| 2012/0185045 A1 | 7/2012 | Morris et al. |
| 2012/0190933 A1 | 7/2012 | Kleyman |
| 2012/0191135 A1* | 7/2012 | Abdou ............... A61B 17/7065 606/248 |
| 2012/0197297 A1 | 8/2012 | Bootwala et al. |
| 2012/0197401 A1 | 8/2012 | Duncan et al. |
| 2012/0197402 A1 | 8/2012 | Blackwell et al. |
| 2012/0203279 A1 | 8/2012 | Walters et al. |
| 2012/0209271 A1 | 8/2012 | Cohen et al. |
| 2012/0209383 A1 | 8/2012 | Tsuang et al. |
| 2012/0215316 A1 | 8/2012 | Mohr et al. |
| 2012/0221049 A1 | 8/2012 | Blain et al. |
| 2012/0226313 A1 | 9/2012 | Dace |
| 2012/0232592 A1 | 9/2012 | Massoudi |
| 2012/0232658 A1 | 9/2012 | Morgenstern et al. |
| 2012/0238825 A1 | 9/2012 | Smith |
| 2012/0245425 A1 | 9/2012 | Okoniewski |
| 2012/0245431 A1 | 9/2012 | Baudouin et al. |
| 2012/0245432 A1 | 9/2012 | Karpowicz et al. |
| 2012/0245704 A1 | 9/2012 | Childs et al. |
| 2012/0253393 A1 | 10/2012 | Fiorella |
| 2012/0253396 A1 | 10/2012 | Stern et al. |
| 2012/0259416 A1 | 10/2012 | Blackwell et al. |
| 2012/0265021 A1 | 10/2012 | Nottmeier |
| 2012/0271119 A1 | 10/2012 | White |
| 2012/0277864 A1 | 11/2012 | Brodke et al. |
| 2012/0283521 A1 | 11/2012 | Smith et al. |
| 2012/0290017 A1 | 11/2012 | Haidukewych |
| 2012/0290096 A1 | 11/2012 | Messerli |
| 2012/0296171 A1 | 11/2012 | Lovell et al. |
| 2012/0296377 A1 | 11/2012 | Ferree et al. |
| 2013/0018467 A1 | 1/2013 | Suh |
| 2013/0023933 A1 | 1/2013 | Haas |
| 2013/0023937 A1 | 1/2013 | Biedermann et al. |
| 2013/0030467 A1 | 1/2013 | Karas et al. |
| 2013/0030469 A1 | 1/2013 | Karas et al. |
| 2013/0030470 A1 | 1/2013 | Karas et al. |
| 2013/0041471 A1 | 2/2013 | Siegal et al. |
| 2013/0053896 A1* | 2/2013 | Voyadzis ............. A61B 17/708 606/279 |
| 2013/0060284 A1 | 3/2013 | Abdou |
| 2013/0066374 A1 | 3/2013 | Galley et al. |
| 2013/0079883 A1 | 3/2013 | Butler et al. |
| 2013/0090691 A1 | 4/2013 | Zhang et al. |
| 2013/0103088 A1 | 4/2013 | Karahalios et al. |
| 2013/0103089 A1 | 4/2013 | Gordon et al. |
| 2013/0123849 A1 | 5/2013 | Abdou |
| 2013/0131738 A1 | 5/2013 | Powell et al. |
| 2013/0144339 A1 | 6/2013 | Choi et al. |
| 2013/0144340 A1 | 6/2013 | Sheffer et al. |
| 2013/0150886 A1 | 6/2013 | Altarac et al. |
| 2013/0150970 A1 | 6/2013 | Thaiyananthan |
| 2013/0158359 A1 | 6/2013 | Predick et al. |
| 2013/0165982 A1 | 6/2013 | Ek et al. |
| 2013/0172932 A1 | 7/2013 | Altarac et al. |
| 2013/0172933 A1 | 7/2013 | Altarac et al. |
| 2013/0172934 A1 | 7/2013 | Walker et al. |
| 2013/0184752 A1 | 7/2013 | Binder |
| 2013/0184758 A1* | 7/2013 | Karim ............... A61B 17/683 606/258 |
| 2013/0190573 A1 | 7/2013 | Smith |
| 2013/0190575 A1 | 7/2013 | Mast et al. |
| 2013/0204091 A1 | 8/2013 | Menendez et al. |
| 2013/0218166 A1* | 8/2013 | Elmore ............... A61B 90/06 606/104 |
| 2013/0226240 A1* | 8/2013 | Abdou ............... A61B 17/7067 606/248 |
| 2013/0245383 A1 | 9/2013 | Friedrich et al. |
| 2013/0253585 A1 | 9/2013 | Garcia et al. |
| 2013/0253586 A1 | 9/2013 | Rathbun et al. |
| 2013/0261401 A1 | 10/2013 | Hawkins et al. |
| 2013/0261666 A1 | 10/2013 | Gundanna |
| 2013/0274883 A1 | 10/2013 | McLuen et al. |
| 2013/0274884 A1 | 10/2013 | Matsumoto et al. |
| 2013/0296939 A1 | 11/2013 | Perkins |
| 2013/0296940 A1 | 11/2013 | Northcutt et al. |
| 2013/0310942 A1 | 11/2013 | Abdou |
| 2013/0325128 A1 | 12/2013 | Perloff et al. |
| 2014/0005484 A1 | 1/2014 | Charles |
| 2014/0031874 A1 | 1/2014 | Kucharzyk et al. |
| 2014/0058512 A1 | 2/2014 | Petersheim |
| 2014/0081331 A1 | 3/2014 | Zappacosta et al. |
| 2014/0107783 A1* | 4/2014 | Abdou ............... A61B 17/7064 623/17.11 |
| 2014/0114137 A1 | 4/2014 | Reglos et al. |
| 2014/0114138 A1 | 4/2014 | Fedorov et al. |
| 2014/0114139 A1 | 4/2014 | Ziolo et al. |
| 2014/0135584 A1 | 5/2014 | Lee et al. |
| 2014/0148652 A1 | 5/2014 | Weiman |
| 2014/0148856 A1 | 5/2014 | Ibarra et al. |
| 2014/0155939 A1 | 6/2014 | Sugawara |
| 2014/0172002 A1 | 6/2014 | Predick |
| 2014/0172105 A1 | 6/2014 | Frasier |
| 2014/0172107 A1 | 6/2014 | Thirugnanasambandam et al. |
| 2014/0188223 A1 | 7/2014 | Jensen et al. |
| 2014/0188233 A1 | 7/2014 | Mutchler et al. |
| 2014/0249631 A1 | 9/2014 | Weiman |
| 2014/0277143 A1 | 9/2014 | Zappacosta |
| 2014/0277490 A1 | 9/2014 | Perloff et al. |
| 2014/0277499 A1 | 9/2014 | Ainsworth et al. |
| 2014/0277502 A1 | 9/2014 | Schiffman et al. |
| 2014/0288480 A1 | 9/2014 | Zimmerman et al. |
| 2014/0309741 A1 | 10/2014 | Ganter et al. |
| 2014/0336471 A1 | 11/2014 | Pfabe et al. |
| 2014/0343608 A1 | 11/2014 | Whiton et al. |
| 2014/0350347 A1 | 11/2014 | Karpowicz et al. |
| 2014/0379032 A1* | 12/2014 | Hennard ............. A61B 17/56 606/279 |
| 2014/0379086 A1 | 12/2014 | Elahinia et al. |
| 2015/0018829 A1 | 1/2015 | Woodburn, Sr. et al. |
| 2015/0057755 A1 | 2/2015 | Suddaby et al. |
| 2015/0094814 A1 | 4/2015 | Emerick et al. |
| 2015/0202053 A1 | 7/2015 | Willis et al. |
| 2015/0305785 A1* | 10/2015 | Taber ............... A61B 17/7065 606/249 |
| 2015/0313585 A1 | 11/2015 | Abidin et al. |
| 2015/0313650 A1 | 11/2015 | Taber et al. |
| 2015/0351738 A1 | 12/2015 | Perrow |
| 2015/0359640 A1 | 12/2015 | Taber et al. |
| 2016/0000419 A1 | 1/2016 | Weisshaupt et al. |
| 2016/0030030 A1 | 2/2016 | Bass |
| 2016/0045333 A1 | 2/2016 | Baynham |
| 2016/0081681 A1 | 3/2016 | Waugh et al. |
| 2016/0089247 A1 | 3/2016 | Nichols et al. |
| 2016/0213443 A1 | 7/2016 | Lueck et al. |
| 2016/0270772 A1* | 9/2016 | Beale ................. A61B 17/56 |
| 2016/0287236 A1* | 10/2016 | Garcia-Bengochea ................. A61B 17/0206 |
| 2016/0310294 A1 | 10/2016 | McConnell et al. |
| 2016/0317323 A1 | 11/2016 | Cho et al. |
| 2016/0317324 A1 | 11/2016 | Cho et al. |
| 2016/0354210 A1* | 12/2016 | Tran .................. A61F 2/442 |
| 2016/0361177 A1 | 12/2016 | Biedermann et al. |
| 2017/0007226 A1 | 1/2017 | Fehling |
| 2017/0014117 A1 | 1/2017 | Capote |
| 2017/0042527 A1 | 2/2017 | Farley et al. |
| 2017/0056194 A1 | 3/2017 | Biedermann et al. |
| 2017/0065269 A1 | 3/2017 | Thommen et al. |
| 2017/0112635 A1 | 4/2017 | Ty et al. |
| 2017/0143325 A1 | 5/2017 | Lynn et al. |
| 2017/0172759 A1 | 6/2017 | Kukkar et al. |
| 2017/0172760 A1 | 6/2017 | Loebl et al. |
| 2017/0231613 A1 | 8/2017 | Casey et al. |
| 2017/0340451 A1 | 11/2017 | McCormack et al. |
| 2018/0021149 A1 | 1/2018 | Boehm et al. |
| 2018/0085105 A1 | 3/2018 | Kim |
| 2018/0206834 A1 | 7/2018 | Villamil et al. |
| 2018/0235724 A1 | 8/2018 | Nowatschin et al. |
| 2018/0249992 A1 | 9/2018 | Truckey |
| 2018/0256363 A1 | 9/2018 | Moon |

(56) References Cited

U.S. PATENT DOCUMENTS

| | | |
|---|---|---|
| 2018/0289506 A1 | 10/2018 | Kim et al. |
| 2018/0303624 A1 | 10/2018 | Shoshtaev |
| 2018/0310927 A1 | 11/2018 | Garcia-Bengochea et al. |
| 2018/0333061 A1 | 11/2018 | Pracyk et al. |
| 2018/0344481 A1 | 12/2018 | Garcia-Bengochea |
| 2018/0360621 A1 | 12/2018 | Moon |
| 2019/0192312 A1 | 6/2019 | Ullrich, Jr. et al. |
| 2019/0209154 A1 | 7/2019 | Richter et al. |
| 2019/0216450 A1 | 7/2019 | Bjork et al. |
| 2019/0216453 A1 | 7/2019 | Predick et al. |
| 2019/0307439 A1 | 10/2019 | Chhit et al. |
| 2019/0321022 A1 | 10/2019 | Karpowicz et al. |
| 2020/0085530 A1 | 3/2020 | Sauer |
| 2020/0113713 A1 | 4/2020 | LaMarca et al. |

FOREIGN PATENT DOCUMENTS

| | | |
|---|---|---|
| DE | 29911422 U1 | 8/1999 |
| DE | 10035182 A1 | 2/2002 |
| DE | 20320454 U1 | 10/2004 |
| DE | 10323363 A1 | 12/2004 |
| EP | 0077159 A1 | 4/1983 |
| EP | 0274713 A1 | 7/1988 |
| EP | 0301489 A1 | 2/1989 |
| EP | 0317972 A1 | 5/1989 |
| EP | 0333990 A2 | 9/1989 |
| EP | 0356112 A1 | 2/1990 |
| EP | 0418387 A1 | 3/1991 |
| EP | 0512529 A1 | 11/1992 |
| EP | 0560141 A1 | 9/1993 |
| EP | 0566810 A1 | 10/1993 |
| EP | 0611116 A1 | 8/1994 |
| EP | 0614649 A1 | 9/1994 |
| EP | 0637439 A1 | 2/1995 |
| EP | 0697200 A1 | 2/1996 |
| EP | 0611116 B1 | 7/1996 |
| EP | 0566810 B1 | 8/1996 |
| EP | 0747025 A1 | 12/1996 |
| EP | 0951879 A2 | 10/1999 |
| EP | 0955021 A1 | 11/1999 |
| EP | 0965313 A1 | 12/1999 |
| EP | 1180348 A2 | 2/2002 |
| EP | 1192910 A2 | 4/2002 |
| EP | 1222903 A1 | 7/2002 |
| EP | 1254640 A2 | 11/2002 |
| EP | 1287795 A1 | 3/2003 |
| EP | 1442715 A2 | 8/2004 |
| EP | 1504733 A1 | 2/2005 |
| EP | 1374808 B1 | 12/2005 |
| EP | 1758511 A2 | 3/2007 |
| EP | 1848352 A2 | 10/2007 |
| EP | 1872731 A1 | 1/2008 |
| EP | 1942816 A2 | 7/2008 |
| EP | 1942838 A2 | 7/2008 |
| EP | 1980222 A1 | 10/2008 |
| EP | 1389978 B1 | 1/2009 |
| EP | 2032086 A2 | 3/2009 |
| EP | 2101691 A2 | 9/2009 |
| EP | 2113228 A1 | 11/2009 |
| EP | 2327375 A1 | 6/2011 |
| EP | 2340788 A1 | 7/2011 |
| EP | 2363080 A1 | 9/2011 |
| EP | 2131790 B1 | 10/2012 |
| EP | 3111896 A1 | 1/2017 |
| FR | 1037262 A | 9/1953 |
| FR | 2124815 A5 | 9/1972 |
| FR | 2632516 A1 | 12/1989 |
| FR | 2659226 A1 | 9/1991 |
| FR | 2703239 A1 | 10/1994 |
| FR | 2703580 A1 | 10/1994 |
| FR | 2723841 A1 | 3/1996 |
| FR | 2724108 A1 | 3/1996 |
| FR | 2730159 A1 | 8/1996 |
| FR | 2733413 A1 | 10/1996 |
| FR | 2747034 A1 | 10/1997 |
| FR | 2781359 A1 | 1/2000 |
| FR | 2787021 A1 | 6/2000 |
| FR | 2788958 A1 | 8/2000 |
| FR | 2806614 A1 | 9/2001 |
| FR | 2808995 A1 | 11/2001 |
| FR | 2813782 A1 | 3/2002 |
| FR | 2824261 A1 | 11/2002 |
| FR | 2827156 A1 | 1/2003 |
| FR | 2831796 A1 | 5/2003 |
| FR | 2846550 A1 | 5/2004 |
| FR | 2856271 A1 | 12/2004 |
| FR | 2861582 A1 | 5/2005 |
| FR | 2865629 A1 | 8/2005 |
| FR | 2879436 A1 | 6/2006 |
| FR | 2880795 A1 | 7/2006 |
| FR | 2887762 A1 | 1/2007 |
| FR | 2891135 A1 | 3/2007 |
| FR | 2893838 A1 | 6/2007 |
| FR | 2897259 A1 | 8/2007 |
| FR | 2902639 A1 | 12/2007 |
| FR | 2916956 A1 | 12/2008 |
| FR | 2930718 A1 | 11/2009 |
| GB | 780652 A | 8/1957 |
| GB | 2178323 A | 2/1987 |
| JP | H02261446 A | 10/1990 |
| JP | H0998983 A | 4/1997 |
| WO | WO-9000037 A1 | 1/1990 |
| WO | WO-9107931 A1 | 6/1991 |
| WO | WO-9301771 A1 | 2/1993 |
| WO | WO-9307823 A1 | 4/1993 |
| WO | WO-9314721 A1 | 8/1993 |
| WO | WO-9404100 A1 | 3/1994 |
| WO | WO-9420048 A1 | 9/1994 |
| WO | WO-9508306 A1 | 3/1995 |
| WO | WO-9510240 A1 | 4/1995 |
| WO | WO-9515133 A1 | 6/1995 |
| WO | WO-9525474 A1 | 9/1995 |
| WO | WO-9715248 A1 | 5/1997 |
| WO | WO-9723174 A1 | 7/1997 |
| WO | WO-9730666 A2 | 8/1997 |
| WO | WO-9737620 A1 | 10/1997 |
| WO | WO-9801091 A1 | 1/1998 |
| WO | WO-9817209 A2 | 4/1998 |
| WO | WO-9855052 A1 | 12/1998 |
| WO | WO-9900065 A1 | 1/1999 |
| WO | WO-9904718 A1 | 2/1999 |
| WO | WO-9909914 A1 | 3/1999 |
| WO | WO-9921500 A1 | 5/1999 |
| WO | WO-9921502 A1 | 5/1999 |
| WO | WO-9933405 A1 | 7/1999 |
| WO | WO-9938463 A2 | 8/1999 |
| WO | WO-9953871 A1 | 10/1999 |
| WO | WO-9956653 A1 | 11/1999 |
| WO | WO-9956675 A1 | 11/1999 |
| WO | WO-9956676 A1 | 11/1999 |
| WO | WO-9963914 A1 | 12/1999 |
| WO | WO-9965412 A1 | 12/1999 |
| WO | WO-9966864 A1 | 12/1999 |
| WO | WO-0015125 A1 | 3/2000 |
| WO | WO-0018312 A1 | 4/2000 |
| WO | WO-0023015 A1 | 4/2000 |
| WO | WO-0024325 A1 | 5/2000 |
| WO | WO-0024327 A2 | 5/2000 |
| WO | WO-0053127 A1 | 9/2000 |
| WO | WO-0064362 A1 | 11/2000 |
| WO | WO-0072770 A1 | 12/2000 |
| WO | WO-0074606 A1 | 12/2000 |
| WO | WO-0078238 A1 | 12/2000 |
| WO | WO-0101874 A1 | 1/2001 |
| WO | WO-0103592 A1 | 1/2001 |
| WO | WO-0106940 A1 | 2/2001 |
| WO | WO-0119295 A1 | 3/2001 |
| WO | WO-0126566 A1 | 4/2001 |
| WO | WO-0128465 A2 | 4/2001 |
| WO | WO-0141680 A1 | 6/2001 |
| WO | WO-0143620 A2 | 6/2001 |
| WO | WO-0145577 A2 | 6/2001 |
| WO | WO-0160270 A1 | 8/2001 |
| WO | WO-0162191 A2 | 8/2001 |

(56) References Cited

FOREIGN PATENT DOCUMENTS

| | | |
|---|---|---|
| WO | WO-0170141 A1 | 9/2001 |
| WO | WO-0187194 A1 | 11/2001 |
| WO | WO-0211633 A2 | 2/2002 |
| WO | WO-0213732 A2 | 2/2002 |
| WO | WO-0228299 A1 | 4/2002 |
| WO | WO-0230307 A2 | 4/2002 |
| WO | WO-02051326 A1 | 7/2002 |
| WO | WO-02058599 A2 | 8/2002 |
| WO | WO-02058600 A2 | 8/2002 |
| WO | WO-02071960 A1 | 9/2002 |
| WO | WO-02076315 A1 | 10/2002 |
| WO | WO-02080788 A1 | 10/2002 |
| WO | WO-02089701 A2 | 11/2002 |
| WO | WO-03005939 A2 | 1/2003 |
| WO | WO-03007829 A1 | 1/2003 |
| WO | WO-03015646 A2 | 2/2003 |
| WO | WO-03024298 A2 | 3/2003 |
| WO | WO-03026522 A2 | 4/2003 |
| WO | WO-03032850 A1 | 4/2003 |
| WO | WO-03032851 A1 | 4/2003 |
| WO | WO-03037200 A2 | 5/2003 |
| WO | WO-03039400 A2 | 5/2003 |
| WO | WO-03045262 A2 | 6/2003 |
| WO | WO-03049629 A1 | 6/2003 |
| WO | WO-03051212 A2 | 6/2003 |
| WO | WO-03059212 A1 | 7/2003 |
| WO | WO-03075803 A1 | 9/2003 |
| WO | WO-03075804 A1 | 9/2003 |
| WO | WO-2004016217 A2 | 2/2004 |
| WO | WO-2004032726 A2 | 4/2004 |
| WO | WO-2004034935 A1 | 4/2004 |
| WO | WO-2004039283 A2 | 5/2004 |
| WO | WO-2004039291 A1 | 5/2004 |
| WO | WO-2004041129 A1 | 5/2004 |
| WO | WO-2004049915 A2 | 6/2004 |
| WO | WO-2004062482 A2 | 7/2004 |
| WO | WO-2004084774 A1 | 10/2004 |
| WO | WO-2004093702 A2 | 11/2004 |
| WO | WO-2004105577 A2 | 12/2004 |
| WO | WO-2005007040 A1 | 1/2005 |
| WO | WO-2005009262 A1 | 2/2005 |
| WO | WO-2005011522 A2 | 2/2005 |
| WO | WO-2005020829 A1 | 3/2005 |
| WO | WO-2005044119 A2 | 5/2005 |
| WO | WO-2005046534 A1 | 5/2005 |
| WO | WO-2005051243 A2 | 6/2005 |
| WO | WO-2005074839 A1 | 8/2005 |
| WO | WO-2005077288 A1 | 8/2005 |
| WO | WO-2005104996 A1 | 11/2005 |
| WO | WO-2005117728 A1 | 12/2005 |
| WO | WO-2005122922 A2 | 12/2005 |
| WO | WO-2006016384 A1 | 2/2006 |
| WO | WO-2006041963 A2 | 4/2006 |
| WO | WO-2006042335 A1 | 4/2006 |
| WO | WO-2006045089 A2 | 4/2006 |
| WO | WO-2006047587 A2 | 5/2006 |
| WO | WO-2006058221 A2 | 6/2006 |
| WO | WO-2006062960 A2 | 6/2006 |
| WO | WO-2006086241 A2 | 8/2006 |
| WO | WO-2006089292 A2 | 8/2006 |
| WO | WO-2006096756 A2 | 9/2006 |
| WO | WO-2006106268 A2 | 10/2006 |
| WO | WO-2006110578 A2 | 10/2006 |
| WO | WO-2006120505 A1 | 11/2006 |
| WO | WO-2006130460 A2 | 12/2006 |
| WO | WO-2006136760 A2 | 12/2006 |
| WO | WO-2007000634 A1 | 1/2007 |
| WO | WO-2007000654 A2 | 1/2007 |
| WO | WO-2007034310 A1 | 3/2007 |
| WO | WO-2007038475 A2 | 4/2007 |
| WO | WO-2007041648 A2 | 4/2007 |
| WO | WO-2007044705 A2 | 4/2007 |
| WO | WO-2007044836 A2 | 4/2007 |
| WO | WO-2007056516 A2 | 5/2007 |
| WO | WO-2007059207 A2 | 5/2007 |
| WO | WO-2007063398 A2 | 6/2007 |
| WO | WO-2007078978 A2 | 7/2007 |
| WO | WO-2007087535 A2 | 8/2007 |
| WO | WO-2007089975 A1 | 8/2007 |
| WO | WO-2007093900 A2 | 8/2007 |
| WO | WO-2007095333 A2 | 8/2007 |
| WO | WO-2007106573 A2 | 9/2007 |
| WO | WO-2007075843 A3 | 12/2007 |
| WO | WO-2007140382 A2 | 12/2007 |
| WO | WO-2008013960 A2 | 1/2008 |
| WO | WO-2008021319 A2 | 2/2008 |
| WO | WO-2008024373 A2 | 2/2008 |
| WO | WO-2008067452 A1 | 6/2008 |
| WO | WO-2008073447 A2 | 6/2008 |
| WO | WO-2008082836 A1 | 7/2008 |
| WO | WO-2008085521 A1 | 7/2008 |
| WO | WO-2008099277 A2 | 8/2008 |
| WO | WO-2008106140 A2 | 9/2008 |
| WO | WO-2008131084 A2 | 10/2008 |
| WO | WO-2008149223 A2 | 12/2008 |
| WO | WO-2009033100 A1 | 3/2009 |
| WO | WO-2009064787 A2 | 5/2009 |
| WO | WO-2009135208 A1 | 11/2009 |
| WO | WO-2009152126 A1 | 12/2009 |
| WO | WO-2010057980 A1 | 5/2010 |
| WO | WO-2013006830 A1 | 1/2013 |

OTHER PUBLICATIONS

Denis, F., "The Three Column Spine and its Significance in the Classification of Acute Thoracolumbar Spinal Injuries," Spine (Phila Pa 1976), 1983, vol. 8 (8), pp. 817-831.
Hoshide R., et al., "Cadaveric Analysis of the Kambin's Triangle" Cureus, Feb. 2, 2016, vol. 8 (2).
Ozgur B.M., et al., "Extreme Lateral Interbody Fusion (XLIF): A Novel Surgical Technique for Anterior Lumbar Interbody Fusion," Spine Journal, 2006, vol. 6 (4), pp. 435-443.
Santoni BG., et al., "Cortical Bone Trajectory for Lumbar Pedicle Screws" The Spine Journal, 2009, vol. 9 (5), pp. 366-373.
Willard, F. H., et al., "The Thoracolumbar Fascia: Anatomy, Function and Clinical Considerations." Journal of Anatomy, 2012, vol. 221(6), pp. 507-536.
Abstract for French Patent Publication FR2781359, Published Jan. 28, 2000, entitled: "Osteosynthesis Frame for Spinal Surgery has Rod with Clamps to Hold Cross Bars with Anchor Screws". Accession No. 9867555 (Derwent Information Ltd.).
Abstract for French Patent Publication FR2856271, Published Dec. 24, 2004, Osteo-Synthesis Vertebral Column Plate, has Connection Head Integrated with Plate and Movable in Three Directions of Space So as to Adapt itself to Connection Rod, and Including Opening to Facilitate Introduction of Rod. Accession No. 14694557, (Derwent Information Ltd.).
Andersen T., et al., "Pain 5 years After Instrumented and Non-Instrumented Posterolateral Lumbar Spinal Fusion," European Spine Journal, 2003, vol. 12 (4), pp. 393-399.
Asazuma T., et al., "Intersegmental Spinal Flexibility With Lumbosacral Instrumentation. An In Vitro Biomechanical Investigation," Spine (Phila Pa 1976), 1990, vol. 15 (11), pp. 1153-1158.
Balderston R.A., et al., "Technique for Achievement and Maintenance of Reduction for Severe Spondylolisthesis Using Spinous Process Traction Wiring and External Fixation of the Pelvis," Spine (Phila Pa 1976), 1985, vol. 10 (4), pp. 376-382.
Barbre C.J.,, "Devices for Targeting the Needle," Neurosurgery Clinics of North America, 2009, vol. 20 (2), pp. 187-191.
Bendo J.A., et al., "Instrumented Posterior Arthrodesis of the Lumbar Spine in Patients with Diabetes Mellitus," American Journal of Orthopedics (Belle Mead, NJ), 2000, vol. 29 (8), pp. 617-620.
Benz R.J., et al., "Current Techniques of Decompression of the Lumbar Spine," Clinical Orthopaedics and Related Research, 2001, No. (384), pp. 75-81.
Bostman O., et al., "Posterior Spinal Fusion Using Internal Fixation with the Daab Plate," Acta Orthopaedica Scandinavica, 1984, vol. 55 (3), pp. 310-314.

(56) References Cited

OTHER PUBLICATIONS

Branch C.L., et al., "Posterior Lumbar Interbody Fusion with the Keystone Graft: Technique and Results," Surgical Neurology, 1987, vol. 27 (5), pp. 449-454.
Chen W.J., et al., "Surgical Treatment of Adjacent Instability After Lumbar Spine Fusion," Spine (Phila Pa 1976), 2001, vol. 26 (22), pp. E519-E524.
Chiba M., et al., "Short-Segment Pedicle Instrumentation. Biomechanical Analysis of Supplemental Hook Fixation," Spine (Phila Pa 1976), 1996, vol. 21 (3), pp. 288-294.
Cobo S.J., et al., "Predictors of Outcome After Decompressive Lumbar Surgery and Instrumented Posterolateral Fusion," European Spine Journal, 2010, vol. 19 (11), pp. 1841-1848.
Collins P., Carbon Multiwall Nanotubes: A High Performance Conductive Additive for Demanding Plastics Applications, Materials Integrity Management Symposium, Jun. 2004, Retrieved from the Internet URL :< http://hyperioncatalysis.com/PDFs/CMWNT.pdf>.
"Curve, The Ultimate Control and Information Center" from https://www.brainlab.com/surgery-products/overview-platform-products/curve-image-guided-surgery/, 8 pages, downloaded from the Internet Mar. 27, 2014.
Dar, et al., The Epiphyses Ring: A Long Forgotten Anatomical Structure with Significant Physiological Function (PA 1976). May 15, 2011; 36 (11): 850-6.
Dawson E.G., et al., "Intertransverse Process Lumbararthodesis with Autogenous Bone Graft," Clinical Orthopaedics and Related Research, 1981, No. (154), pp. 90-96.
Deguchi M., et al., "Biomechanical Comparison of Spondylolysis Fixation Techniques," Spine (Phila Pa 1976), 1999, vol. 24 (4), pp. 328-333.
Dove J., "Internal Fixation of the Lumbar Spine. The Hartshill Rectangle," Clinical Orthopaedics and Related Research, 1986, No. (203), pp. 135-140.
Fischgrund J.S., et al., "1997 Volvo Award Winner in Clinical Studies. Degenerative Lumbar Spondylolisthesis with Spinal Stenosis: A Prospective, Randomized Study Comparing Decompressive Laminectomy and Arthrodesis with and without Spinal Instrumentation," Spine (Phila Pa 1976), 1997, vol. 22 (24), pp. 2807-2812.
Freeman B.J., et al., "Posterior Lumbar Interbody Fusion Combined with Instrumented Postero-Lateral Fusion: 5-year Results in 60 Patients," European Spine Journal, 2000, vol. 9 (1), pp. 42-46.
Frogley M.D., et al., "Mechanical Properties of Carbon Nanoparticle-Reinforced Elastomers," Composites Science and Technology, 2003, vol. 63 (11), pp. 1647-1654.
Gibson J.N., et al., "Surgery for Degenerative Lumbar Spondylosis," Cochrane Database of Systematic Reviews, 2005, No. (4), pp. CD001352.
Gill G.G., "Long-Term Follow-Up Evaluation of a Few Patients with Spondylolisthesis Treated by Excision of the Loose Lamina with Decompression of the Nerve Roots without Spinal Fusion," Clinical Orthopaedics and Related Research, 1984, No. (182), pp. 215-219.
Greenough C.G., et al., "Instrumented Posterolateral Lumbar Fusion. Results and Comparison with Anterior Interbody Fusion," Spine (Phila Pa 1976), 1998, vol. 23 (4), pp. 479-486.
Gunzburg R., et al., "The Conservative Surgical Treatment of Lumbar Spinal Stenosis in the Elderly," European Spine Journal, 2003, vol. 12 (Suppl. 2), pp. S176-S180.
Hajek P.D., et al., "Biomechanical Study of C1-C2 Posterior Arthrodesis Techniques," Spine (Phila Pa 1976), 1993, vol. 18 (2), pp. 173-177.
Heggeness M.H., et al., "Translaminar Facet Joint Screw Fixation for Lumbar and Lumbosacral Fusion. A Clinical and Biomechanical Study," Spine (Phila Pa 1976), 1991, vol. 16 (6 Suppl), pp. S266-S269.
Holland N.R., et al., "Intraoperative Electromyography During Thoracolumbar Spinal Surgery," Spine (Phila Pa 1976), 1998, vol. 23 (17), pp. 1915-1922.
Katz J.N., et al., "Lumbar Laminectomy Alone or with Instrumented or Noninstrumented Arthrodesis in Degenerative Lumbar Spinal Stenosis. Patient Selection, Costs, and Surgical Outcomes," Spine (Phila Pa 1976), 1997, vol. 22 (10), pp. 1123-1131.
Kis A., et al., "Reinforcement of Single-Walled Carbon Nanotube Bundles by Intertube Bridging," Nature Materials, 2004, vol. 3 (3), pp. 153-157.
Korkala O., et al., "Reduction and Fixation of Late Diagnosed Lower Ccervical Spine Dislocations Using the Daab Plate. A Report of Two Cases," Archives of Orthopaedic and Trauma Surgery, 1984, vol. 103 (5), pp. 353-355.
Krag M.H., et al., "An Internal Fixator for Posterior Application to Short Segments of the Thoracic, Lumbar, or Lumbosacral Spine. Design and Testing," Clinical Orthopaedics and Related Research, 1986, No. (203), pp. 75-98.
Lin P.M., et al., "Internal Decompression for Multiple Levels of Lumbar Spinal Stenosis: A Technical Note," Neurosurgery, 1982, vol. 11 (4), pp. 546-549.
Liquidmetal Technologies product page from http://liquidmetal.com/our-products/product-parts/, What we Sell, 5 pages, downloaded from the internet Mar. 27, 2014.
Lorenz M., et al., "A Comparison of Single-Level Fusions with and without Hardware," Spine (Phila Pa 1976), 1991, vol. 16 (8 Suppl), pp. S455-S458.
Lowery G.L., "Orion Anterior Cervical Plate System" in: Spinal Instrumentation—Surgical Techniques, Kim D.H., et al., eds., Thieme Medical Publications (New York), 2005, pp. 116-122.
Luque E.R., "Segmental Spinal Instrumentation of the Lumbar Spine," Clinical Orthopaedics and Related Research, 1986, No. (203), pp. 126-134.
Madan S., et al., "Outcome of Posterior Lumbar Interbody Fusion Versus Posterolateral Fusion for Spondylolytic Spondylolisthesis," Spine (Phila Pa 1976), 2002, vol. 27 (14), pp. 1536-1542.
Madan S.S., et al., "Circumferential and Posterolateral Fusion for Lumbar Disc Disease," Clinical Orthopaedics and Related Research, 2003, No. (409), pp. 114-123.
Marotta N., et al., "A Novel Minimally Invasive Presacral Approach and Instrumentation Technique for Anterior L5-S1 Intervertebral Discectomy and Fusion: Technical Description and Case Presentations," Neurosurgical Focus, 2006, vol. 20 (1), pp. E9.
McInerney J., et al., "Frameless Stereotaxy of the Brain," The Mount Sinai Journal of Medicine, 2000, vol. 67 (4), pp. 300-310.
Moskowitz A., "Transforaminal Lumbar Interbody Fusion," Orthopedic Clinics of North America, 2002, vol. 33 (2), pp. 359-366.
Nardi P., et al., "Aperius PercLID Stand Alone Interspinous System for the Treatment of Degenerative Lumbar Stenosis: Experience on 152 Cases," Journal of Spinal Disorders & Techniques, 2010, vol. 23 (3), pp. 203-207.
Neo M., et al., "Spinous Process Plate Fixation As a Salvage Operation for Failed Anterior Cervical Fusion. Technical Note," Journal of Neurosurgery: Spine, 2006, vol. 4 (1), pp. 78-81.
O'Leary P.F., et al., "Distraction Laminoplasty for Decompression of Lumbar Spinal Stenosis," Clinical Orthopaedics and Related Research, 2001, No. (384), pp. 26-34.
Polly D.W., et al., "Surgical Treatment for the Painful Motion Segment: Matching Technology with the Indications: Posterior Lumbar Fusion," Spine (Phila Pa 1976), 2005, vol. 30 (16 Suppl), pp. S44-S51.
Qian D., et al., "Mechanics of Carbon Nanotubes," Applied Mechanics Reviews, 2002, vol. 55 (2), pp. 495-533.
Rapoff A.J., et al., "Biomechanical Comparison of Posterior Lumbar Interbody Fusion Cages," Spine (Phila Pa 1976), 1997, vol. 22 (20), pp. 2375-2379.
Rompe J.D., et al., "Degenerative Lumbar Spinal Stenosis. Long-Term Results After Undercutting Decompression Compared with Decompressive Laminectomy Alone or with Instrumented Fusion," Neurosurgical Review, 1999, vol. 22 (2-3), pp. 102-106.
Rousseau M.A., et al., "Predictors of Outcomes After Posterior Decompression and Fusion in Degenerative Spondylolisthesis," European Spine Journal, 2005, vol. 14 (1), pp. 55-60.
Sasso R.C., et al., "Translaminar Facet Screw Fixation," World Spine Journal, 2006, vol. 1 (1), pp. 34-39.
Sidhu K.S., et al., "Spinal Instrumentation in the Management of Degenerative Disorders of the Lumbar Spine," Clinical Orthopaedics and Related Research, 1997, No. (335), pp. 39-53.

(56) References Cited

OTHER PUBLICATIONS

Smith M.D., et al., "A Biomechanical Analysis of Atlantoaxial Stabilization Methods Using a Bovine Model. C1/C2 Fixation Analysis," Clinical Orthopaedics and Related Research, 1993, No. (290), pp. 285-295.

Stambough J.L., et al., "Instrumented One and Two Level Posterolateral Fusions with Recombinant Human Bone Morphogenetic Protein-2 and Allograft: A Computed Tomography Study," Spine (Phila Pa 1976), 2010, vol. 35 (1), pp. 124-129.

Stambough J.L., "Lumbosacral Instrumented Fusion: Analysis of 124 Consecutive Cases," Journal of Spinal Disorders, 1999, vol. 12 (1), pp. 1-9.

Suzuki Y., "Shape Memory and Super-Elasticity Effects in NiTi Alloys," Titanium-Zirconium, 1982, vol. 30 (4), pp. 185-192.

Swanson K.E., et al., "The Effects of an Interspinous Implant on Intervertebral Disc Pressures," Spine (Phila Pa 1976), 2003, vol. 28 (1), pp. 26-32.

Thomsen K., et al., "1997 Volvo Award Winner in Clinical Studies. The Effect of Pedicle Screw Instrumentation on Functional Outcome and Fusion Rates in Posterolateral Lumbar Spinal Fusion: A Prospective, Randomized Clinical Study," Spine (Phila Pa 1976), 1997, vol. 22 (24), pp. 2813-2822.

Tseng Y.C., et al., "Monolithic Integration of Carbon Nanotube Devices with Silicon MOS Technology," Nano Letters, 2004, vol. 4 (1), pp. 123-127.

Vaccaro, et al., Principles of Practice of Spine Surgery; Mosby Press, Philadelphia, PA; 2003.

Vamvanij V., et al., "Surgical Treatment of Internal Disc Disruption: An Outcome Study of Four Fusion Techniques," Journal of Spinal Disorders, 1998, vol. 11 (5), pp. 375-382.

Voor M.J., et al., "Biomechanical Evaluation of Posterior and Anterior Lumbar Interbody Fusion Techniques," Journal of Spinal Disorders, 1998, vol. 11 (4), pp. 328-334.

Wang J.C., et al., "Comparison of CD HORIZON SPIRE Spinous Process Plate Stabilization and Pedicle Screw Fixation after Anterior Lumbar Interbody Fusion. Invited Submission from the Joint Section Meeting on Disorders of the Spine and Peripheral Nerves, Mar. 2005," Journal of Neurosurgery: Spine, 2006, vol. 4 (2), pp. 132-136.

Wang J.C., et al., "SPIRE Spinous Process Stabilization Plate: Biomechanical Evaluation of a Novel Technology. Invited Submission from the Joint Section Meeting on Disorders of the Spine and Peripheral Nerves, Mar. 2005," Journal of Neurosurgery: Spine, 2006, vol. 4 (2), pp. 160-164.

Webster T.J., et al., "Increased Osteoblast Adhesion on Nanophase Metals: Ti, Ti6Al4V, and CoCrMo," Biomaterials, 2004, vol. 25 (19), pp. 4731-4739.

Wohns R.N.W., et al., Day Surgery for Anterior Cervical Microdiskectomy: Experience with 75 Cases, Jul. 11, 2002, pp. 1-3.

Wood M.J., et al., "Improving Accuracy and Reducing Radiation Exposure in Minimally Invasive Lumbar Interbody Fusion," Journal of Neurosurgery: Spine, 2010, vol. 12 (5), pp. 533-539.

Yang C.K., et al., "Binding energies and electronic Structures of Adsorbed Titanium Chains on Carbon Nanotubes," Physical Review 66, 2002, 041403-1.

Yerby S., et al., "The Effect of Cutting Flute Design on the Insertion and Pullout Properties of Self-tapping Bone Screws," Jul. 2, 2002, pp. 1-2.

"Flexural Pivot Bearings for Frictionless Applications" printout of web page as displayed from Feb. 10, 2010 accessed Sep. 16, 2019 via the Internet Wayback Machine. https://web.archive.org/web/20100210030115/http://www.flexpivots.com/.

Abstract for German Patent No. DE10035182. (Derwent Information Ltd.), publication date Feb. 7, 2002.

\* cited by examiner

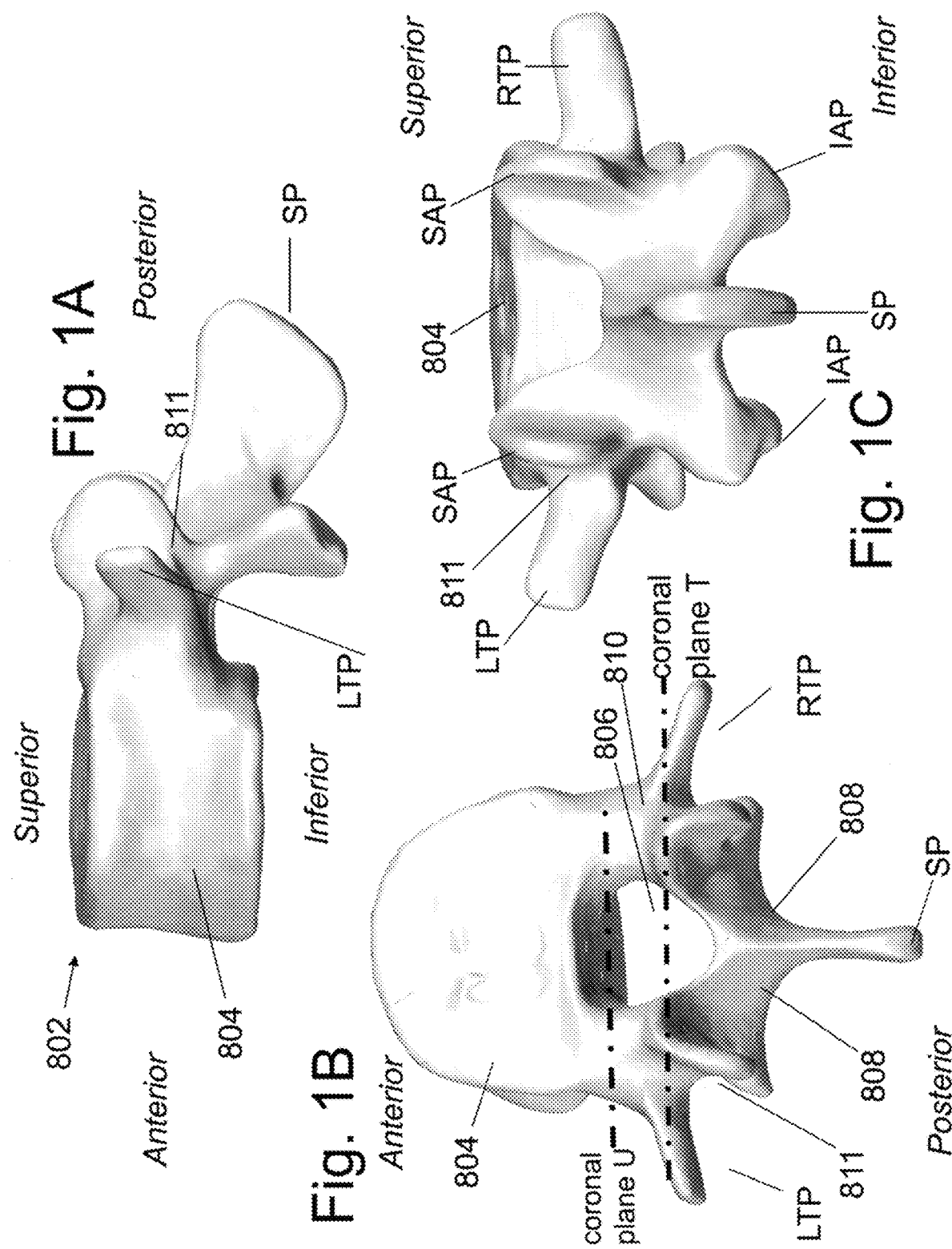

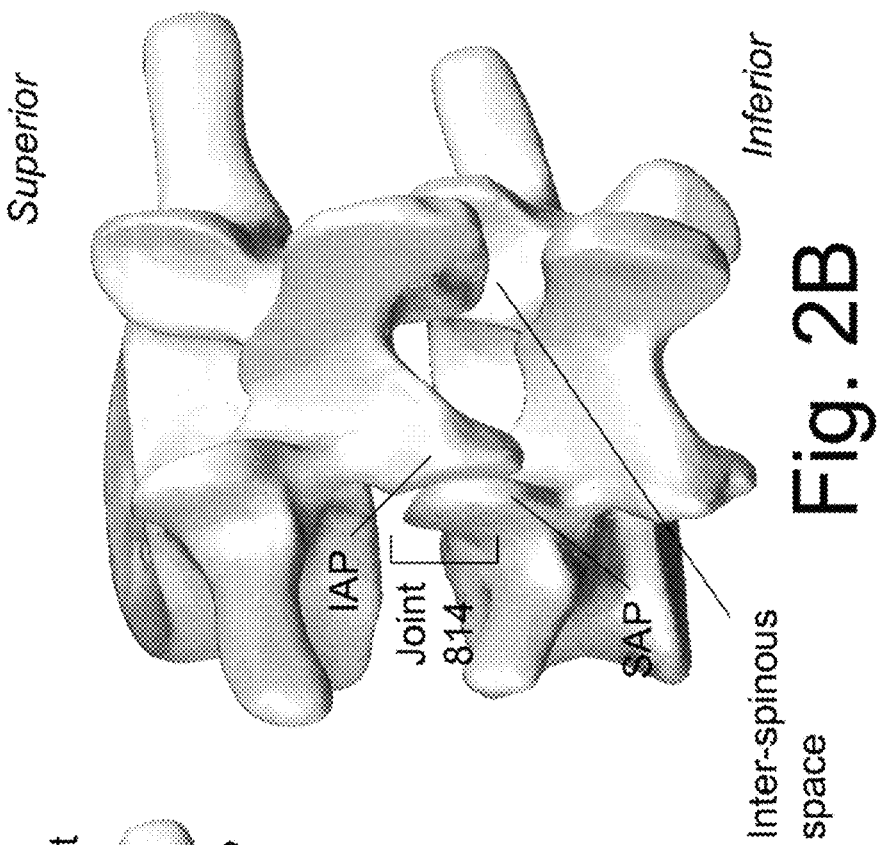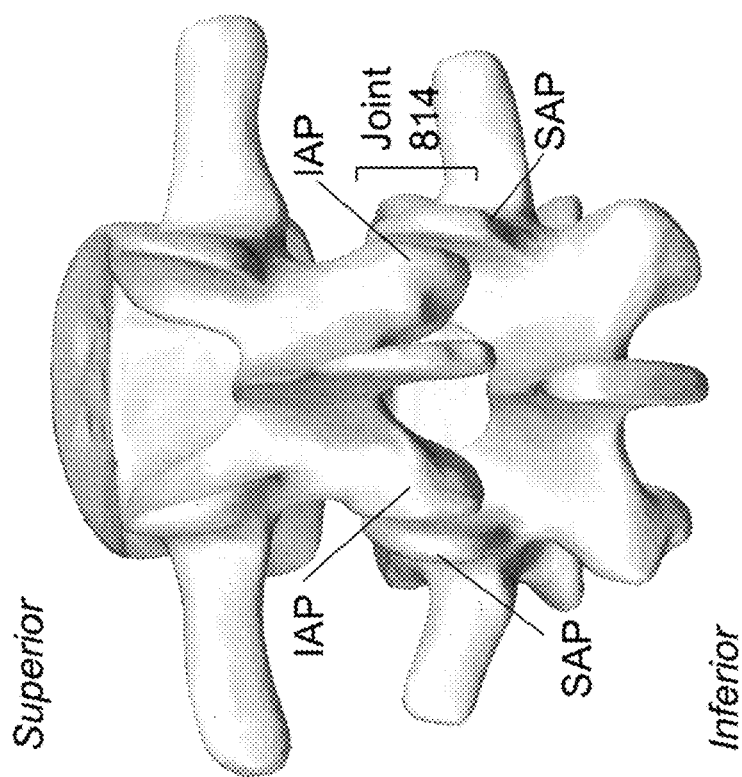

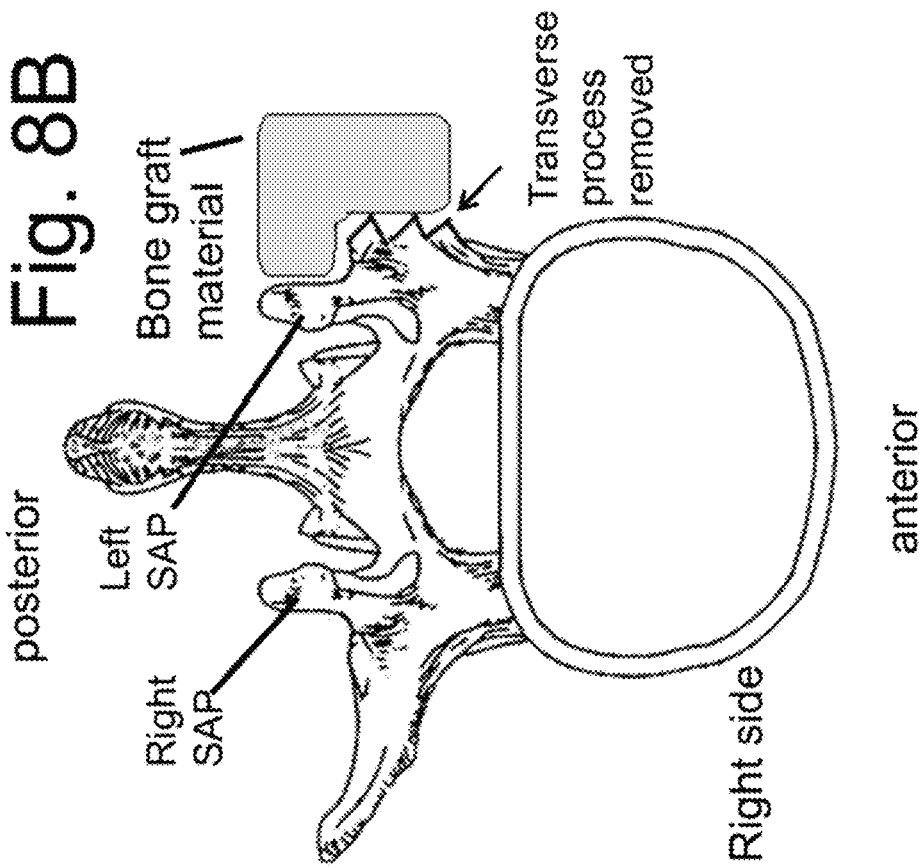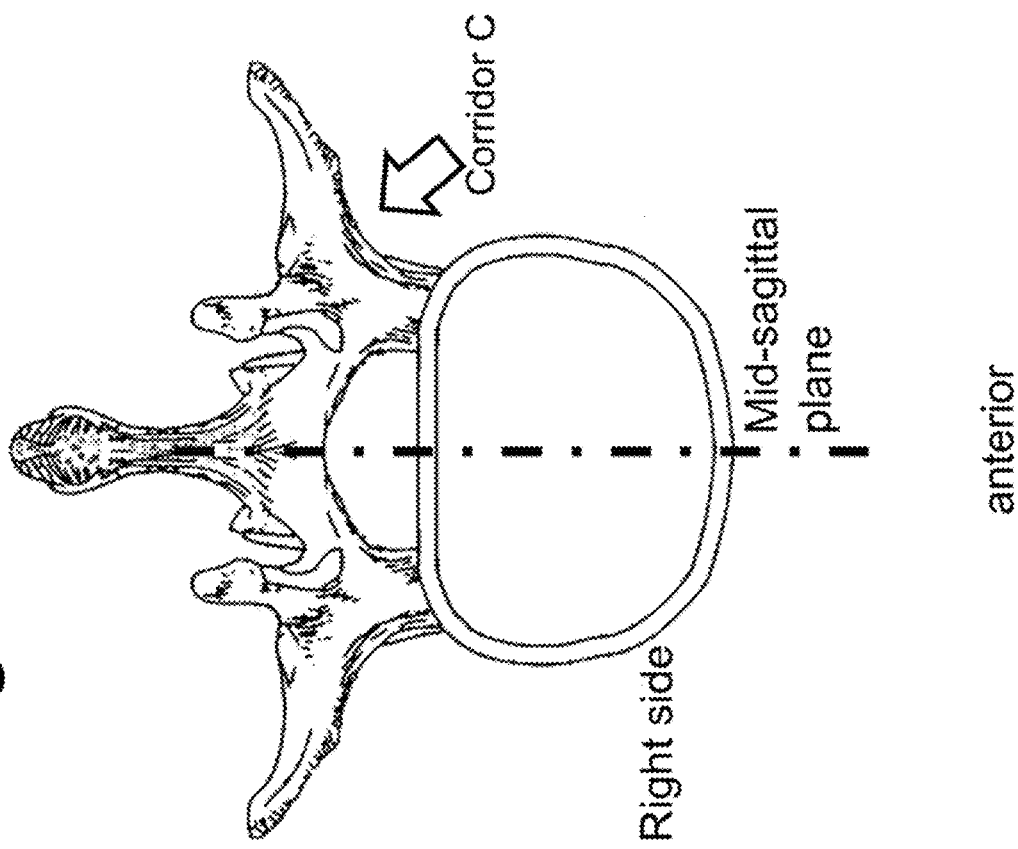

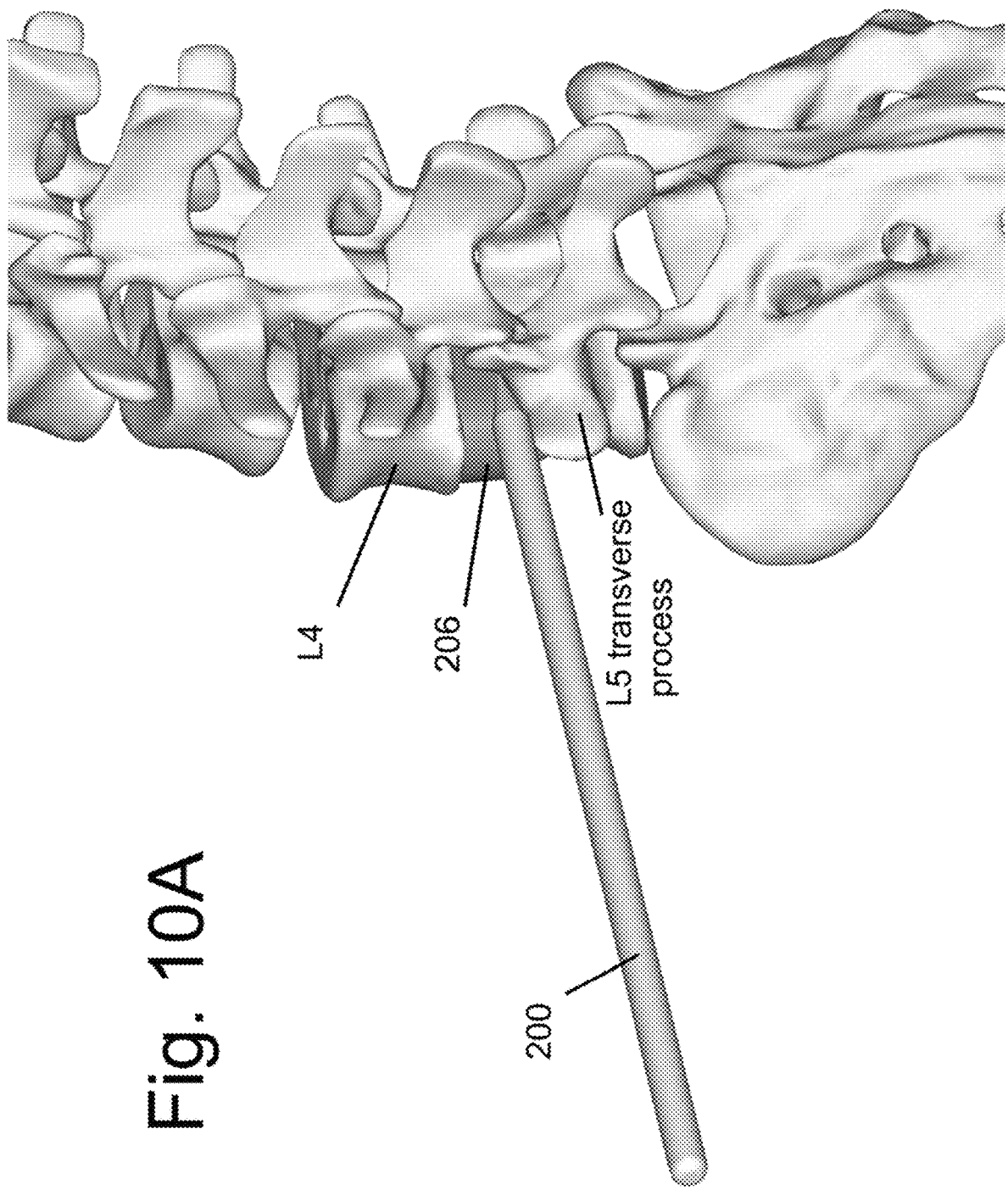

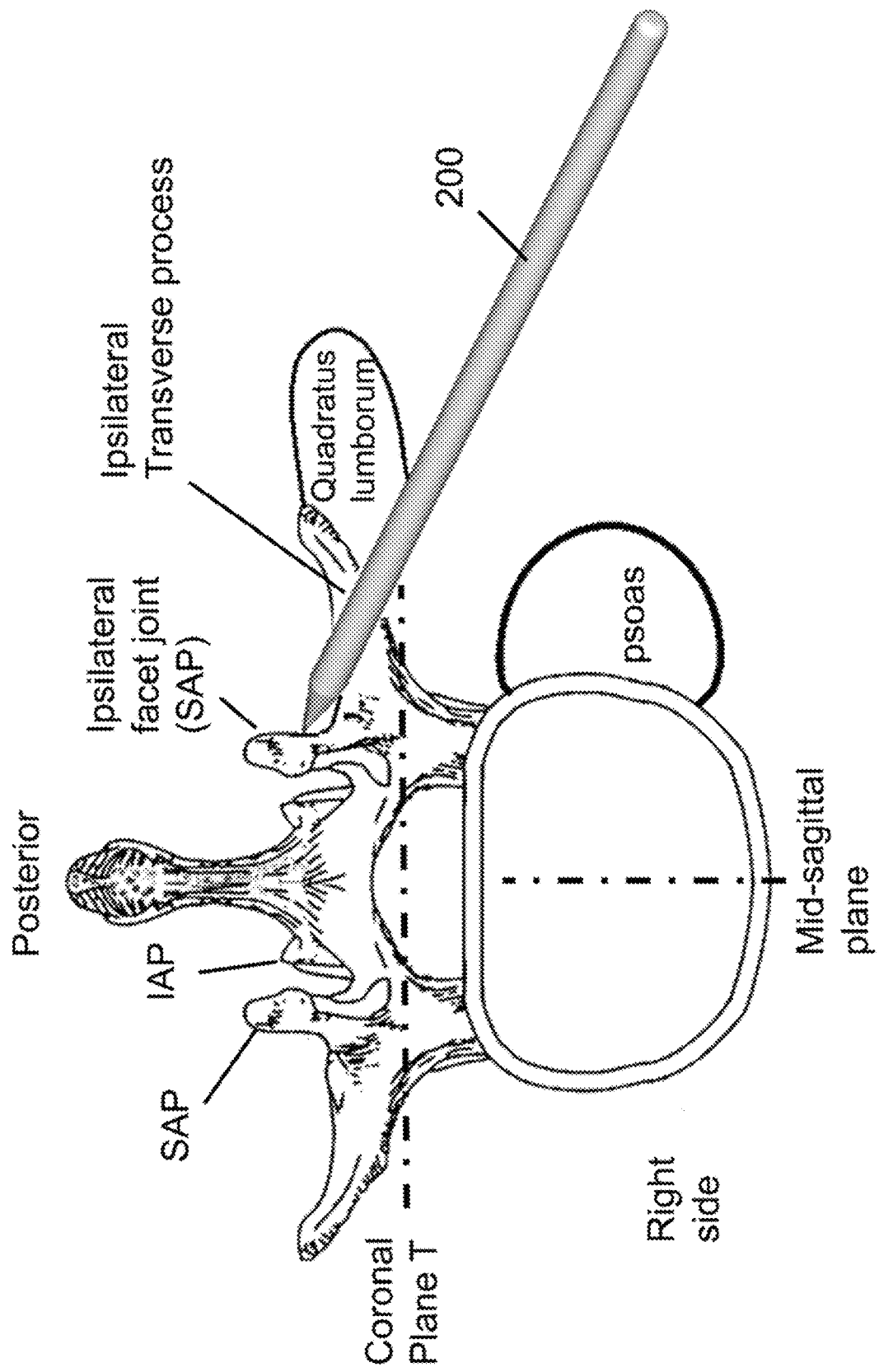

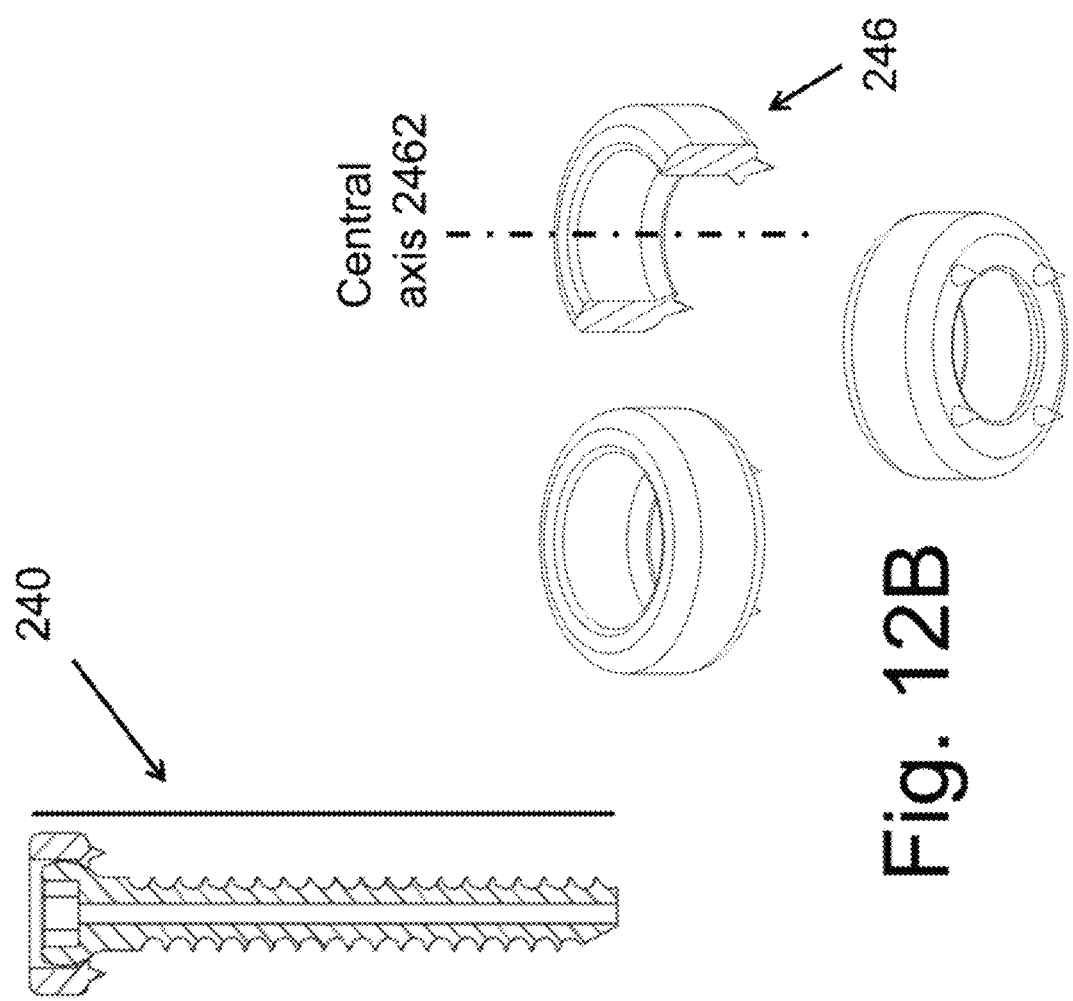
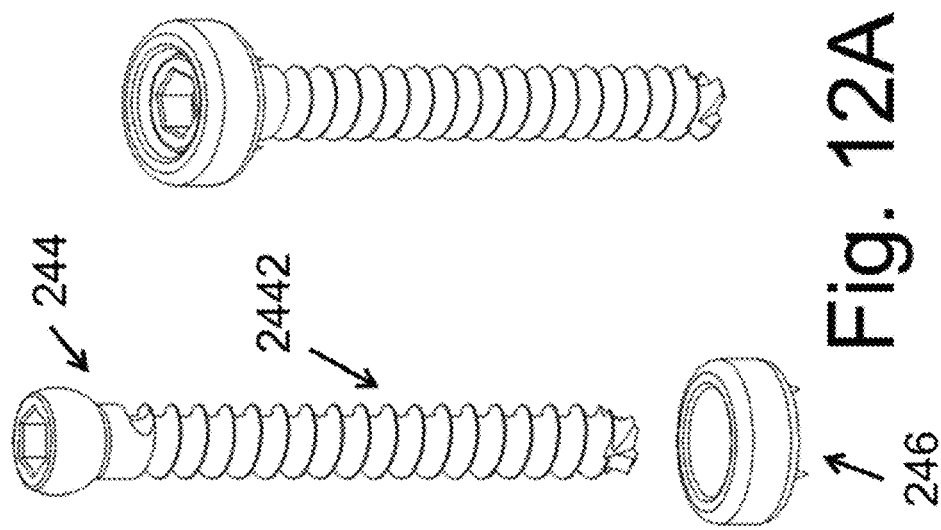
Fig. 12A
Fig. 12B

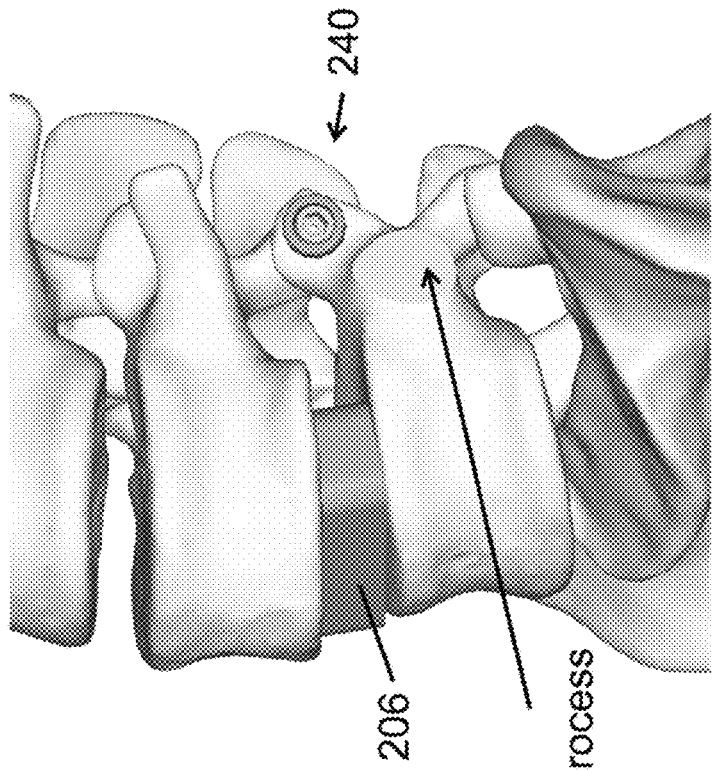
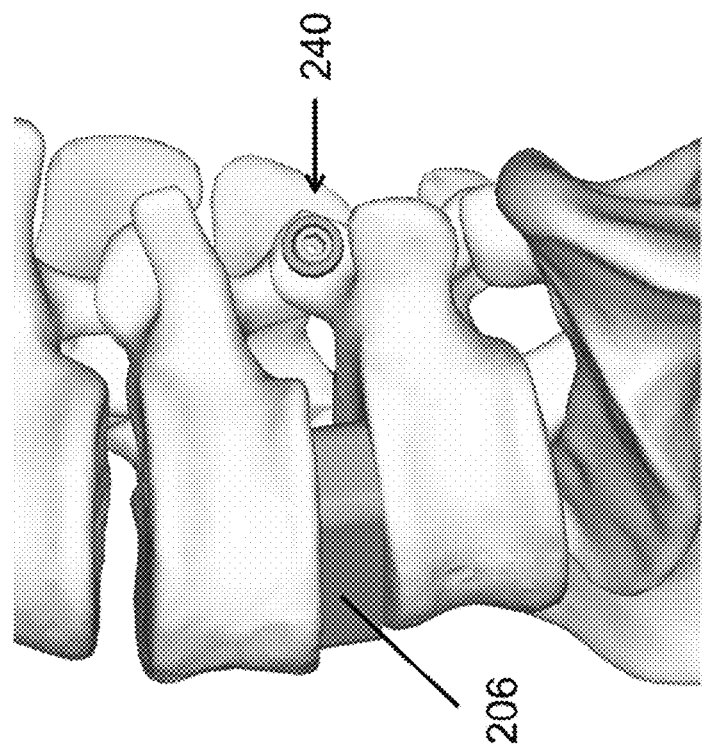

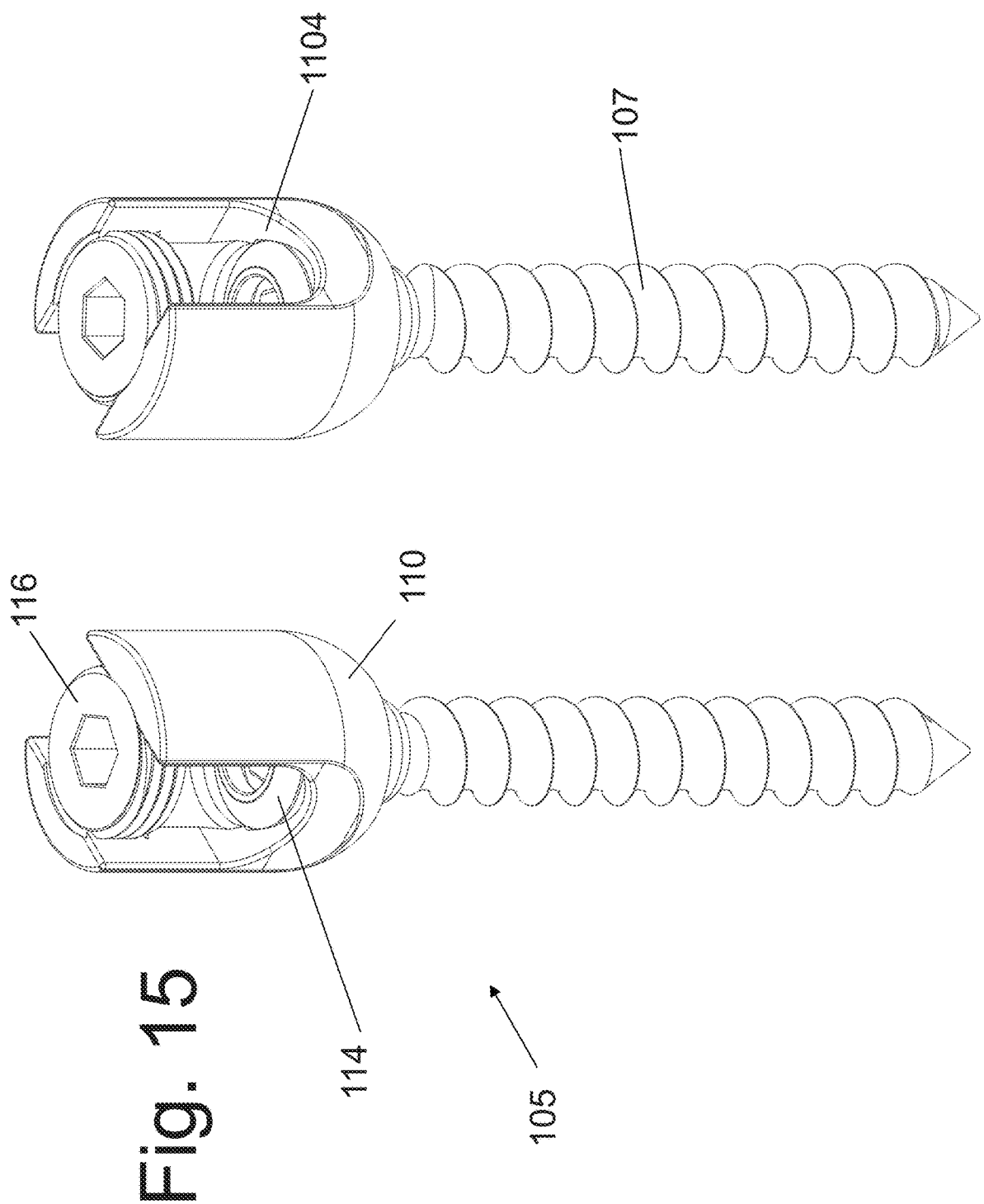

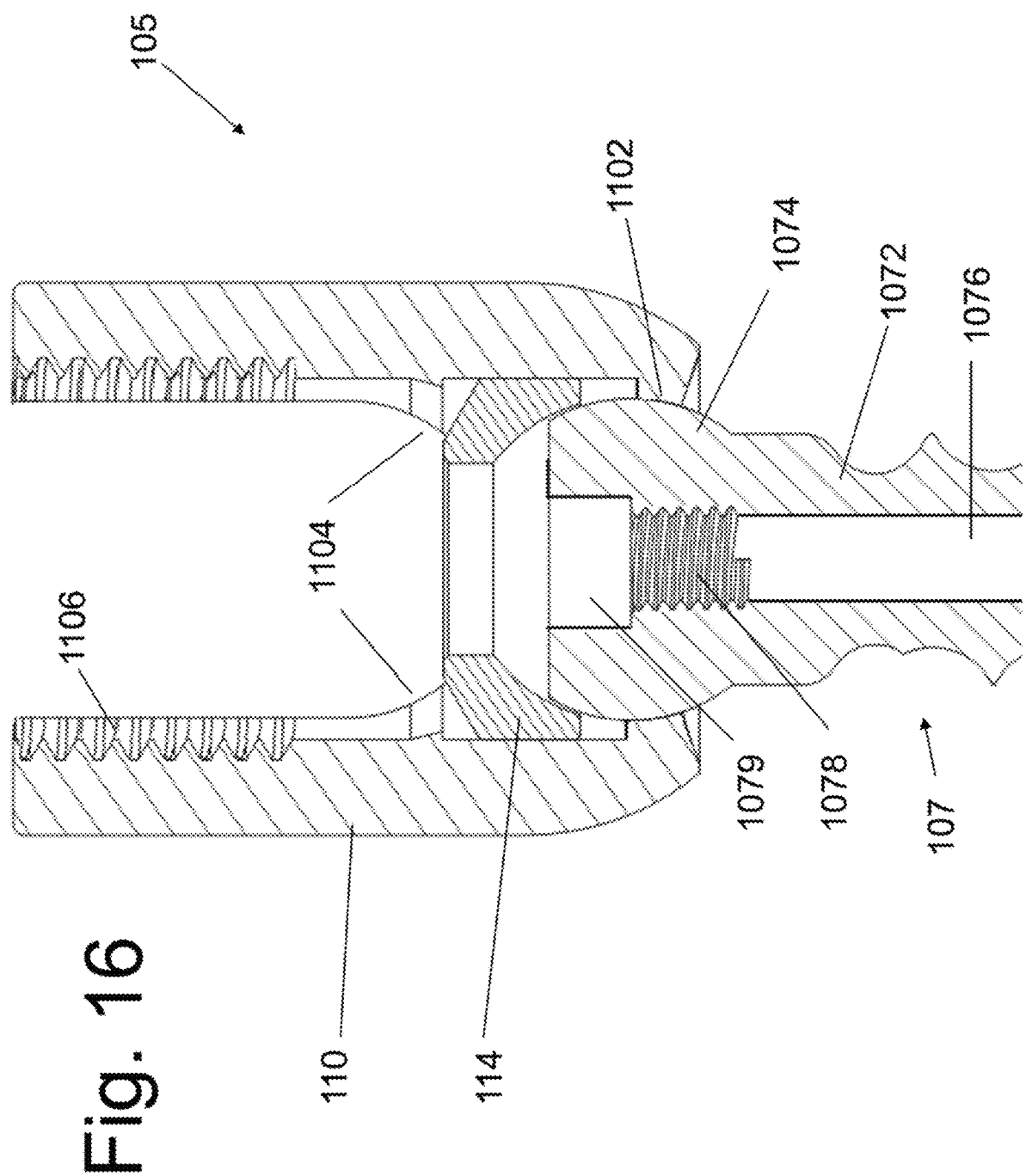

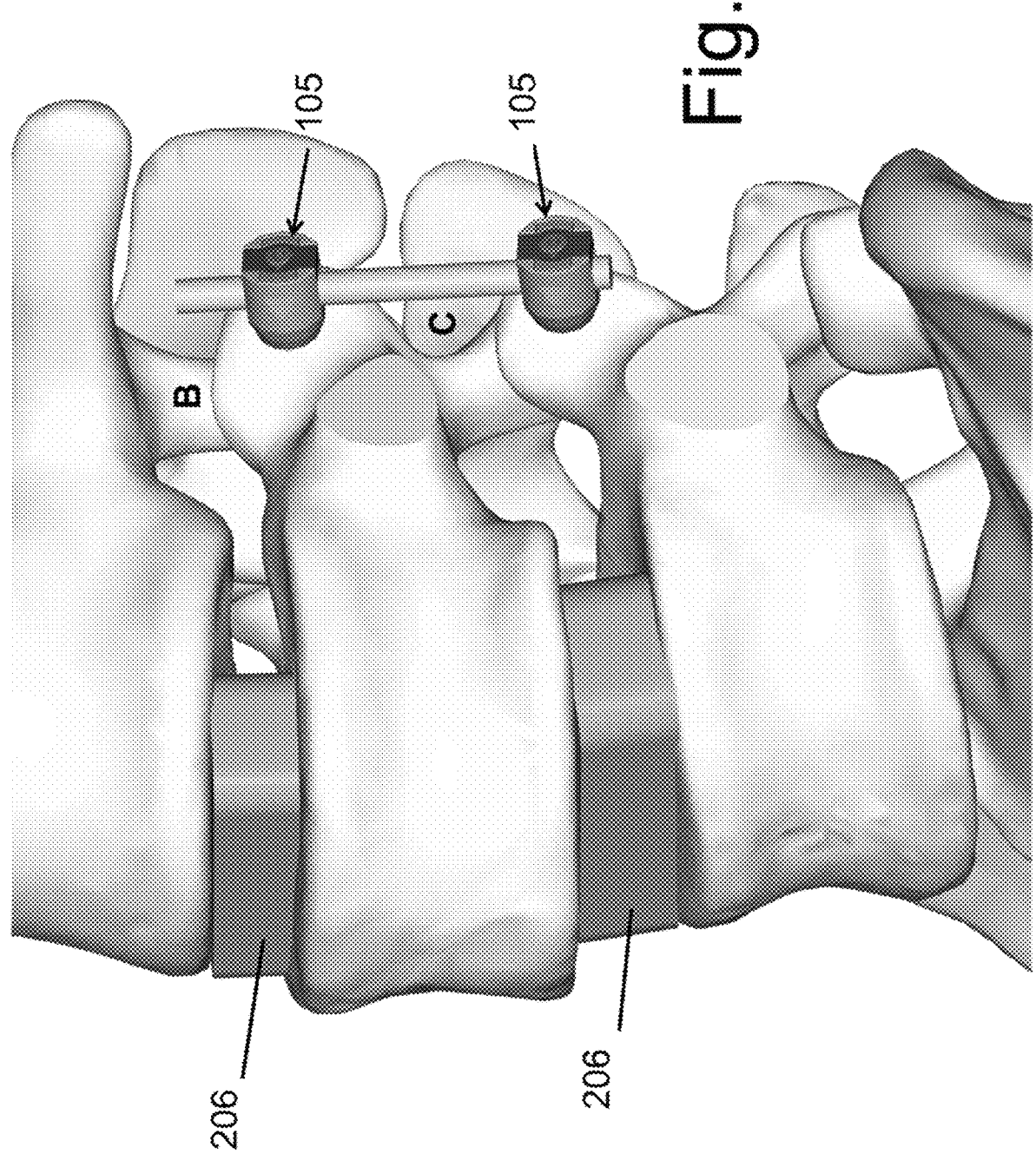

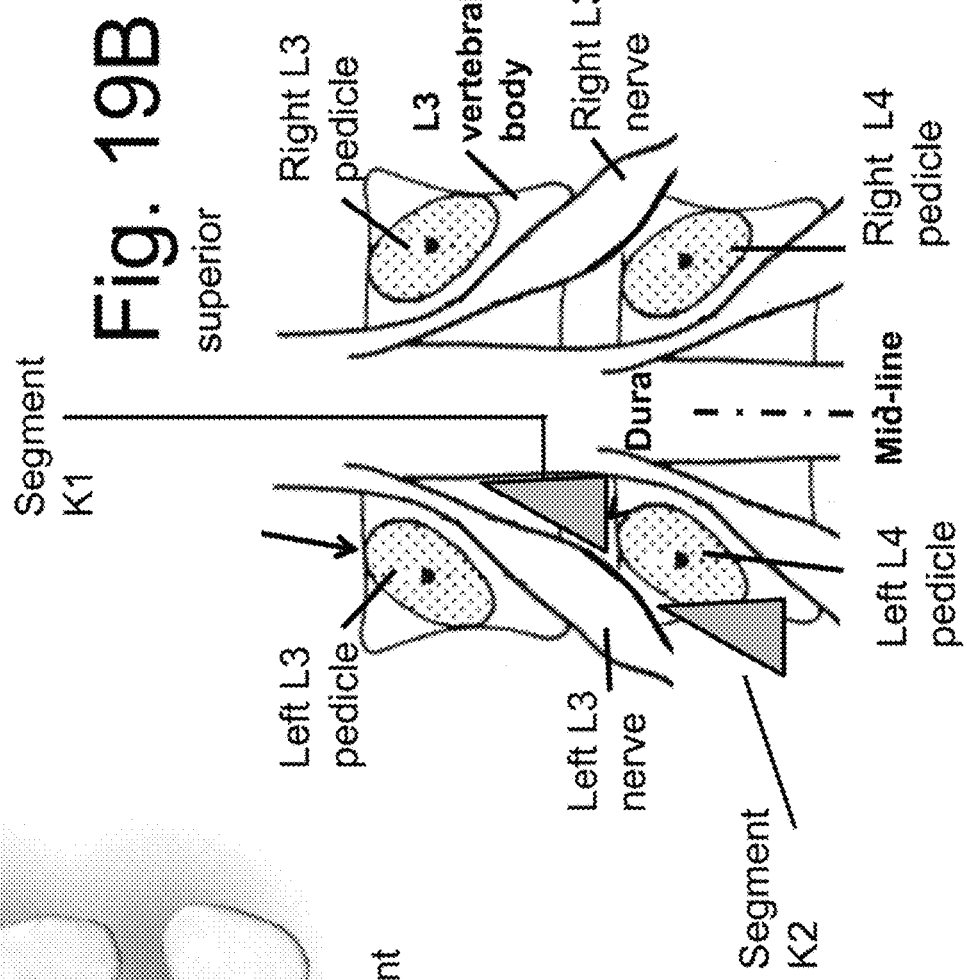

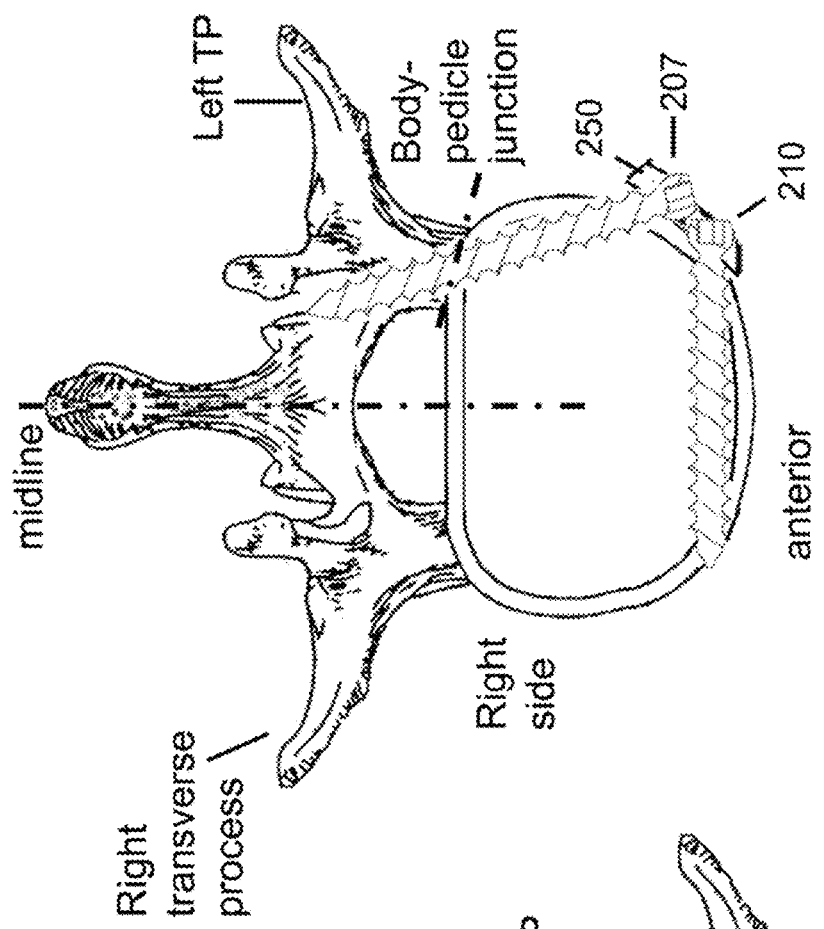
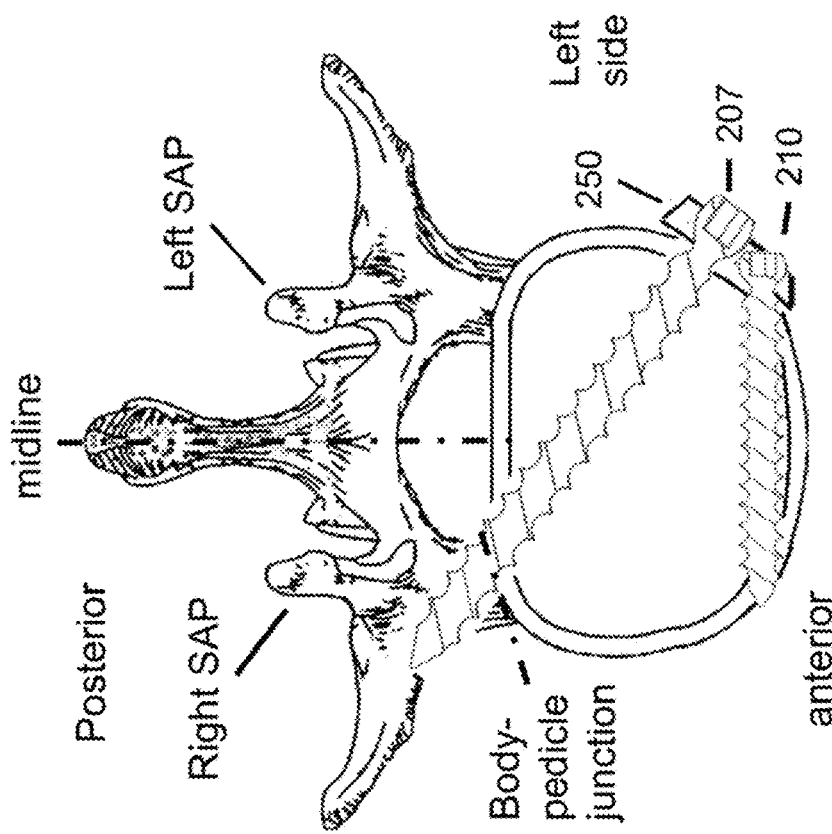

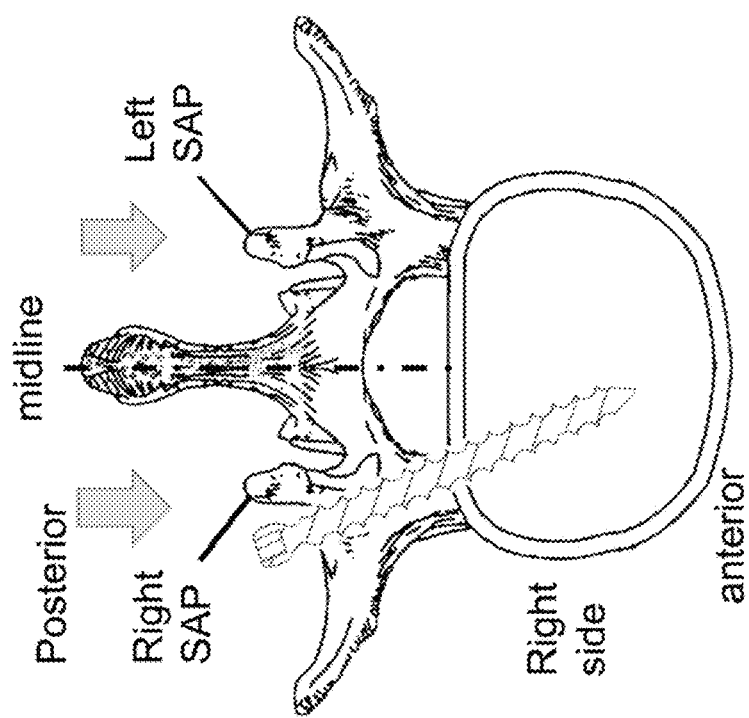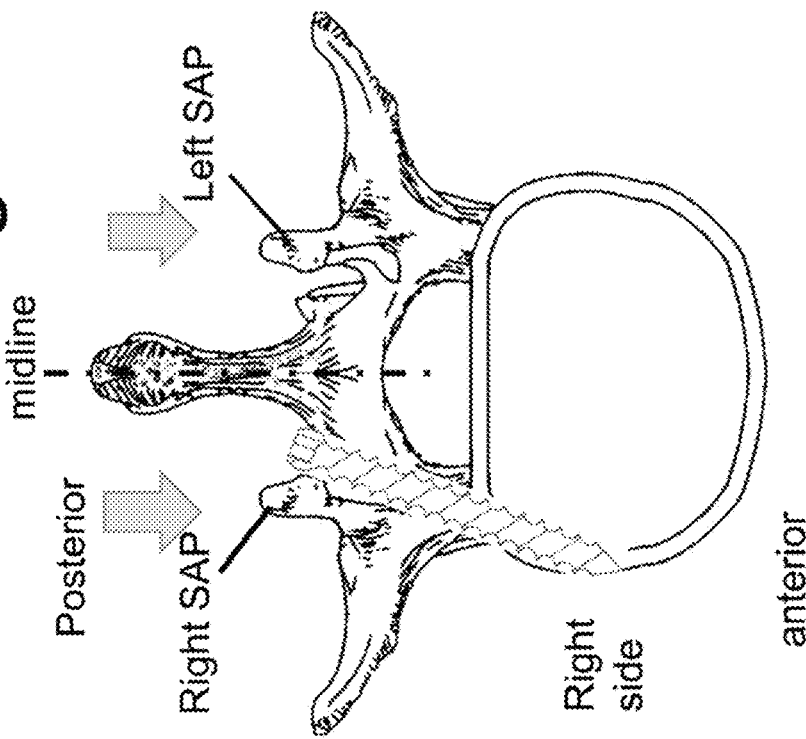

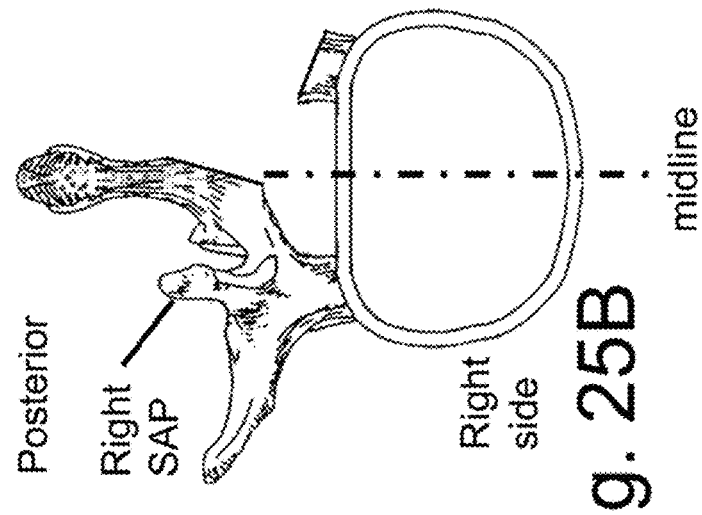
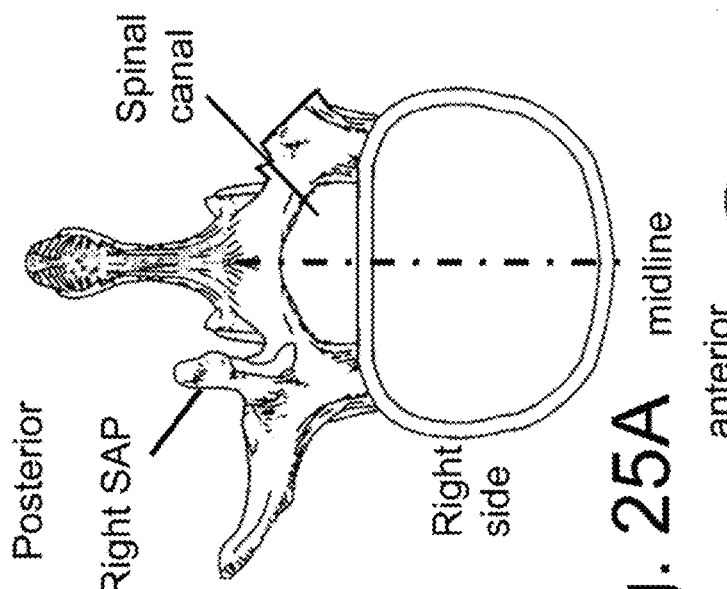
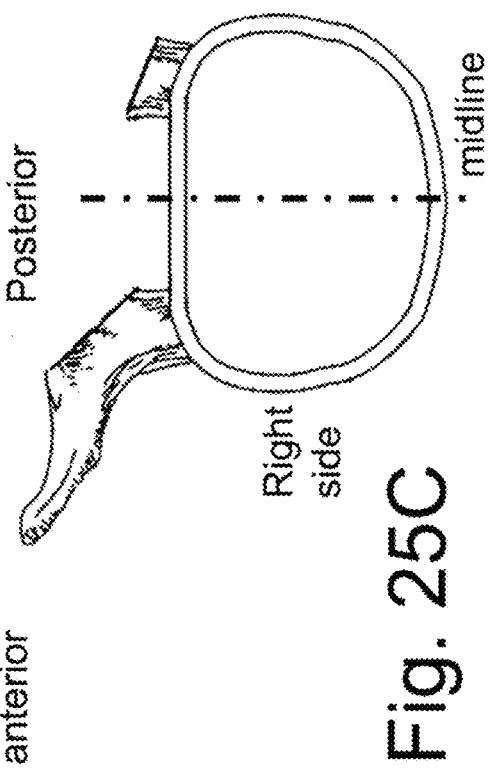
Fig. 25A
Fig. 25B
Fig. 25C

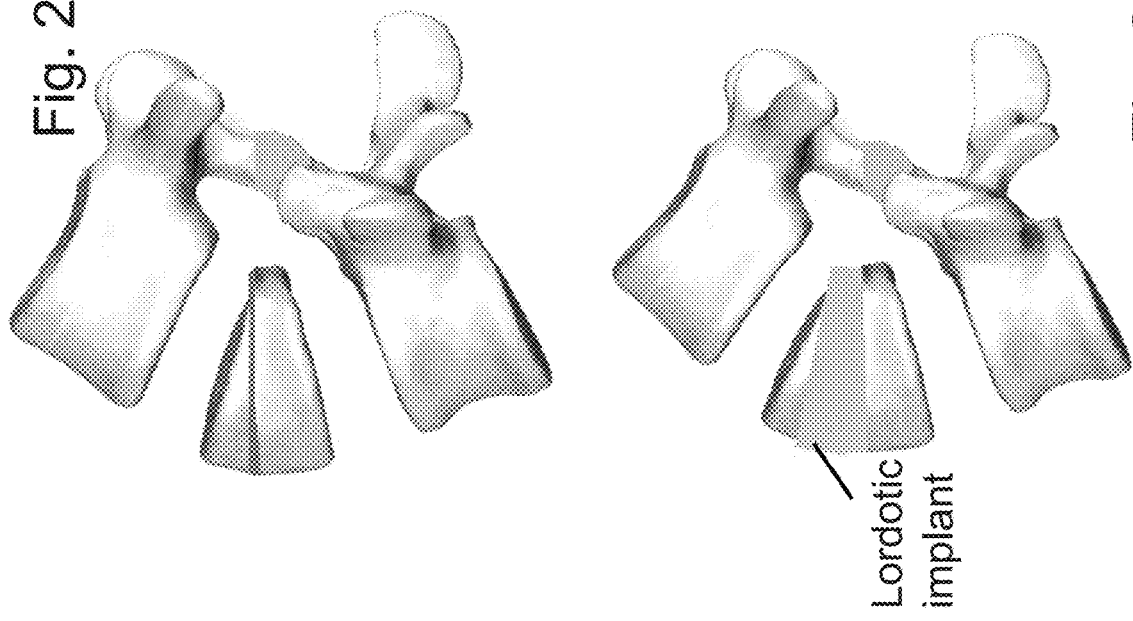
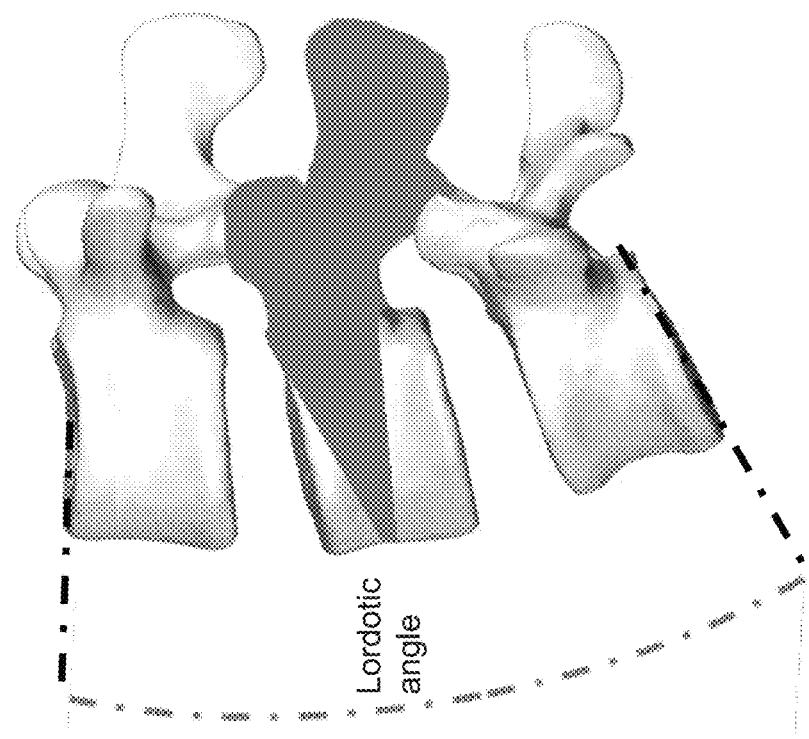

DEVICES AND METHODS FOR VERTEBRAL STABILIZATION

PRIORITY

This application claims priority to U.S. Provisional Patent Application Ser. No. 62/284,944 entitled "SPINAL FIXATION DEVICES AND METHODS OF USE", filed Oct. 14, 2015, which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Disclosure

This disclosure relates generally to bone fixation systems, components thereof, and methods of implant placement for adjusting, aligning and maintaining the spatial relationship(s) of adjacent bones or bony fragments, such as for example after surgical reconstruction of skeletal segments.

2. Description of Related Technology

Whether from degenerative disease, traumatic disruption, infection or neoplastic invasion, alteration in the anatomical relationships between the spinal vertebras can cause significant pain, deformity and disability. Spinal disease is a major health problem in the industrialized world, and the surgical treatment of spinal pathology is an evolving discipline. The traditional surgical treatment of abnormal vertebral motion is the complete immobilization and bony fusion of the involved spinal segment and an extensive array of surgical techniques and implantable devices have been formulated to accomplish the treatment objective.

Regardless of the specific objectives of surgery, many surgeons employ implantable devices that maintain the desired spatial relationship(s) between adjacent vertebral bodies. The effectiveness of these devices is critically dependent on adequate fixation into the underlying bone. Adequate access and fixation of both the anterior and posterior spinal columns often requires multiple incisions and surgical corridors. Therefore, such procedures continue to be substantial operations with a multitude of shortcomings, including without limitation increased trauma to the patient, extended recovery time after surgery, and enhanced risk for surgical complications such as infection. Such problems can further be exacerbated when the patient is elderly, and/or has compromised physiology in one respect or another.

Hence, there is a salient need for alternative methods of implant placement and bony fixation, and associated apparatus, in order to, inter alia, reduce the necessary degree and scope surgery and associated surgical risk, particularly in aging populations.

SUMMARY

The present disclosure addresses the foregoing needs by disclosing, inter alia, apparatus and methods for the treatment of abnormal spinal stability and stenosis of the spinal canal, including by providing decompression and/or fixation thereof.

In a first aspect, a method for stabilization of an anatomical portion of a subject is disclosed. In one embodiment, the anatomical portion comprises a target functional spinal unit (FSU) of a living subject, and the method includes: (i) forming a first tissue corridor; (ii) accessing and manipulating an anterior portion of the target FSU via the first tissue corridor; (iii) forming a second tissue corridor; and (iv) accessing and manipulating a posterior portion of the target FSU via the second tissue corridor.

In one variant, the forming a first tissue corridor includes forming the corridor from a skin incision to a side surface of the target FSU, with the first tissue corridor extending at least partially through an abdominal cavity of the subject.

In another variant, the forming of the second tissue corridor includes forming a corridor that is extended posterior to a psoas major muscle and through a thoraco-lumbar fascia of the subject.

In another embodiment, the method includes: (i) forming a tissue corridor from a skin incision to a side surface of the functional spinal unit, the tissue corridor extended at least partially through an abdominal cavity of the subject; (ii) accessing an anterior portion of the target FSU through the tissue corridor; and (iii) accessing a lateral aspect of an ipsilateral pedicle of an inferior vertebral bone of the target FSU, and (iv) advancing at least one bone fastener into the inferior vertebral bone, the at least one bone fastener extended in a lateral to medial trajectory.

In yet another embodiment, the method includes: (i) forming a tissue corridor from a skin incision to a side surface of the target FSU, the tissue corridor extended at least partially through an abdominal cavity of the subject; (ii) accessing an anterior portion of the target FSU through the tissue corridor and positioning an orthopedic implant within an intervertebral disc space of the target FSU; (iii) extending the tissue corridor posterior to a psoas major muscle; and (iv) accessing a lateral surface of a superior articulating process of a facet joint of the target FSU via the extended tissue corridor.

In yet a further embodiment, the method includes: (i) forming a first tissue corridor from a skin incision to a side surface of the target FSU, the first tissue corridor at least partially extended through an abdominal cavity of the subject; (ii) accessing an anterior portion of the target FSU through the first tissue corridor; (iii) extending the first tissue corridor posterior to a psoas major muscle; (iv) accessing an anterior surface of a transverse process of the target FSU via the extended first tissue corridor; (v) forming a second tissue corridor from a posterior skin incision one a back of the subject to a posterior aspect of at least one vertebral bone of the target FSU; and (vi) advancing a bone fastener into the posterior aspect of the at least one vertebral bone via the second tissue corridor.

In still another embodiment, the method includes: (i) forming a tissue from a skin incision to a side surface of the target FSU, the tissue corridor extended at least partially through an abdominal cavity of the subject; (ii) accessing an anterior portion of the target FSU through the tissue corridor; and (iii) advancing at least one bone fastener through a side surface of a body segment of a vertebral bone of the target FSU. In one variant, the trajectory of the at least one bone fastener is extended in an anterior to posterior direction and enters at least a segment of a pedicle portion of the vertebral bone to which the fastener is attached.

In a second aspect, a method for accessing a targeted functional spinal unit (FSU) for manipulation and/or fixation is disclosed. In one embodiment, the method includes: (i) creating at least one first tissue corridor through at least one of flank skin and/or abdominal skin of a subject to an anterior or a lateral portion of the targeted FSU; and (ii) creating at least one second tissue corridor through posterior skin of the subject.

In one variant, the second corridor extends along a plane between the ipsilateral psoas major muscle and the quadratus lumborum muscle to a posterior portion of the targeted FSU, and the at least one first tissue corridor comprises a direct anterior approach.

In another variant, the at least one first tissue corridor comprises an anterolateral approach. In yet another variant, the at least one first tissue corridor comprises a direct lateral approach.

In still another variant, the first tissue corridor extends at least partially through an abdominal cavity of the subject.

In a third aspect, a method for immobilization of a facet joint of a targeted FSU is disclosed. In one embodiment, the method comprises: (i) removing at least a portion of a nucleus pulposus of an intervertebral disc space of the facet joint via a first tissue corridor; (ii) implanting one or more orthopedic implants into an intervertebral disc space of the facet joint via the first tissue corridor; and (iii) attaching one or more bone fasteners to the targeted FSU via advancement through a second tissue corridor. In one variant, the first tissue corridor is formed through flank skin and/or abdominal skin of a subject to an anterior or a lateral portion of the targeted FSU. In another variant, the second tissue corridor is formed through posterior skin of the subject along a plane between the ipsilateral psoas major muscle and the quadratus lumborum muscle to a posterior portion of the targeted FSU.

In yet another variant, the method further comprises removal of one or more of the ipsilateral transverse processes of a superior and/or inferior vertebral bone of the targeted FSU via the second tissue corridor. In one implementation, at least a portion of the removed one or more ipsilateral transverse processes is inserted into the intervertebral disc space and utilized as a bone graft material for the one or more implants.

In a fourth aspect, a method of providing decompression of spinal stenosis is disclosed. In one embodiment, the method comprises: (i) accessing a facet joint of a target FSU via a tissue corridor, the tissue corridor extended posterior to a psoas major muscle, anterior to a quadratus lumborum muscle, and through a thoraco-lumbar fascia; and (ii) removing at least a portion of the ipsilateral facet joint. In one variant, the method further comprises rigidly fixing a position of the target FSU via one or more orthopedic implants and/or bone fasteners advanced through the tissue corridor.

In another aspect, a method of achieving circumferential access to an FSU is disclosed. In one embodiment, the method includes approaching the FSU through an intra-abdominal corridor, as well as a second posterior skin incision and corridor. The combination of the intra-abdominal corridor and second posterior corridor provide circumferential access to the FSU.

In another aspect of the disclosure, an implantable bone fastener assembly is disclosed. In one embodiment, the bone fastener assembly includes a threaded bone screw with threaded shaft and a shaped (e.g., spherical) head portion. In one variant, an internal bore extends through the internal aspect of the screw, extending from the top of the head portion to a tip of shaft. The internal bore in one implementation includes a threaded portion, and a polygonal (e.g., hex) shaped receptacle resides within the head.

In another implementation, an outer housing is included, and has an internal seat adapted to seat the head of the screw. The housing also has an additional seat that is adapted to accept an inter-connecting member, such as a rod.

In a further aspect, a system for spinal treatment is disclosed. In one embodiment, the system includes at least first and second bone fastener elements for fixation to respective bones or bone portions of the spine of the subject, and a connecting element (e.g., rod) for mechanical stabilization of the spine. One or more inter-disc implants are also utilized as part of the system.

In yet other aspects, methods and apparatus for treating patients are disclosed. The details of one or more embodiments are set forth in the accompanying drawings and description below. Other features, objects, and advantages will be apparent from the following description, the accompanying drawings and from the claims.

BRIEF DESCRIPTION OF THE DRAWINGS

FIGS. 1A-1C are a side elevation view, a top plan view, and a posterior elevation view, respectively, of an exemplary vertebral bone.

FIGS. 2A and 2B are a posterior elevation view and a posterior perspective view of an exemplary functional spinal unit (FSU) comprised of two adjunct vertebral bones and an intervening disc space.

FIGS. 8A and 8B are top plan views of a subject's spine illustrating access and possible resection of the transverse process via Corridor C.

FIGS. 10A and 10B are posterior perspective and top plan views of a subject's spine, respectively, illustrating access of the facet joint via Corridor C.

FIGS. 12A and 12B are each perspective and cross-sectional views of an embodiment of a facet screw/fastener assembly.

FIGS. 13A and 13B and 14 are anterior perspective views (FIGS. 13A and 13B) and a posterior perspective view (FIG. 14) of a subject's spine illustrating the facet screw/fastener of FIGS. 12A and 12B in place.

FIGS. 15 and 16 are top perspective views and a cross-sectional view, respectively, of a bone fastener assembly that is adapted to couple with an interconnecting rod.

FIG. 17 is an anterior perspective view of a subject's spin illustrating the bone fastener assembly of FIGS. 15 and 16 in use.

FIGS. 19A and 19B are a side perspective view and a schematic representation of a subject's spine illustrating a corridor and a bone segment for bone screw/fastener placement.

FIGS. 20A and 20B are top plan views of a subject's spine illustrating additional embodiments of bone screw/fastener placement.

FIGS. 23A and 23B are cross-sectional views of a subject's spine illustrating additional embodiments of bone screw/fastener placement.

FIGS. 25A-25C are top plan views of a subject's spine illustrating decompressions that may be accomplished through the access corridors.

FIGS. 26A-26C are side elevation views of a subject's spine illustrating performance of a pedicle subtraction osteotomy through the access corridors, and a potential use of a lordotic implant in performing a pedicle subtraction osteotomy.

Figure 3:
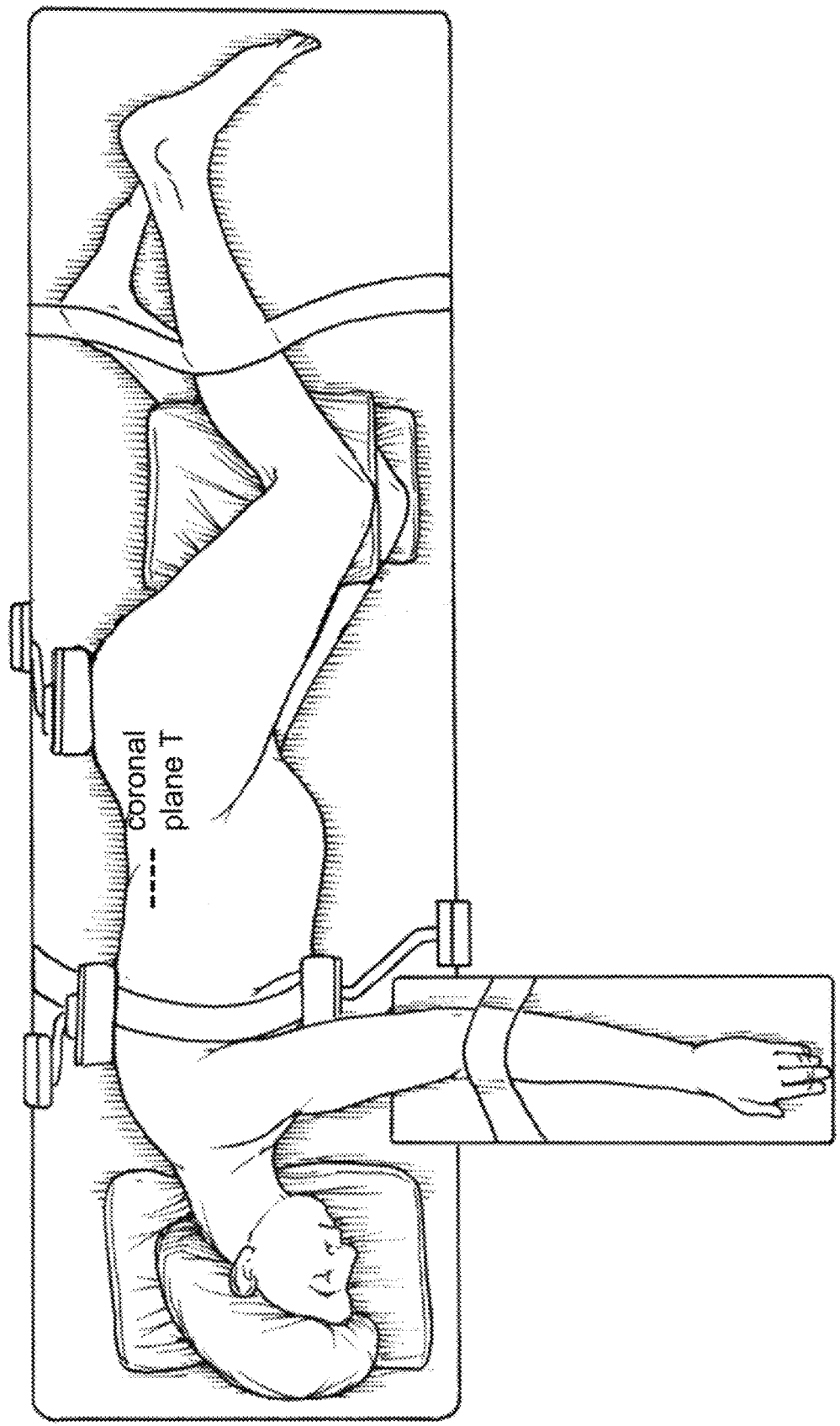
FIG. 3 is a schematic representation of a subject illustrating the positioning of the subject on an operating table.

All Figures© Copyright 2013-2016. Samy Abdou. All rights reserved.

DETAILED DESCRIPTION

In order to promote an understanding of the principals of the disclosure, reference is made to the drawings and the embodiments illustrated herein. Nevertheless, it will be understood that the drawings are illustrative and no limitation of the scope of the claims is intended thereby. Any such alterations and further modifications in the illustrated embodiments, and any such further applications of the principles of the disclosed devices as illustrated herein are contemplated as would normally occur to one of ordinary skill in the art.

Overview

In one aspect, improved devices, systems, and methods for the treatment of abnormal spinal stability and/or stenosis of the spinal canal are disclosed. Specifically, methods for fusion of a superior vertebral bone to an inferior vertebral bone of a target functional spinal unit are disclosed that, inter alia, overcome the disabilities of the prior art described above.

In one embodiment, a skin incision is made in a flank skin and/or abdominal skin of a subject on one side of the mid-sagittal plane that divides the subject into right and left sides. For example, the incision can be positioned anterior to coronal plane T. An intra-abdominal (and, in some examples, extra-peritoneal) surgical corridor is developed from the skin incision through a plane between the ipsilateral psoas major muscle and the ipsilateral quadratus lumborum muscle, and across coronal plane T in anterior to posterior trajectory. Optionally, the ipsilateral transverse process of one or both vertebral bones of the target functional spinal unit may be removed, such as, e.g., the ipsilateral transverse process of the inferior vertebral bone of the target functional spinal unit. When removed, the harvested transverse process may be used, if desired, as a portion of the bone graft material used to fuse the superior and the inferior vertebral bone to one another.

In one implementation, the ipsilateral facet joint may be accessed through corridor C and at least partially removed, if desired, to decompress the nerve elements. The ipsilateral facet joint, whether whole or after partial resection, may be then implanted with one or more fasteners that serve to immobilize and/or limit movement across the facet joint. In some examples, the target intervertebral disc space is also entered, at least a portion of the contained nucleus pulposus is evacuated, and the disc space is then implanted with bone graft material and/or an orthopedic implant that is configured to fuse the adjacent vertebral bone. Additionally, in some examples, at least some of the bone used for the disc space fusion (also known as interbody fusion) may be derived from the resected transverse process. The disc space can advantageously be entered through one of the three potential sites, such that the disc space work may be performed prior to fastener placement and immobilization of the ipsilateral facet joint.

Figure 5:
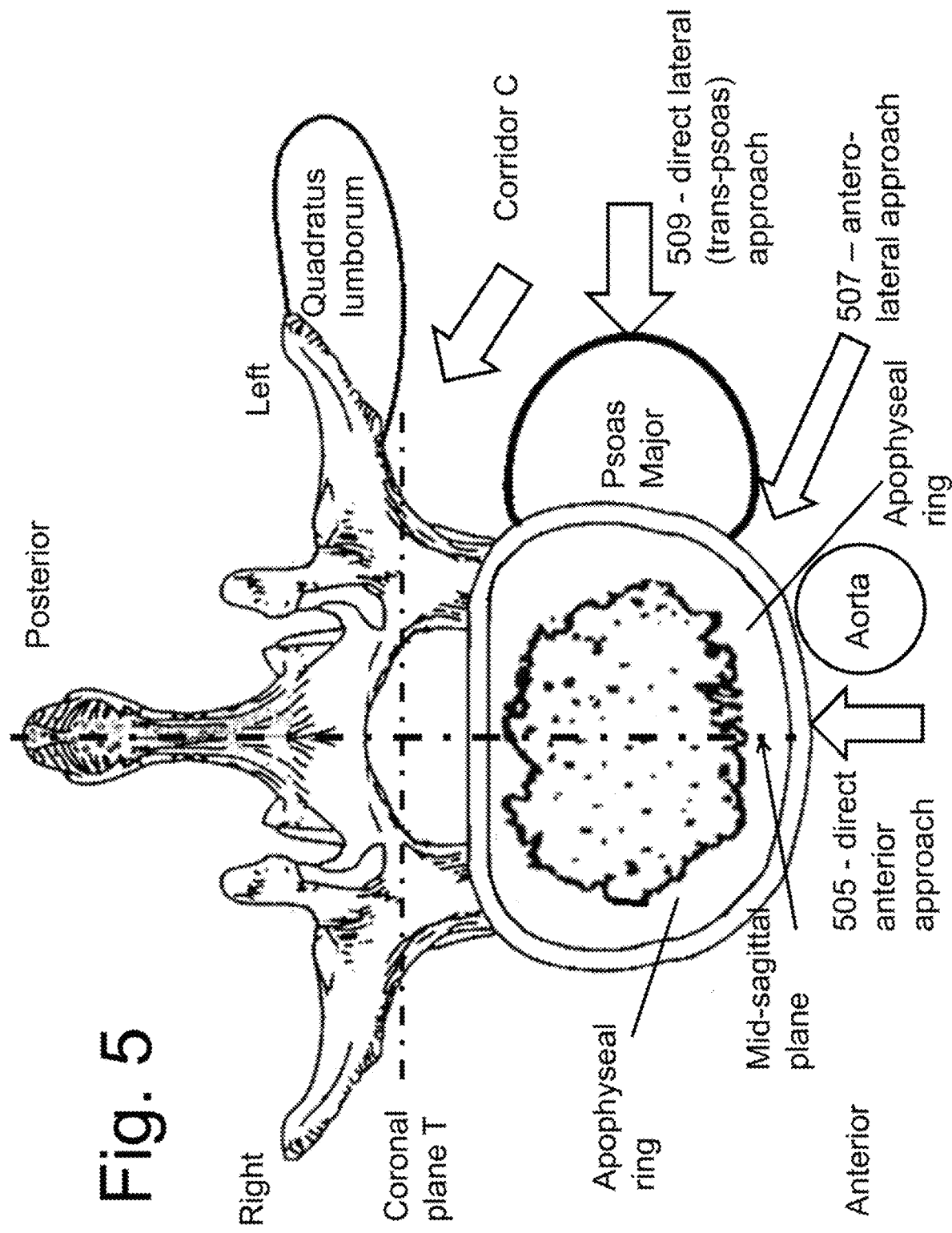
FIG. 5 is a top plan view of a subject's spine illustrating multiple approach corridors to the target vertebral bone.

In another embodiment, the target intervertebral disc space may be entered anterior to the ipsilateral psoas and posterior to the aorta (such as, e.g., an anterolateral approach 507 shown in FIG. 5). At least a portion of the nucleus pulposus is removed and the disc space is implanted with an orthopedic device configured to permit interbody fusion across the target disc space. After the disc is implanted with the orthopedic device, corridor C is used to access the lateral aspect of the ipsilateral facet joint of the target functional spinal unit and a bone fastener is placed across the facet joint in a lateral to medial trajectory. Advantageously, the implantation of the target intervertebral disc space may be performed before or after access of the ipsilateral facet joint; e.g., prior to facet immobilization with the fastener.

In additional embodiments, several other methods for vertebral fixation are disclosed wherein corridor C is used to access the anterior aspect of the ipsilateral transverse process and the lateral ipsilateral pedicle to which it is attached.

Further, various bone screw trajectories are disclosed for use in the disclosed methods of vertebral fixation.

Furthermore, methods for placement of bone screws into the ipsi- or contra-lateral pedicles from lateral or anterolateral screw insertion site (into the vertebral body) are described.

Detailed Description of the Exemplary Embodiments

Described herein are devices, systems and methods for the treatment of abnormal spinal stability and stenosis of the spinal canal. In an exemplary embodiment of the invention, the spine is approached through a lateral (i.e., side) corridor or an anterolateral corridor, and both the anterior and posterior columns of the spine are manipulated, implanted and/or otherwise surgically treated through the same intra-abdominal surgical corridor. Any of these surgical corridors, while intra-abdominal, may also be extra-peritoneal (i.e., corridors with do not traverse the peritoneal cavity).

FIGS. 1A-1C show diagrammatic representations of a spinal vertebral bone 802 in multiple views. For clarity of illustration, the vertebral bone of FIGS. 1A-1C and those of other illustrations disclosed herein are represented schematically and it should be appreciated that actual vertebral bodies may include anatomical details that are not shown in these figures. Specifically, actual vertebral bodies may vary in anatomy from the idealized vertebral bones illustrated in the drawings, whether because of congenital or acquired deformity, spondylotic change (such as bony spurs and the like), spinal malalignment and/or other changes. For descriptive purposes, idealized vertebral bones are assumed.

The term "sagittal plane", as used herein, refers to the plane that splits the body into left and right segments. The "mid-sagittal plane" or "median plane" splits the body into equal left and right halves. The term "coronal plane", as used herein, is the plane that divides the body into anterior (front) and posterior (back) segments. Hence, the coronal and sagittal planes are perpendicular to one another.

Further, it will be understood that the vertebral bones at a given level (i.e., in a given spinal section) of the spinal column of a human or animal subject will contain anatomical features that may not be present at other levels of the same spinal column. The illustrated vertebral bones are intended to generically represent vertebral bones at any spinal level without limitation. The disclosed devices and methods may be employed at any applicable spinal level.

Vertebral bone 802 contains an anteriorly-placed vertebral body 804, a centrally placed spinal canal 806 and posteriorly-placed lamina 808. The pedicle segments 810 of vertebral bone 802 form the lateral aspects of the spinal canal 806 and connect the laminas 808 to the vertebral body 804. The spinal canal 806 contains neural structures such as the spinal cord and/or nerves. A midline protrusion termed the spinous process SP extends posteriorly from the medial aspect of laminas 808. A protrusion extends laterally from each side of the posterior aspect of the vertebral bone 802 and is termed the transverse process TP.

A right transverse process RTP extends to the right from the lateral aspect of the right pedicle. A left transverse process LTP extends to the left from the lateral aspect of the left pedicle. A superior protrusion extends superiorly above the lamina 808 on each side of the vertebral midline and is termed the superior articulating process SAP. An inferior protrusion extends inferiorly below the lamina 808 on each side of the vertebral midline and is termed the inferior articulating process IAP. Note that the posterior aspect of the pedicle 810 can be accessed at an indentation 811 in the vertebral bone 802 between the lateral aspect of the SAP and the medial aspect of the transverse process TP. In surgery, it can be common practice to anchor a bone fastener into the pedicle portion 810 of a vertebral bone 802 by inserting the fastener through indentation 811 and into the underlying pedicle 810 in a posterior to anterior direction.

FIGS. 2A and 2B illustrate a functional spinal unit (FSU), which includes two adjacent vertebrae and the intervertebral disc disposed between the adjacent vertebrae. The intervertebral disc resides between the inferior surface of the upper vertebral body and the superior surface of the lower vertebral body, although it is not specifically shown in the figures. FIG. 2A shows the posterior surface of the adjacent vertebrae and the articulations between them. FIG. 2B shows an alternate oblique view of the identical structure. The FSU contains three joints between the two vertebral bones, with the intervertebral disc comprising the anterior joint. The posterior joints include a facet joint 814 on each side of the midline, wherein each facet joint 814 is comprised of the articulation between the inferior articulating process (IAP) of the superior vertebral bone and the superior articulating process (SAP) of the inferior bone. These and other illustrations and definitions of anatomical structures are known to those of ordinary skill in the art. They are described in more detail in Atlas of Human Anatomy, by Frank Netter, third edition, *Icon Learning Systems*, Teterboro, N.J., which is hereby incorporated by reference in its entirety. It will be appreciated that the directional language and terms regarding orientation (such as "upper", "lower", "upward", "downward", etc.) are used throughout merely for convenience of description and are not intended to be limiting.

At the spinal segment to be surgically treated via the disclosed methods, a coronal plane T (which is a vertical plane of the subject's body) may be defined to contain the most anterior point of each of the right and left transverse processes. In general, the most anterior segment of each transverse process is found at its medial border with the lateral anterior border of the pedicle to which it is attached. Coronal plane T is illustrated in FIGS. 1B and 3. Further, a coronal plane U (FIG. 1B) may be defined as the plane of the posterior wall of the vertebral body when considered at the level of the superior cortical surface of said vertebral body. In this way, the foregoing coronal planes may be used to define an anterior vertebral segment and a posterior vertebral segment.

Some medical literature uses coronal plane U as a dividing line between the anterior and posterior vertebral segments (such as, e.g., in the two column model of the spine). (See, e.g., "The three column spine and its significance in the classification of acute thoracolumbar spinal injuries." By Denis F. *Spine* 1983 November-December; 8(8):817-31, which is herein incorporated by reference in its entirety.) While either coronal plane U or coronal plane T can be used to define the boundary between the anterior and posterior segment of the vertebral bone, for the purposes of the present disclosure, coronal plane T is employed as an exemplary boundary plane, however coronal plane U can be additionally or alternatively employed.

A subject requiring surgery on a segment of their lumbar spine may be positioned on the operating table in the supine, prone, lateral decubitus or a combination of these positions. For example, a patient may be positioned between supine (i.e., his back at zero degrees relative to the OR table) and lateral positions (i.e., his back at ninety degrees to the OR table) with one side of the pelvis positioned further above the OR table than the other pelvic side. In one example, the subject is positioned in the lateral decubitus position as show in FIG. 3. In this example, the patient is positioned with the left lateral side up (i.e., away from the operating table) and the mid-sagittal plane of the spine parallel to the floor. The lumbar segment to be surgically treated is comprised of at least a superior vertebral bone, an immediately inferior vertebral bone and the intervening intervertebral disc space. The FSU to be surgically treated will be referred to as the "target FSU" and its intervertebral disc space as the "target intervertebral disc space".

An exemplary method of device implantation is now illustrated. First, a target FSU is identified for surgical manipulation and treatment. In preparation for surgery, the patient may be placed in the above described lateral decubitus position (FIG. 3). The level of the spine that is to be implanted can be localized on an imaging modality (such as X-ray, CT, Mill and the like) in at least one plane. After customary sterilization and/or other preparation of the operative site, the surgeon can localize an incision point on the skin that is anterior to coronal plane T. In one implementation, the incision may be made immediately anterior to a coronal plane that is parallel to coronal plane T and passes through the anterior-most (tip) aspect of the target disc space. In other words, an incision is made in a segment of the skin of the subject that is anterior to coronal plane T but lateral to mid-sagittal plane that divides the body into right and left sides.

Figure 4:
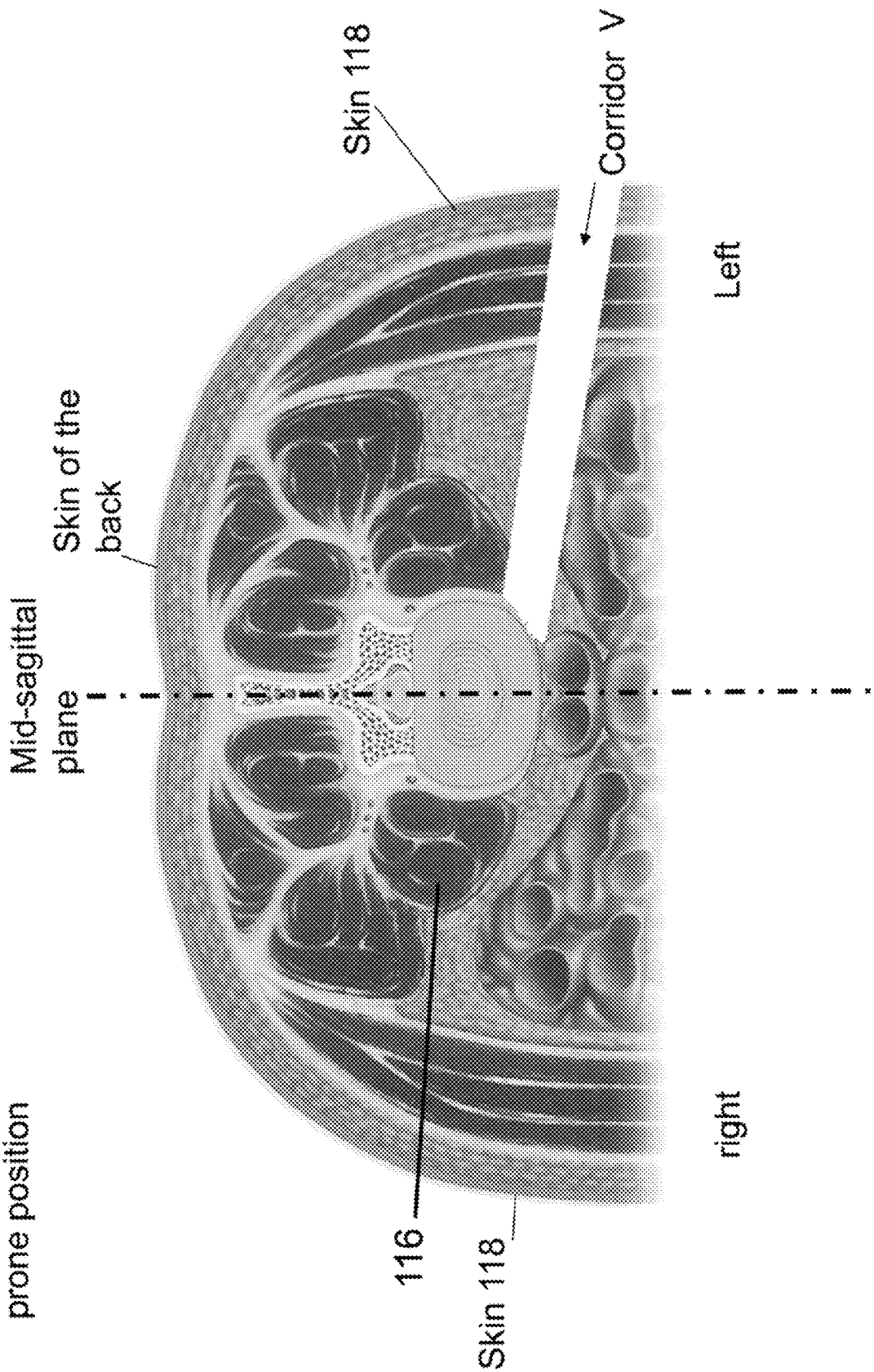
FIG. 4 is a schematic representation of a human torso in cross-section.

A surgical corridor is developed through the extra-spinal tissue from the incision until the target FSU is reached, wherein the corridor to the target disc space is at least partially anterior coronal plane T. In one embodiment, the target intervertebral disc space is entered and at least a portion of the viscoelastic material that comprises the natural nucleus pulposus is removed. For example, in the lumbar vertebra depicted in FIG. 5, the disc space may entered in at least one or more of the three following locations: a) medial to the aorta and may comprise the midline (and/or its branches, the common iliac arteries, etc.) to form a direct anterior approach 505; b) lateral to the aorta but anterior to the ipsilateral psoas major muscle to form an anterolateral approach 507, in which the ipsilateral psoas major muscle is ipsilateral to the skin incision used to develop the surgical corridor; and c) laterally and through the body of the ipsilateral psoas major muscle to form a direct lateral approach 509. In another example, a lateral corridor "V" (shown in FIG. 4) can be made from the flank incision and taken onto the target intervertebral disc space.

The disc space may be entered using at least one or more of the example corridors shown in FIG. 5. In one implementation, the target intervertebral disc space is entered using an anterolateral approach (such as, e.g., anterolateral approach 507 shown in FIG. 5), which is at least partially positioned between the lateral aorta and the anterior surface of the ipsilateral psoas major muscle.

If desired, after removal of viscoelastic material, an orthopedic implant may be implanted into the target intervertebral disc space using the same surgical corridor and then left in place after surgery is complete. In this specific example, after removal of at least a portion of the nucleus pulposus of the target intervertebral disc space, an implant 206 may be placed into the disc space (FIG. 10A). In an exemplary embodiment, implant 206 extends across the mid sagittal plane of the disc space and has one end segment positioned onto the left side of the apophyseal ring of the inferior vertebral bone and a second end segment positioned on the right side of said apophyseal ring. The operation, when performed using a trans-psoas corridor 509, is known to those skilled in the art as the "XLIF" procedure, among other names. (See "Extreme Lateral Interbody Fusion (XLIF): a novel surgical technique for anterior lumbar interbody fusion." By Ozgur, Aryan et al. in *Spine J.* 2006 July-August; 6(4):435-43, which is herein incorporated by reference in its entirety.)

Additionally, the superior and inferior vertebral bones may be distracted away from one another in order to increase the vertical height of the target intervertebral disc space. The optional distraction step may be performed with distraction instrument(s) that are transiently used during surgery and then removed prior to the end of the procedure, and/or by the orthopedic implant(s) that is positioned during surgery and left in place. Whether the target intervertebral disc space is entered and manipulated or not, at least a portion of the surgical corridor may be oriented so as to extend through the anterior layer of the thoracolumbar fascia. (A full description of the anatomy of the thoracolumbar fascia is contained in: *The thoracolumbar fascia: anatomy, function and clinical considerations.* Willard F H, et al. *J Anat.* 2012 December; 221(6): 507-536, which is herein incorporated by reference in its entirety.)

Figure 6:
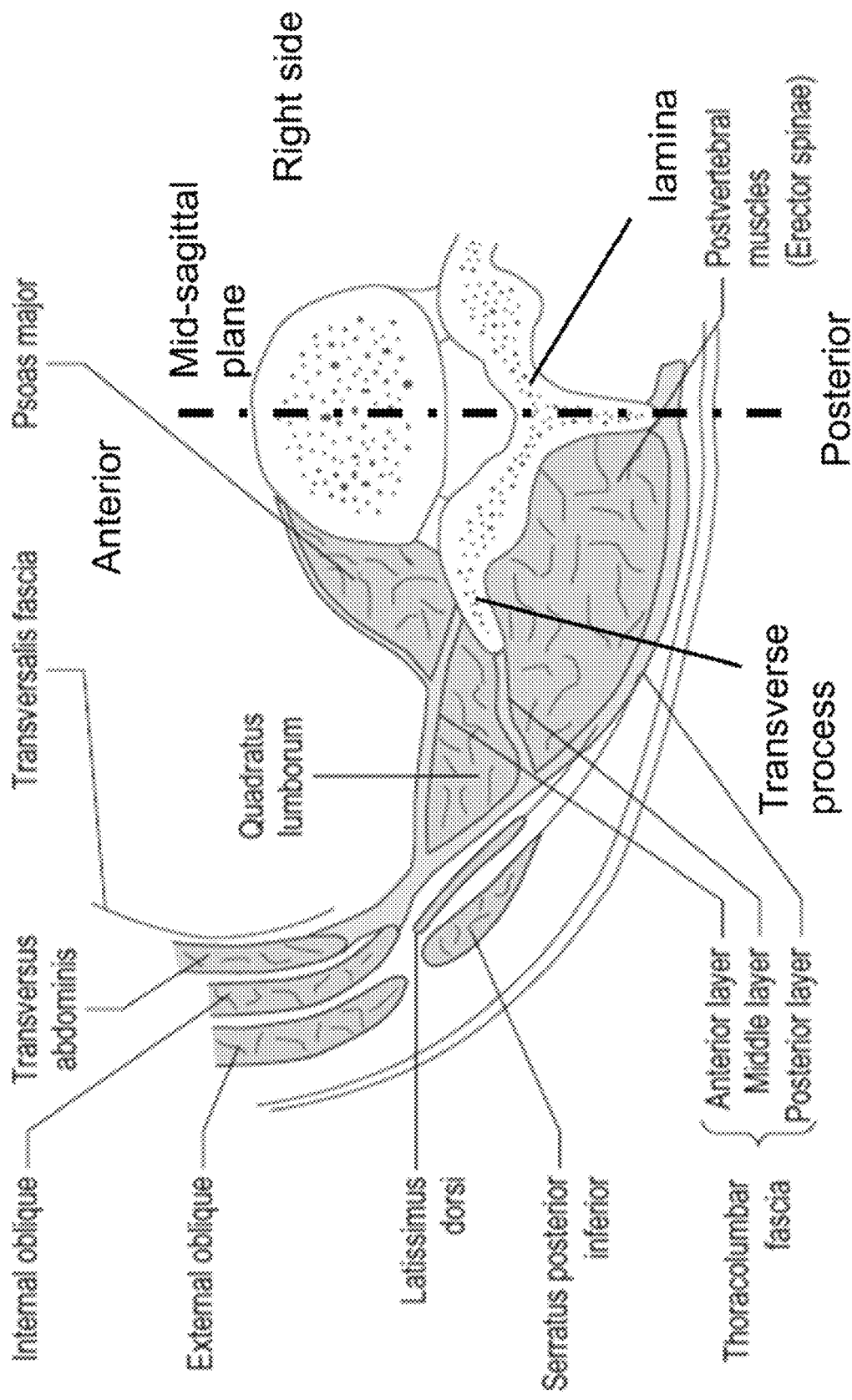
FIG. 6 is a cross-sectional view of a subject's spine and surrounding anatomy.
Figure 7:
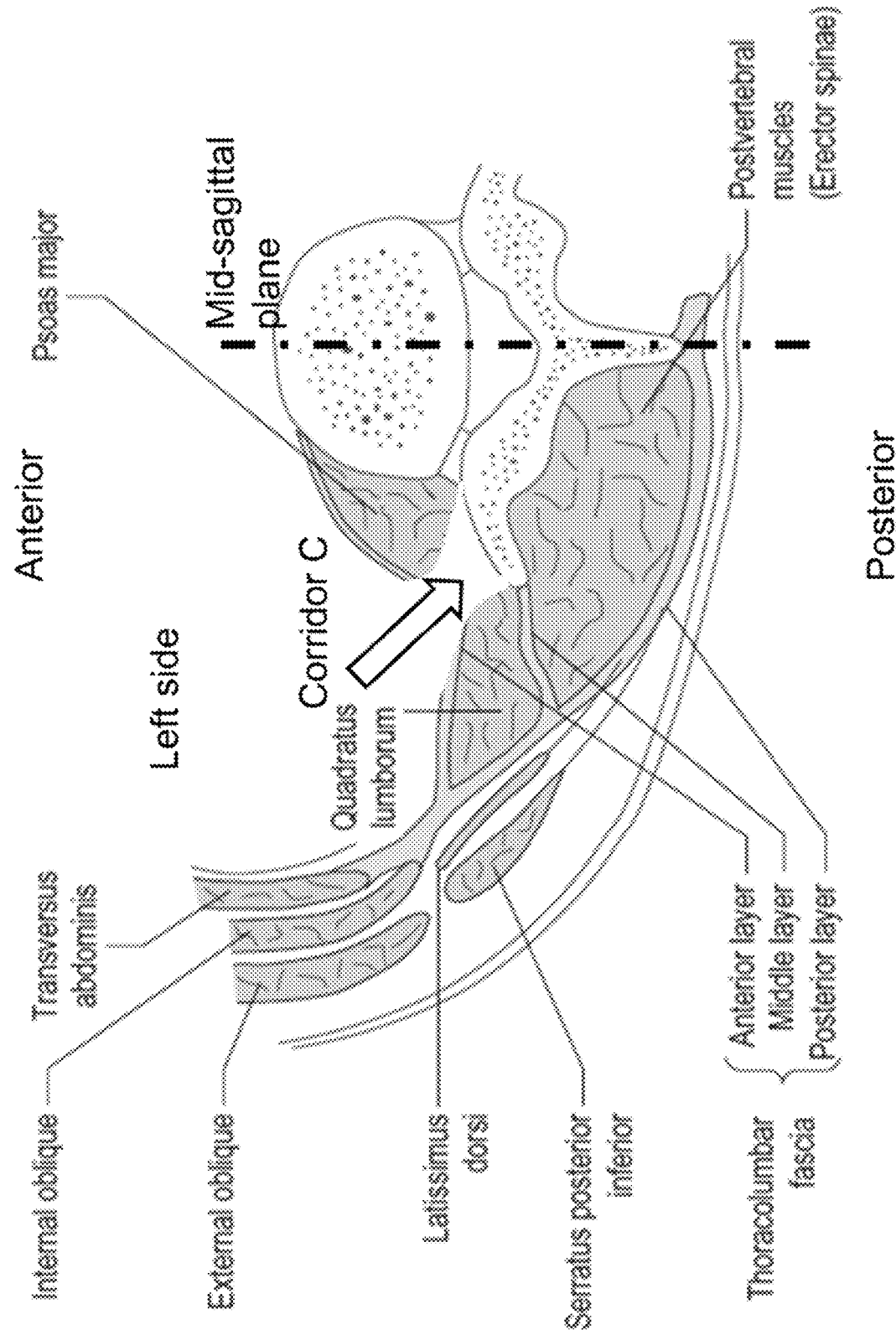
FIG. 7 is a cross-sectional view of a subject's spine and surrounding anatomy illustrating approach Corridor C.

In another implementation, development of a surgical corridor C is illustrated in FIGS. 6 and 7. As shown, corridor C is developed between the posterior aspect of the ipsilateral psoas major and the anterior and medial aspect of the ipsilateral quadratus lumborum muscle. While corridor C is intended to substantially extend between these two muscles, it may contain at least a segment of each of them. Corridor C is thereby intended to be anterior to the anterior surface of the ipsilateral transverse process of the inferior vertebral bone of the target FSU and posterior to at least the posterior half of the ipsilateral psoas major muscle (when the latter is taken in a sagittal plane that traverses it).

In the superior lumbar spine, the psoas is usually a small muscle and it increases in size as it extends inferiorly. In some segments of the spine, such as the thoracic spine, the psoas major muscle is not present at all. Where the muscle is absent, it is understood that corridor C is defined by its relationship to the ipsilateral transverse process and not by its relationship to the psoas muscle. In some examples, the anterior layer of the thoracolumbar fascia is traversed by corridor C. Dissection may be continued through corridor C in order to traverse coronal plane T in an anterior to posterior direction. In this way, the ipsilateral transverse processes of the vertebral bones of the target FSU may be reached. Similarly, segments of the target functional spinal unit that are positioned posterior to coronal plane T may be accessed through corridor C.

If desired, the ipsilateral transverse process of either said superior or inferior vertebral bone of the target functional spinal unit may be removed through corridor C (FIGS. 8A and 8B). The harvested transverse process bone may be used as autograft bone for a fusion procedure that is concurrently performed at the same operation. In other words, the preceding steps constitute a method for removal of a transverse process of the target FSU. In this exemplary method, an intra-abdominal (and, in some examples, extra-peritoneal) surgical corridor is developed through a plane between the ipsilateral psoas major muscle and at least a segment of the ipsilateral quadratus lumborum muscle. Subsequently, the ipsilateral transverse process of one or both vertebral bones of the target functional spinal unit is removed.

The removed transverse process may be used as a bone graft (i.e., autograft) material to fuse two or more skeletal bones of the individual during the same surgical procedure (if desired). In one embodiment, the harvested transverse process bone is incorporated into the bone graft that is used to fuse the superior vertebral bone to the inferior vertebral bone of said target functional spinal unit. For example, at least a portion of the bone graft that is used to fuse superior to inferior vertebral bones (by positioning a segment of the bone graft to abut the superior vertebrate bone and a segment to abut the inferior vertebral bone) is comprised of bone derived from the harvested transverse process.

At least a portion of the harvested transverse process bone may be placed into the target intervertebral disc space in order to form an interbody fusion within the target functional spinal unit. Further, bone graft material (whether containing autograft bone, allograft bone, a synthetic material, or any other substance adapted to form bone) may be placed to extend along the longitudinal axis of the spine from the lateral aspect of the superior articular process (SAP) of the superior vertebral bone to the superior articular process (SAP) of the inferior vertebral bones of the target functional spinal unit. The bone graft material will eventually form a fusion mass that connects the SAP and transverse processes (or the remaining stump thereof) of adjacent vertebral bones (FIG. 8B).

Figure 9:
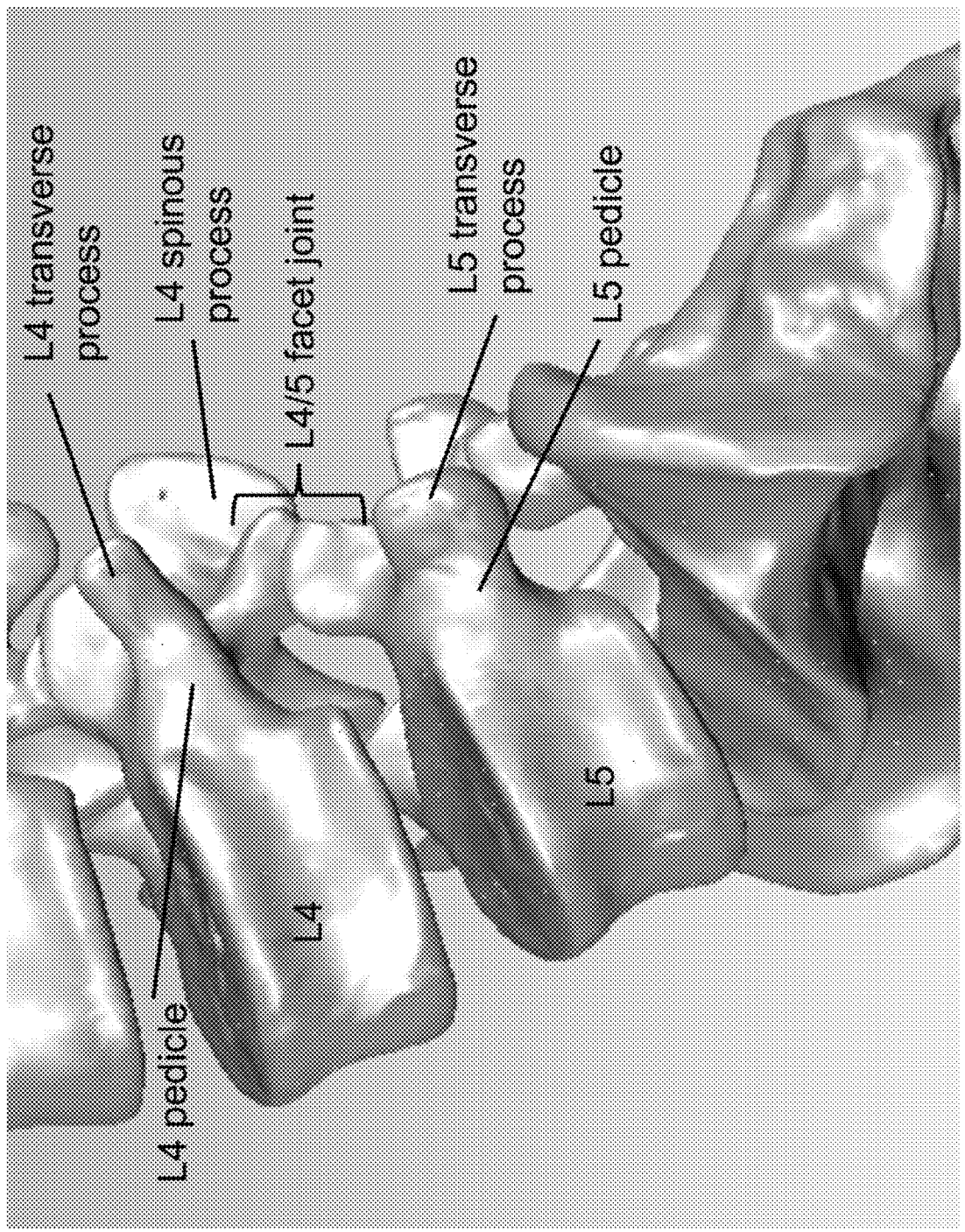
FIG. 9 is an anterior perspective view of a target FSU.

As depicted in FIG. 9, a facet joint, by definition, is an articulation comprised of the superior articulating process (SAP) of an inferior vertebral bone and the inferior articulating process (IAP) of the immediately superior vertebral bone. In the target FSU, right and left facet joints form articulations between the superior and inferior vertebral bone with a single facet joint on each side of the mid sagittal plane of the vertebral column. Using corridor C to reach the ipsilateral transverse process, as described above, the ipsilateral facet joint (ipsilateral to the skin incision) can be also accessed.

In one embodiment, the ipsilateral transverse process of the inferior vertebral bone of the target FSU is removed in order to provide a wider corridor through which to access the ipsilateral facet joint. However, it will be understood that the transverse process may be left in place or only partially removed and the ipsilateral facet joint accessed around the transverse process. When the transverse process is not fully removed, the facet joint may be accessed through an anterior to posterior trajectory that passes superior to said ipsilateral transverse process of the inferior vertebral bone, as shown in FIGS. 10 A and 10B. The trajectory used to access the ipsilateral facet joint via corridor C will necessarily cross coronal plane T in an anterior to posterior trajectory (FIG. 10B) and will substantially follow member 200. Note that the tip of member 200 is positioned at the lateral surface of the SAP of the inferior vertebral one of the target FSU.

The preceding steps constitute a method to access the ipsilateral facet joint between the superior and inferior vertebral bones of a target FSU. Once accessed, the ipsilateral facet joint may be least partially removed, if desired, to decompress the nerve elements. The joint, whether whole or after partial resection, may be also implanted with fastener(s) that serve to limit and/or completely immobilize movement between the superior and inferior vertebral bones, as will be further discussed below.

After the ipsilateral facet is accessed through corridor C, one or more fixation devices (such as, e.g., a bone screw and/or the like) may be used to limit movement and/or immobilize the facet joint. For example, FIG. 10A shows an illustrated spine with implant 206 positioned within the L4/L5 disc space. As described above, the implant 206 may be placed into the target disc space via the antero-lateral corridor 507. In some examples, the anterior column implant is placed first and then the surgical corridor is turned posteriorly in order to access the ipsilateral facet joint through the corridor anterior to the ipsilateral quadratus lumborum (corridor C).

In regions of the spine where the psoas muscle is large (such as L3 to L5), corridor C may be posterior to the psoas muscle. While the anterior implant 206 is, in some examples, implanted prior to facet joint access, either the disc space work or the facet joint access may be performed first. (Many embodiments of interbody implants are known in the art. U.S. Pat. Nos. 4,636,217; 5,015,247; 5,192,327; 5,443514; 5,749,916; 6,251,140; 6,342,074; 6,706,070; 6,767,367; 6,770,096; 6,852,127; 7,037,339; 7,227,477; 7,641,690, among others, disclose some of these inter-body implant device. Each of the foregoing listed patents is herein incorporated by reference in its entirety.)

As previously noted, the ipsilateral transverse process of the inferior vertebral bone of the target FSU may be removed to permit greater access to the ipsilateral facet joint. If removed, the harvested bone can be used as autograft within the fusion bone mass used to fuse the superior and inferior vertebral bones of the target FSU. The harvested bone may be also placed into the intervertebral disc space to produce an interbody fusion.) If the transverse process is not completely removed, then the ipsilateral facet joint may be reached using the trajectory of member 200. That trajectory extends across coronal plane T in a lateral to medial and anterior to posterior direction. The trajectory may be superior to the ipsilateral transverse process, as shown in FIG. 10B.

A bone fastener can be passed sequentially via a lateral to medial trajectory through the superior articulating process (SAP) of the inferior vertebral bone, across the joint space and then into the inferior articulating process (IAP) of the immediately superior vertebral bone. The fastener may be further passed from a lateral to medial trajectory into the ipsilateral lamina of the superior vertebral bone as well be illustrated further below. The fastener is at least partially inserted through corridor C and follows an anterior to posterior trajectory across coronal plane T.

Figures 11A, 11B:
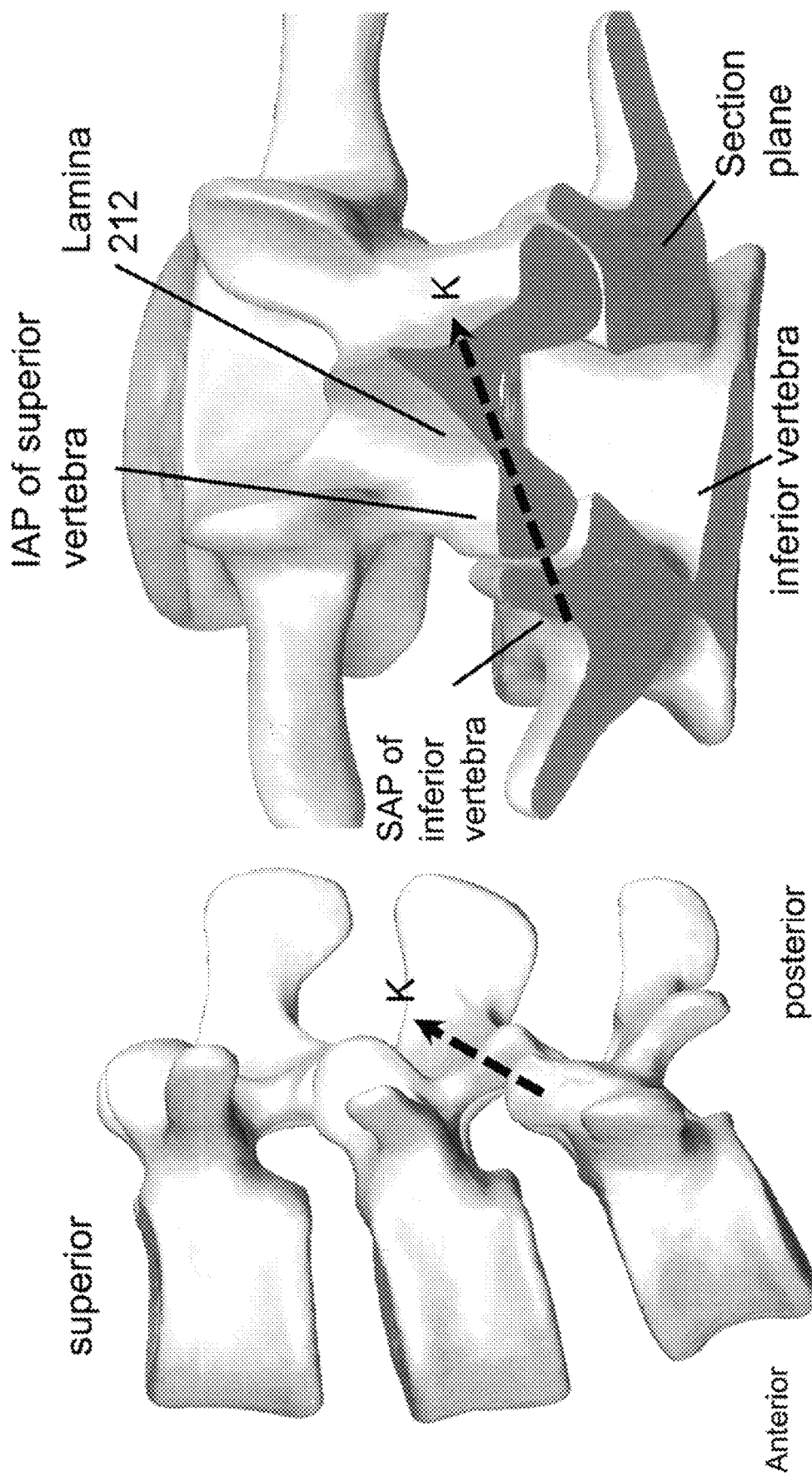
FIGS. 11A and 11B are side elevation and posterior perspective views of a subject's spine, respectively, illustrating a trajectory of a bone screw used to fixate the facet joint.

Specifically, a fastener may be placed into the ipsilateral facet joint in order to immobilize the movement between the superior and inferior vertebral bones across said joint. Following a lateral to medial trajectory (such as, e.g., the trajectory of member 200), the fastener may be passed through the lateral aspect of the SAP of the inferior vertebral bone, across the facet joint space and into the IAP of the superior vertebral bone, as indicated by arrow K in FIGS. 11A and 11B. Note that the fastener may be further passed into the ipsilateral lamina 212 of the superior vertebra as shown in FIG. 11B. FIG. 11B illustrates a sectional view passing through the facet joints between the L3 and L4 vertebral bones. The plane of the sectional view is shown by the anterior-posterior direction of arrow K in FIG. 11A. The lateral-medial direction of arrow is shown in FIG. 11B.

Fasteners of any applicable design may be used. For example, FIGS. 12A and 12 B illustrate a faster 240 comprising a bone screw 244 and a washer-like member 246. In one example, the head of screw may move inside member 246 in at least one plane (such as, e.g., in a ball-in-socket like design) so that shank 2442 may be positioned in one of a plurality of different positions/angles relative to the central axis of the bore 2462 of member 246. While not illustrated, fastener 240 may further comprises a locking feature that permits movement between screw 244 and member 246 in a first configuration, and immobilizes screw 244 relative to member 246 in a second configuration.

Many such locking features are known in the art and include among others, for example, a set screw that threadably engages member 246. The set screw may be tightened into a second configuration to immobilize screw 244 relative to member 246, or may be left untightened in a first configuration, to permit movement between screw 244 and member 246. In use, screw 244 is passed into the ipsilateral facet joint (for example, using the trajectory of arrow K) until member 246 is forcibly positioned against the lateral, outer surface of the SAP of the inferior vertebra. The locking feature may be then transitioned from the first configuration to the second configuration in order to immobilize screw 244 relative to member 246.

Figure 14:
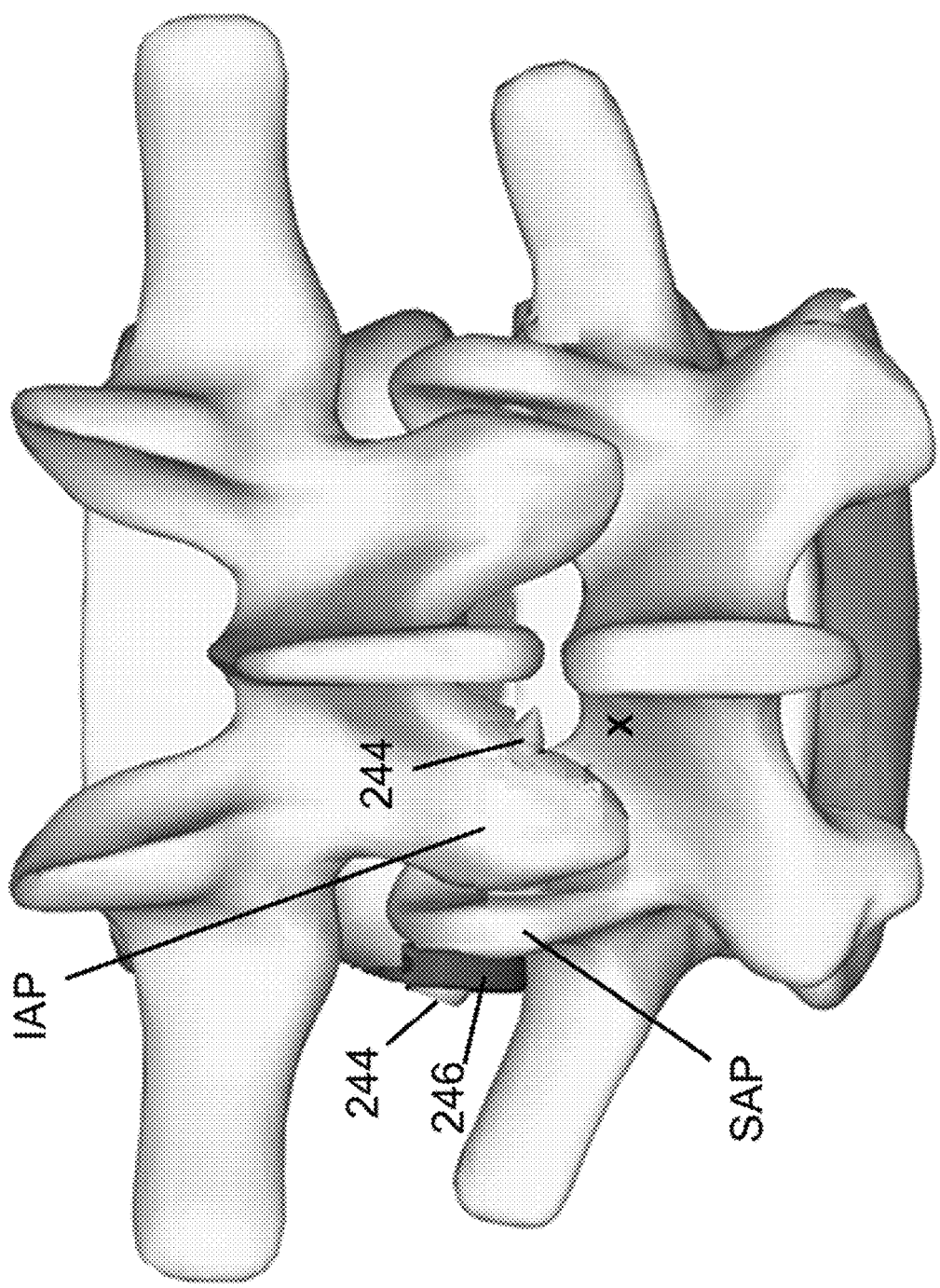

FIGS. 13A and 13B illustrate implant 206 within the intervertebral disc space of the target FSU and fastener 240 immobilizing the ipsilateral facet. Note that the ipsilateral transverse process is intact in FIG. 13A and removed in FIG. 13B. While the distal aspect of screw 244 is illustrated passing into the ipsilateral lamina of the superior vertebral bone, it may alternatively be placed in a trajectory that traverses the TAP of the superior vertebra bone without extending further into the ipsilateral lamina of the superior bone. This trajectory is shown in FIG. 14. Further, screw 244 may be angled even more inferiorly so that its distal aspect enters the lamina and/or spinous process of the inferior vertebral bone after traversing the facet joint. The entry point may be, for example, at or near point "X" of FIG. 14.

FIG. 15 shows perspective views of bone fastener assembly 105, while FIG. 16 shows a cross-sectional view of fastener assembly 105. Exemplary bone fastener assembly 105 includes a threaded bone screw 107 with threaded shaft 1072 and a spherical head 1074. An internal bore 1076 extends through the internal aspect of the screw 107, extending from the top of head 1074 to the tip of shaft 1072. The internal bore has a threaded portion 1078. A hex-shaped receptacle 1079 resides within head 1074. Receptacle 1079 is adapted to accept a screw driver (such as with a hex-shaped tip, or the like), wherein the driver can deliver a rotational force to screw 107 and drive the threaded shaft into bone.

An outer housing 110 has an internal seat 1102 that is adapted to seat head 1074 of screw 107. Housing 110 has an additional seat 1104 that is adapted to accept an interconnecting member, such as a rod. Threads 1106 are adapted to compliment and accept threaded locking nut 116. A pusher member 114 is disposed between the two seat portions 1104 and 1102 of housing 110 and transmits the downward force of the locking nut 116 onto head 1074 (when an interconnecting rod is positioned between the locking nut and pusher member 114).

An interconnecting member, such as a rod, may be positioned within seat 1104 of housing 110. Specifically, the housing 110 and screw 107 are moved into the desired relative spatial orientation. Locking nut 116 is positioned above the seated interconnecting member and then threadably advanced relative to threads 1106 of housing 110. As locking nut 116 is advanced, the interconnecting rod member is forced onto pusher member 114. The pusher 114 is then forced downward onto head 1074 of screw 1074, trapping the head between the pusher 116 and seat 1102. In this way, full advancement of locking nut 116 produces rigid immobilization of the interconnecting member, the housing 110 and the screw 107 relative to one another.

It will be appreciated that screw assembly 105 is intended to be illustrative and non-limiting. Further, it will be understood that other bone screw assemblies may be alternatively used and that multiple such screw assemblies are known in the art. For example, U.S. Pat. Nos. RE37665, 6,248,105; 6,371,957; 6,565,565; 6,641,586; and 7,704,271 each disclose at least one bone screw assembly that may be used to accomplish the present method. Each of the foregoing U.S. Patents is herein incorporated by reference in its entirety. Any of these or any other applicable bone screw assemblies that are adapted to for use in interconnecting neighboring bones may be alternatively or additionally used.

FIG. 17 illustrates a method through which one or more bone fastener assemblies 105 may be used to fixate a target spinal segment comprising one or more FSUs. The fastener (s) may be passed through corridor C onto the lateral aspect of the SAP of the inferior vertebral bone within each FSU. Threaded shaft 1072 may be passed through the ipsilateral facet joint and into the ipsilateral lamina of the superior vertebral bone via, for example, trajectory K of FIG. 11. Alternatively, one or more of fasteners assemblies 105 may be inserted into the vertebral bones wherein at least one fastener is anchored onto at least a portion of the pars interarticulais (either its true lateral surface, indicated as "B" in FIG. 17, or via a more posterior entry point and/or into the ipsilateral lamina) without traversing the ipsilateral facet joint. Alternatively, in another embodiment, one or more fastener assemblies 105 may be passed posterior to the pars interarticulatis and into the spinous process of the vertebral bone. Regardless of which of the aforementioned trajectories is employed, once inserted into vertebral bone, the fastener assemblies 105, disposed at different levels, may be interconnected to each other via an interconnecting rod. While bone assemblies 105 are illustrated, it will be understood that other bone screws and/or fastener assemblies may be additionally or alternatively used to fixate into the vertebral bones via the disclosed method and trajectory, and then interconnected with other fasteners/bone screws disposed at other levels. The interconnection may be performed by interconnecting rods and/or interconnecting plates.

Note that the term "bone screw" is used as a generic term and may include, but is not limited to, fastener assembly 105 or any other appropriate bone screw/assembly that may be adapted to couple with an interconnecting rod and/or plate. For example, the bone screw 107 of bone fastener assembly 105 may serve, by itself, as a bone fastener for use in any of the disclosed methods, since, at a minimum, it may be coupled with an interconnecting bone plate. Thus, the terms "bone screw" and "bone fastener assembly" user herein may be used interchangeably and imply that screw/fastener assembly may be coupled to an interconnecting member, such as a plate or a rod. Bone screws may be also used as freestanding, uncoupled fasteners that are driven across more than one bone in order to fixate these bones to one another.

Figure 18A:
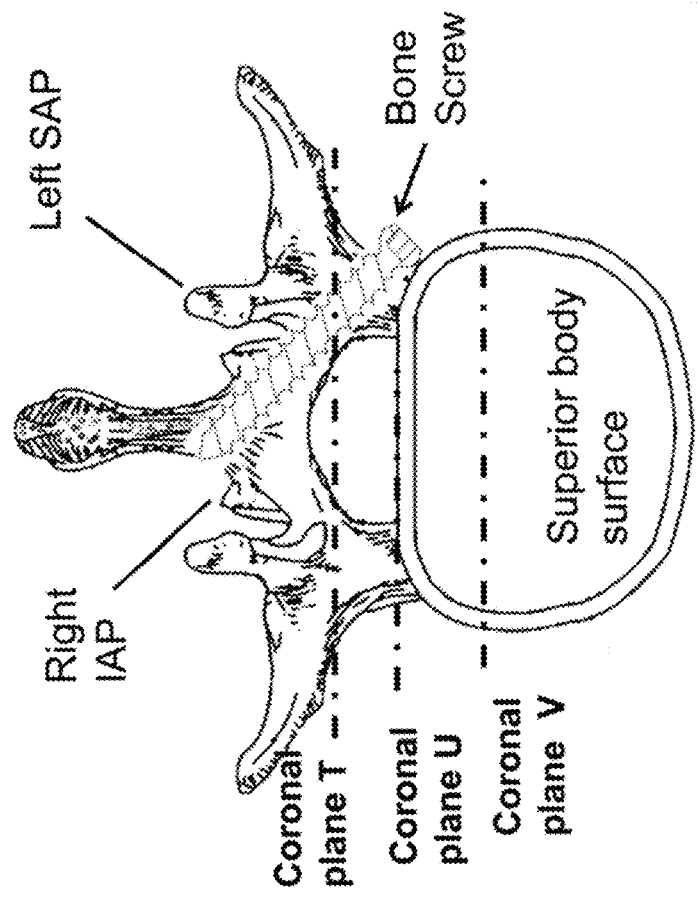
FIGS. 18A and 18B are a top plan view and side perspective views of a subject's spine illustrating a position and a trajectory of a bone screw/fastener assembly.
Figure 18B:
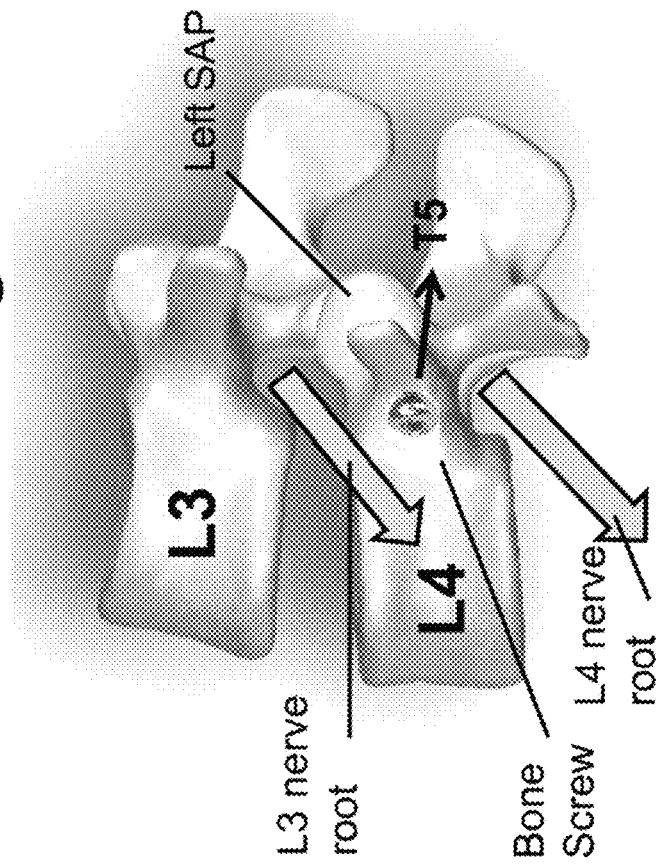

FIGS. 18A and 18B illustrate an additional exemplary method through which bone screw(s)/fastener assemblies may be used to fixate a target spinal segment comprising one or more FSUs. The bone screw(s)/fastener assemblies may be passed through corridor C onto the lateral aspect of the ipsilateral pedicle and traverse, at least partially, a portion of the pedicle. In one example, the bone screw fastener assembly extends through the pedicle in both a lateral to medial and anterior to posterior trajectory, as shown in FIG. 18A. The distal segment of the bone screw/fastener assembly may be further advanced into the lamina and/or spinous of the vertebral bone containing the pedicle into which the screw is inserted (FIG. 18A). While the bone screw/fastener assembly appears to be positioned on top (i.e., the superior aspect) of the left pedicle, it is understood that this depiction is for illustrative purposes only and the actual path extends through the substance of the pedicle and vertebral bone. In FIG. 18A, the bone screw/fastener assembly appears similar to screw 107 of assembly 105 (FIGS. 16 and 17) for illustrative simplicity. However, as stated above, any bone screw/fastener assembly may be additionally or alternatively used.

In an exemplary embodiment, as shown in FIG. 18A, the bone screw entry point is preferably posterior to coronal plane V and anterior to coronal plane T. Coronal plane U was previously defined and coronal plane V may be defined as parallel to and 15 mm anterior to coronal plane U. As stated elsewhere herein, it will be understood that the vertebral bodies may vary in actual anatomy from the idealized vertebral bones illustrated herein, whether from congenital or acquired deformity, spondylotic change (such as bony spurs and the like), spinal malalignment or other changes, and for descriptive purposes an idealized vertebral bones are assumed.

FIG. 18B illustrates a lateral view of an FSU with the bone screw of FIG. 18A inserted into the lateral aspect of the L4 pedicle. As noted above, the bone screw may take an anterior to posterior and lateral to medial trajectory within the substance of the bone. An exemplary axial trajectory of the bone screw, trajectory T5, is shown in FIG. 18B. Note that lateral surface of the pedicle provides an access window between the nerve root above (L3 nerve root) and the nerve below (L4 nerve root). As segment of the lateral aspect of the pedicle is devoid of nerves, as well be discussed further below, this segment may be used as the entry point for the bone screw.

FIG. 19A illustrates a view of a lateral aspect of an FSU, while FIG. 19B shows a coronal section taken along plane M. Note that the pedicles of adjacent vertebrae are vertically aligned while the nerves exit at an angle between the adjacent pedicles. For example, the left L3 pedicle is vertically positioned above the left L4 pedicle and the left L3 nerve root exits the spinal canal in an oblique trajectory that extends from superior/medial to inferior/lateral. This provides two segments, segments K1 and K2, through which one may traverse a horizontal plane of the FSU without encountering the nerves. Segment K1 is known to those of ordinary skill in the art as "Kambin's triangle". (See *Cadaveric Analysis of the Kambin's Triangle*. By Hoshide R, Feldman E, et al. Cureus. 2016 Feb. 2; 8(2), which is herein incorporated by reference in its entirety.)

Segment K2 is previously undescribed and may be an additional or alternate location for bone screw insertion into a vertebral bone. For example, the lateral aspect of the pedicle of the vertebral bone to be instrumented can be approached through corridor C. A bone screw may be inserted into the lateral aspect of the pedicle and/or proximal vertebral body through segment K2, using a bone entry point that is anterior to coronal plane T and/or posterior to coronal plane V (FIG. 18A). The subsequent trajectory of the bone screw within the vertebral bone may be, for example, the trajectory shown in FIGS. 18A and 18B.

A known pathway for bone screw insertion within the posterior aspect of the vertebral bone is the "cortical bone screw trajectory" and is described in, among other citations, Cortical bone trajectory for lumbar pedicle screws, Santoni B G, Hynes R A, et al. *Spine J.* 2009 May; 9(5):366-73, which is herein incorporated by reference in its entirety. In the cortical bone screw trajectory, the bone screw is inserted into the posterior surface of the vertebral bone, often immediately medial to the vertebral bone's superior facet joint (i.e., the facet joint formed by that vertebral bone's SAP and the IAP of the immediately superior vertebral bone). The bone screw is guided in a medial to lateral trajectory as it is advanced anteriorly into the vertebral bone (for example, as depicted in FIG. 23B).

In one implementation of the current invention, a bone screw is inserted into a lateral surface of vertebral bone such as, e.g., into segment K2. The bone entry point for screw insertion may be between coronal plane T and coronal plane V in the anterior to posterior direction and between the superior bony surface of the vertebral body being instrumented and the horizontal plane of the most inferior point of the ipsilateral pedicle. The screw trajectory in the vertebral bone is substantially 180 degree to that of the known cortical bone screw trajectory that is described above. In other words, the bone screw of this method is guided in a lateral to medial trajectory as it is advanced posteriorly into the vertebral bone from the bone insertion point, having a trajectory similar to that depicted in FIG. 18A.

In an additional implementation, one or more bone screws may be attached anteriorly, directly onto the body of the vertebral bone. For example, the vertebral body may be accessed using the direct anterior approach 505, the antero-lateral approach 507 and/or the direct lateral approach 509 of FIG. 5. Any other known approach to access the antero-lateral surfaces of the vertebral body though a skin incision made anterior to coronal plane T may be additionally or alternatively used. At least one bone screw is advanced into the vertebral body and then directed posteriorly in order to have the distal aspect of the screw exit the vertebral body at least partially through the vertebral body-pedicle junction and enter the anterior aspect of the contralateral pedicle. (The body-pedicle junction is a vertical segment of bone wherein the anterior end of the pedicle joins the posterior vertical surface of the vertebral body.)

The foregoing method of bone screw placement is illustrated in FIG. 20A, wherein the screw trajectory is selected so that the distal aspect of the bone screw may, at least partially, traverse the contralateral pedicle, in a medial to lateral direction, and may, but not necessarily, exit the lateral wall of the pedicle at, for example, segment K2 (FIG. 19B). Specifically, FIG. 20A illustrates the screw trajectory using bone screw 207. One or more additional bone screws 210 may be also employed. The screws are illustrated as being joined by a plate 250, wherein plate 250 is then anchored to another vertebral bone by additional bones screws (not shown).

Alternatively, bone screw assemblies, such as, e.g., bone screw assembly 105 of FIGS. 15 and 16, may be placed into the vertebral bone using the same method/trajectory and then connected to additional bone screws at adjacent vertebral levels by an interconnecting rod (instead of a plate). It will be understood that various bone plate are known in the art and that any applicable bone plate may be additionally or alternatively used. Further, many bone plates include features and specialized sub-segments, such as, e.g., screw to plate locking features, slots that allow bone screws to move/subside therein, movable sub-segments, expandable size configurations, and the like. On or more of these features may be included, where appropriate, in generic plate 250.

An additional implementation for the method of bone screw placement is shown in FIG. 20B. While similar to that of FIG. 20A, the screw trajectory in this implementation is selected so that the distal aspect of the bone screw passes through the body-pedicle junction and enters the anterior aspect of the ipsilateral pedicle. As in FIG. 20A, one or more additional bone screws 210 may be also employed at each vertebral level and bone screws at different vertebral bones may be coupled by use of an interconnecting plate and/or rod.

While various embodiments with different bone screw trajectories have been illustrated, it will be understood that screws having differing trajectories can be combined to form additional embodiments. For example, a target FSU may be approached using a single corridor to the vertebral bodies of the FSU's superior and inferior vertebral bones. The incision is preferably positioned anterior to coronal plane T (shown in FIGS. 3 and 5) and the corridor formed between the incision and the spine is developed through the extra-spinal and non-bony tissues of the abdominal cavity. The corridor may be at least partially contained within the retro-peritoneal space.

Figure 21A:
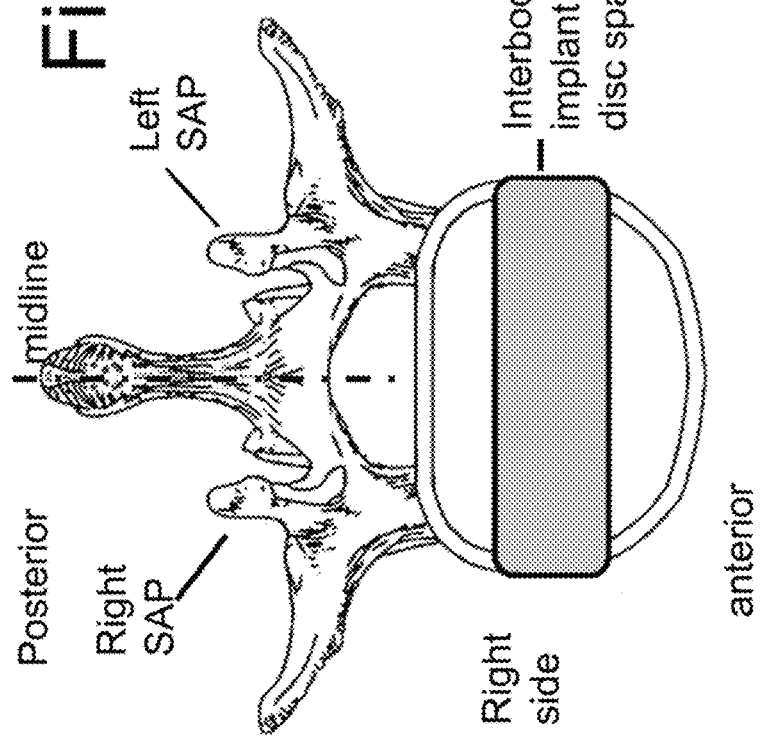
FIGS. 21A and 21B are top plan views of a subject's spine illustrating additional embodiments of interbody implant and bone screw/fastener placement.

Once the spine is reached, the intervertebral disc space of the target FSU is accessed and an orthopedic implant may be positioned inside of the disc space after removal of at least a portion of the natural disc material that is contained therein. The intervertebral disc space can be accessed through the direct anterior approach 505, the antero-lateral approach 507, and/or the direct lateral approach 509 of FIG. 5. An to implant that is placed within the disc space may be a device configured to produce a bone fusion between the superior and inferior vertebral bones of the target FSU. Further, the implant can be positioned to overly at least segment of apophyseal ring (FIG. 5) of the superior and/or inferior vertebral bone of the target FSU, as illustrated by implant 510 shown in FIG. 21A.

After implant placement, at least one bone screw may be advanced into the each of the superior and inferior vertebral bodies of the target FSU. At least one bone screw is positioned into each of the bodies of the two vertebral bones of the target FSU. The screw(s) in each of the superior and inferior bodies of the target FSU can be then interconnected with a plate and/or a rod. Using the same corridor through the extra-spinal tissues of the abdominal cavity, at least one additional bone screw may be placed into the portion of the FSU that is posterior to coronal line T. This additional screw may be advanced in an anterior to posterior direction across coronal plane T and then guided across the ipsilateral facet joint of the FSU (FIG. 11). This trans-facet screw then traverses the SAP of the inferior vertebral bone (from lateral to medial) and the space of the facet joint, and enters the TAP of the superior vertebral bone of the target FSU (FIG. 14).

Alternatively, a first bone screw may be advanced in an anterior to posterior direction across coronal plane T and then guided into the inferior vertebral bone of the target FSU (with or without traversing a segment of the superior vertebral bone). A second bone screw may be also advanced from an anterior to posterior direction across coronal plane T and then guided into the superior vertebral bone of the target FSU (with or without traversing a segment of the inferior vertebral bone). The first and second bone screws may subsequently be interconnected using a rod and/or plate. (As noted above, the term "bone screw" as used herein may include, without limitation, bone screw assembly 105 of FIG. 15 or any other appropriate bone screw that is adapted to couple with an interconnecting rod and/or plate.) In this embodiment, the first and/or second bone screw may be advanced into bone using the trajectory illustrated in FIGS. 18A and 18B (and discussed above).

Figure 21B:
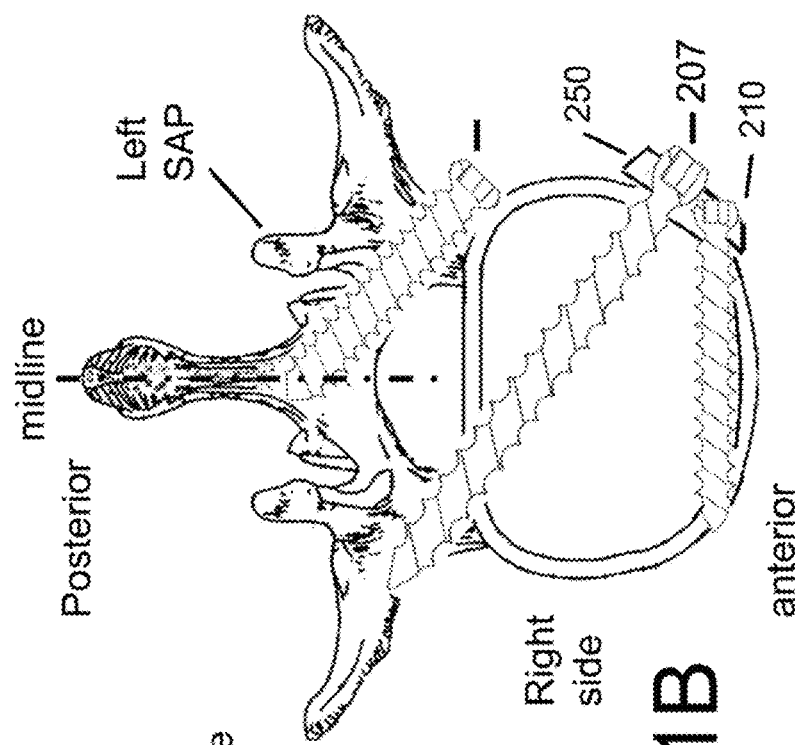

FIG. 21B illustrates an example implementation wherein at least one bone screw is positioned into the vertebral body anterior to coronal plane T and at least one additional screw is advanced from an anterior to posterior direction across coronal plane T and is, at least partially, anchored to a segment of the vertebral bone that is posterior to coronal plane T. Note that additional bone screws (for example, another vertebral body screw) may be also employed, such as bone screw 210. For example, at least one bone screw of one of the vertebral bodies may be positioned so that its distal aspect enters the contralateral pedicle, as shown in FIG. 20A. A plate (or rod), such as, e.g., plate 250, may be used to couple some of the bone screws that are anchored within one vertebral bone to bone screws anchored into other vertebral bones.

Figure 22:
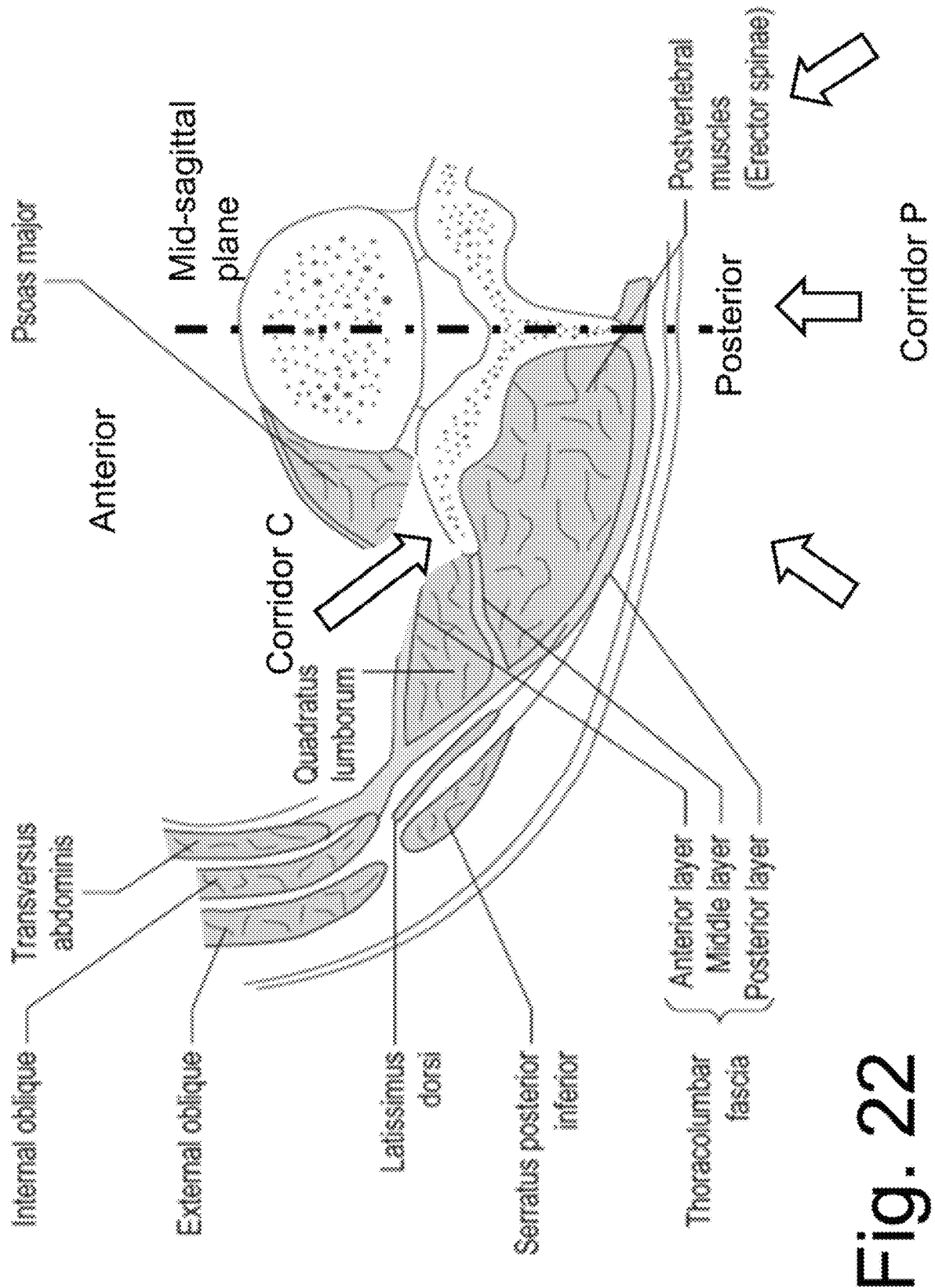
FIG. 22 is a schematic cross-section view of a subject's spine and surrounding anatomy illustrating an additional embodiment of corridors to access the target vertebral bone.

An exemplary method for access and possible instrumentation of an anterior and posterior aspect of the target FSU through a single abdominal corridor having a starting point at a skin that is anterior to coronal plane T is described above. Additional access of the posterior aspect of the FSU may be achieved by making a skin incision posterior to coronal plane T (for example, on the skin of the back of a subject) approaching the spine from a posterior to anterior trajectory. The latter exemplary method is illustrated in FIG. 22 wherein the anterior aspect of the FSU may be accessed through at least one of the approaches of FIG. 5 (i.e., approaches 505, 507 and 509) and the posterior aspect of the FSU may be accessed through corridor C, as previously described, as well as through corridor P shown in FIG. 22. Access of the FSU through corridor P allows for direct bone screw placement along the longitudinal access of the pedicle (FIG. 23A) and/or along the cortical bone screw trajectory discussed above (FIG. 23B). While the illustrated bone screw is placed in the right side of the vertebral bone, it is understood that the bone screw placement trajectories of FIGS. 23A and 23B may be employed on either side of the vertebral bone.

Figure 24:
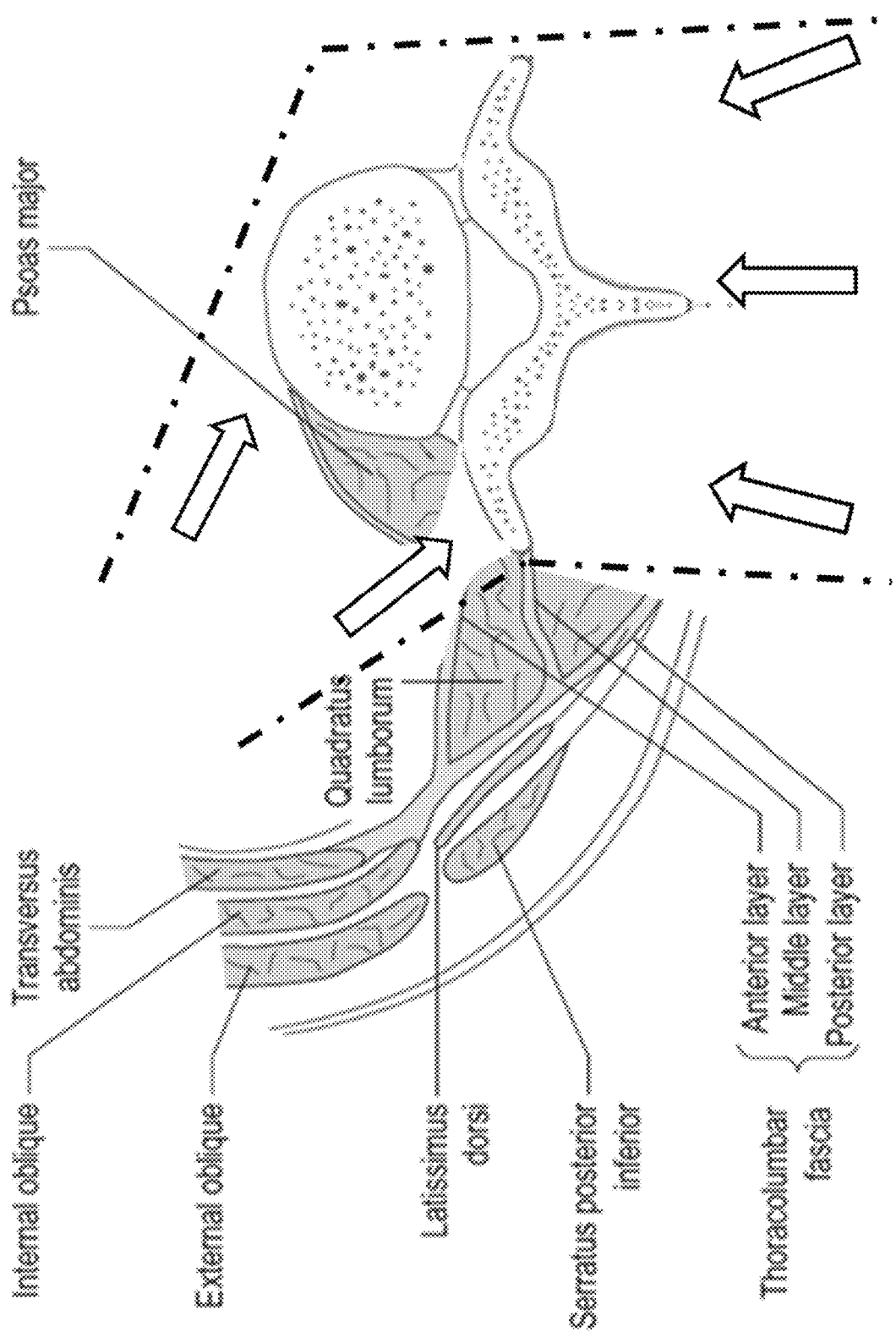
FIG. 24 is cross-sectional view of a subject's spine and surrounding anatomy illustrating an additional embodiment of corridors to access the target vertebral bone.

The addition of corridor P in accessing the target FSU allows both corridors to intersect at the level of the transverse process (as shown in FIG. 24), thereby providing a direct and continuous anterior/posterior corridor to the FSU. This method allows circumferential access to the vertebral bone, as shown by the area within the uneven broken lines of FIG. 24, while the patient is in a single position (such as, e.g., the lateral decubitus position) without the need to reposition the patient on the operating room table and to repeat the surgical preparation and drape process. It also allows for concurrent to anterior and posterior work, wherein a first surgeon works through corridor C while a second surgeon works through corridor P. As previously noted, the transverse process may be removed, if desired, and this removal will further increase the size of the direct anterior/posterior corridor, as shown in FIGS. 25A-25C. This wider access can be used to provide comprehensive decompression of the neural tissues within the spinal canal. It can also be used to correct spinal deformity with greater ease and safety than is currently available using conventional methods.

FIG. 26 illustrates an example of deformity correction that may be achieved with the anterior/posterior access to the FSU methodology discussed above. The access corridor allows for more complete release (which comprises releasing the connections between adjacent vertebral bone) so that vertebral realignment can be performed. Limited release of adjacent vertebral bone is a major factor in suboptimal surgical realignment of the vertebral bones. The enlarged access window will also allow more thorough resection of vertebral segments in order to optimize the desired curvature in the post-operative spine.

FIG. 26 illustrates an example of segmental resection of the shaded area in order to produce a greater lordotic angle across the segment. The lordotic angle may be measured as the angle between the superior surface of a superior vertebral bone and the inferior surface of an inferior vertebral bone. The shaded area is removed from the left lateral side wall of the vertebral bone to the right lateral side wall of the vertebral bone. This procedure is known to those of ordinary skill in the art as a "pedicle subtraction osteotomy" and is described in detail in *Decision Making Regarding Smith-Petersen vs. Pedicle Subtraction Osteotomy vs. Vertebral Column Resection for Spinal Deformity* by Bridwell, K H. SPINE Volume 31, Number 19 Suppl, pp S171S178 2006, which is herein incorporated by reference in its entirety.

The procedure may be performed with less morbidity when at least a portion of the osteotomy (such as, e.g., the segment involving removal of the pedicle and/or body segment) is performed through corridor C. Note that the lordotic angle, while increased in FIG. 26B by closing the bony defect after the osteotomy, may be increased further by positioning a lordosis implant between the bony surfaces to be re-apposed (FIG. 26C). In fact, the implant may be adjustable in its lordotic (or even kyphotic) angle so that the surgeon may further adjust the angle across the target FSU after the implant has been positioned within the osteotomy site.

The totality of the above described methods, from selection of the target level to implant to the final placement of implant, can be performed under imaging guidance (such as X-ray, CT, MRI, computer-guided imaging and the like). Further, the operation can be performed using percutaneous or minimally invasive surgical techniques with or without the aid of electrophysiological monitoring. The latter include techniques such as electromyography (EMG), somato-sensory, motor evoked potentials and the like. These and other techniques may be used and are intended to alert the operating surgeon to the presence of nerves and other neural elements within the surgical corridor. For example, EMG identification of nerves permits the surgeon to navigate the surgical site with increased safety and lessens the possibility of nerve injury.

The devices disclosed herein and/or any of their components can be made of any biologically adaptable or compatible materials. Materials considered acceptable for biological implantation are well known and include, but are not limited to, stainless steel, titanium, tantalum, combination metallic alloys, various plastics (such as PEEK and the like), resins, ceramics, biologically absorbable materials and the like. Any components may be also coated/made with osteoconductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as, e.g., porous titanium, titanium wire mesh, plasma-sprayed titanium, tantalum, porous CoCr, and the like) and/or provided with a bioactive coating, (such as tantalum, and/or helical rosette carbon nanotubes or other carbon nanotube-based coating) in order to promote bone in-growth or establish a mineralized connection between the bone and the implant, and to reduce the likelihood of implant loosening. The system or any of its components may be made by "additive manufacturing", such as, e.g., "3D" printing. Lastly, the system or any of its components can also be entirely or partially made of a shape memory material or other deformable material.

While this specification contains many specific examples and embodiments, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination.

Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings and/or described in the specification in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based the present disclosure.

What is claimed is:

1. A method for stabilization of a functional spinal unit of a subject, the functional spinal unit comprising a superior vertebral bone, an inferior vertebral bone and an intervertebral disc space disposed therebetween, the method comprising:

forming a skin incision in the subject, the skin incision positioned anterior to a coronal plane, the coronal plane (i) defining a vertical plane of the subject (ii) extending from an anterior-most point of a right transverse process of the inferior vertebral bone to an anterior-most point of a left transverse process of the inferior vertebral bone; and (iii) dividing the inferior vertebral bone into an anterior segment and a posterior segment of the functional spinal unit;

forming, from the skin incision, an intra-abdominal surgical corridor that traverses at least a portion of an abdominal cavity of the subject;

extending a first branch of the intra-abdominal surgical corridor to the anterior segment of the functional spinal unit;

advancing an orthopedic implant through at least the first branch of the intra-abdominal surgical corridor and at least partially into the intervertebral disc space of the functional spinal unit;

extending a second branch of the intra-abdominal surgical corridor to the posterior segment of the functional spinal unit, the second branch extending (i) through at least an anterior layer of a thoracolumbar fascia and (ii) posterior to at least a segment of a psoas muscle of the subject, the thoracolumbar fascia and the psoas muscle both positioned ipsilateral to the skin incision;

manipulating a bony segment of the posterior segment of the functional spinal unit via at least the second branch of the intra-abdominal surgical corridor; and advancing a first fastener at least partially through a first pedicle of at least one of the inferior vertebral bone or the superior vertebra bone, the first pedicle positioned ipsilateral to the skin incision, wherein the first fastener traverses the first pedicle in an anterio-lateral to a posterio-medial direction.

2. The method of claim 1, wherein the first branch of the intra-abdominal surgical corridor extends to a side surface of the intervertebral disc space.

3. The method of claim 1, the method further comprising manipulating a first facet joint of the functional spinal unit via at least the second branch of the intra-abdominal surgical corridor, the first facet joint positioned ipsilateral to the skin incision.

4. The method of claim 3, wherein the manipulating the first facet joint comprises advancing a bone fastener in a lateral to medial trajectory through a superior articulating process of the inferior vertebral bone and into an inferior articulating process of the superior vertebral bone, the superior articulating process and the inferior articulating process comprising the first facet joint.

5. The method of claim 3, wherein the manipulating the first facet joint comprises removing at least a segment of the first facet joint.

6. The method of claim 1, wherein the manipulating the bony member of the posterior segment of the functional spinal unit comprises removing at least a bony segment of a transverse process of the functional spinal unit, the transverse process positioned ipsilateral to the skin incision.

7. The method of claim 6, further comprising implanting, via the first branch of the intra-abdominal surgical corridor, a portion of the bony segment of the transverse process within the intervertebral disc space.

8. The method of claim 1, further comprising advancing second a bone fastener into a lateral bony surface of the other of the inferior vertebral bone or the superior vertebral bone.

9. The method of claim 8, further comprising advancing the second bone fastener within a pedicle portion of the other of the inferior vertebral or the superior vertebral bone.

10. The method of claim 8, further comprising advancing the second bone fastener in a lateral to medial trajectory within a lamina portion of the other of the inferior vertebral bone or the superior vertebral bone.

11. A method for treatment of a functional spinal unit of a subject, the functional spinal unit comprising a superior vertebral bone, an inferior vertebral bone and an intervertebral disc space disposed therebetween, the method comprising:
forming a skin incision in the subject, the skin incision positioned anterior to a coronal plane, wherein the coronal plane (i) defines a vertical plane of the subject, the vertical plane comprising at least a portion of a posterior wall of the inferior vertebral bone; and (ii) divides the functional spinal unit into an anterior segment and a posterior segment;
forming an intra-abdominal tissue corridor from the skin incision through at least a portion of an abdominal cavity of the subject and onto a side surface of the intervertebral disc space;
advancing an orthopedic implant at least partially into the intervertebral disc space via at least a portion of the intra-abdominal tissue corridor;
forming a limb of the intra-abdominal tissue corridor that extends towards the posterior segment of the functional spinal unit, the limb (i) traversing at least a segment of the abdominal cavity and (ii) extending through the coronal plane and posterior to a psoas muscle, and (iii) extending through at least an anterior layer of a thoracolumbar fascia in an anterior to posterior direction, the psoas muscle and the thoracolumbar fascia positioned ipsilateral to the skin incision;
advancing a first fastener (i) superior to a first transverse process of the inferior vertebral bone, the first transverse process positioned ipsilateral to the skin incision; and (ii) at least partially through a first facet joint of the functional spinal unit in a lateral-to-medial trajectory, the first facet joint ipsilateral to the skin incision.

12. The method of claim 11, wherein the fastener sequentially traverses a superior articulating process of the inferior vertebral bone and an inferior articulating process of the superior vertebral bone in a lateral to medial trajectory.

13. The method of claim 11, further comprising removing at least a segment of a first facet joint.

14. The method of claim 11, further comprising removing at least a bony segment of a transverse process of the functional spinal unit, the transverse process positioned ipsilateral to the skin incision.

15. The method of claim 14, further comprising implanting, via the intra-abdominal tissue corridor, the at least bony segment of the transverse process into the intervertebral disc space.

16. The method of claim 11, further comprising advancing a second bone fastener into a first pedicle of at least one of the inferior vertebral bone or the superior vertebral bone.

17. The method of claim 16, further comprising advancing the second bone fastener in an anterior-lateral to a posterior-medial direction within the first pedicle, the first pedicle ipsilateral to the skin incision.

18. The method of claim 16, further comprising advancing the second bone fastener in a medial to lateral trajectory within the first pedicle, the first pedicle contralateral to the skin incision.

19. The method of claim 11, further comprising positing, at the anterior segment of the functional spinal unit via the first extension of the intra-abdominal tissue corridor, a second orthopedic implant onto a side surface the inferior vertebral bone and a side surface of the superior vertebral bone.

20. A method for stabilization of a functional spinal unit of a subject, the functional spinal unit comprising a superior vertebral bone, an inferior vertebral bone, and an intervertebral disc space disposed there between, the method comprising:
forming a skin incision in the subject, the skin incision positioned anterior to a coronal plane, wherein the coronal plane: (i) defines a vertical plane of the subject, the vertical plane comprising at least a portion of a posterior wall of the superior vertebral bone and (ii) divides the functional spinal unit into an anterior segment and a posterior segment;
forming an intra-abdominal surgical corridor extending from the skin incision and traversing at least a portion of an abdominal cavity of the subject;
extending the intra-abdominal surgical corridor onto a side surface of the intervertebral disc space of the functional spinal unit;
advancing an orthopedic implant through the intra-abdominal surgical corridor and at least partially into the intervertebral disc space of the functional spinal unit;
extending a limb of the intra-abdominal surgical corridor onto the posterior segment of the functional spinal unit, the limb (i) positioned posterior to at least a segment of a psoas muscle of the subject and (ii) advancing through at least an anterior layer of a thoracolumbar fascia in an anterior to posterior direction, the thoracolumbar fascia and the psoas muscle both positioned ipsilateral to the skin incision; and
advancing a first fastener at least partially through the limb and onto at least posterior segment of one of the inferior vertebral bone or the superior vertebra bone; and
wherein the first fastener (i) traverses the first coronal plane in an anterior-to-posterior trajectory; and (ii) traverses, in an anterio-lateral to a posterio-medial direction, a segment of at least one of the superior vertebral bone or the inferior vertebral bone.

21. The method of claim 20, wherein the first fastener traverses the lamina segment of the superior vertebral bone.

22. The method of claim 20, wherein the first fastener traverses the lamina segment of the inferior vertebral bone.

23. The method of claim 20, the method comprising manipulating a first facet joint of the functional spinal unit via at least the limb of the intra-abdominal surgical corridor, the first facet joint positioned ipsilateral to the skin incision.

24. The method of claim 23, wherein the manipulating the first facet joint comprises advancing the first fastener in a lateral to medial trajectory through a superior articulating process of the inferior vertebral bone and into an inferior articulating process of the superior vertebral bone, the superior articulating process and the inferior articulating process comprising the first facet joint.

25. The method of claim 23, wherein the manipulating the first facet joint comprises removing at least a segment of the first facet joint.

26. The method of claim 20, further comprising removing at least a bony segment of a transverse process of the functional spinal unit, the transverse process positioned ipsilateral to the skin incision.

27. The method of claim 26, further comprising implanting, via the intra-abdominal surgical corridor, a portion of the bony segment of the transverse process within the intervertebral disc space.

28. The method of claim 20, further comprising advancing a second bone fastener into a lateral bony surface of the other of the inferior vertebral bone or the superior vertebral bone.

29. The method of claim 20, further comprising advancing a second bone fastener within a pedicle portion the inferior vertebral bone, the second faster traversing the portion of the pedicle in a lateral to medial direction.

30. The method of claim 20, further comprising advancing a second bone fastener within a pedicle portion the superior vertebral bone, the second faster traversing the portion of the pedicle in a lateral to medial direction.

\* \* \* \* \*